United States Patent
Aubrey et al.

(10) Patent No.: US 11,834,466 B2
(45) Date of Patent: Dec. 5, 2023

(54) BENZOXABOROLE COMPOUNDS AND FORMULATIONS THEREOF

(71) Applicant: 5Metis, Inc., Durham, NC (US)

(72) Inventors: Marissa Aubrey, Durham, NC (US);
Chun Yu Liu, Durham, NC (US);
Chunliang Liu, Cary, NC (US);
Michael Samuels, Durham, NC (US);
Yong-Kang Zhang, San Jose, CA (US);
Yasheen Zhou, Moraga, CA (US)

(73) Assignee: 5Metis, Inc., Durham, NC (US)

( * ) Notice: Subject to any disclaimer, the term of this patent is extended or adjusted under 35 U.S.C. 154(b) by 340 days.

(21) Appl. No.: 15/733,157

(22) PCT Filed: Nov. 30, 2018

(86) PCT No.: PCT/US2018/063389
§ 371 (c)(1),
(2) Date: May 29, 2020

(87) PCT Pub. No.: WO2019/108982
PCT Pub. Date: Jun. 6, 2019

(65) Prior Publication Data
US 2020/0385409 A1 Dec. 10, 2020

Related U.S. Application Data

(60) Provisional application No. 62/593,226, filed on Nov. 30, 2017, provisional application No. 62/743,489, filed on Oct. 9, 2018.

(51) Int. Cl.
| | |
|---|---|
| *C07F 5/02* | (2006.01) |
| *A01N 25/04* | (2006.01) |
| *A01N 25/08* | (2006.01) |
| *A01N 55/08* | (2006.01) |
| *A01N 25/02* | (2006.01) |
| *A61K 31/69* | (2006.01) |
| *A61K 45/06* | (2006.01) |

(52) U.S. Cl.
CPC .............. *C07F 5/02* (2013.01); *A01N 25/04* (2013.01); *A01N 25/08* (2013.01); *A01N 55/08* (2013.01)

(58) Field of Classification Search
None
See application file for complete search history.

(56) References Cited

U.S. PATENT DOCUMENTS

| | | | |
|---|---|---|---|
| 3,708,573 A | 1/1973 | Yoshinaga et al. | |
| 4,672,065 A | 6/1987 | Spatz | |
| 4,936,901 A | 6/1990 | Surgant et al. | |
| 5,880,188 A | 3/1999 | Austin et al. | |
| 7,582,621 B2 * | 9/2009 | Baker | A61P 31/14 514/64 |
| 7,767,657 B2 * | 8/2010 | Baker | A61K 31/70 514/64 |
| 8,669,207 B1 | 3/2014 | Jacobson et al. | |
| 9,138,001 B2 * | 9/2015 | Maclean | A23B 4/16 |
| 9,138,002 B2 | 9/2015 | Jacobson et al. | |
| 9,426,996 B2 | 8/2016 | Maclean et al. | |
| 9,585,396 B2 | 3/2017 | Malefyt et al. | |
| 9,617,285 B2 | 4/2017 | Akama et al. | |
| 9,737,075 B2 * | 8/2017 | Benkovic | A01N 25/08 |
| 10,070,649 B2 | 9/2018 | Malefyt et al. | |
| 10,130,096 B2 * | 11/2018 | Bobbio | A01N 25/00 |
| 10,562,921 B2 † | 2/2020 | Akama | |
| 11,066,424 B2 * | 7/2021 | Liu | C07F 5/025 |
| 2006/0234981 A1 | 10/2006 | Baker et al. | |
| 2007/0155699 A1 | 7/2007 | Baker et al. | |
| 2007/0286822 A1 | 12/2007 | Sanders et al. | |
| 2012/0115813 A1 | 5/2012 | Hernandez et al. | |
| 2012/0214765 A1 | 8/2012 | Akama et al. | |

(Continued)

FOREIGN PATENT DOCUMENTS

| | | |
|---|---|---|
| AU | 27071/95 B1 | 10/1997 |
| CN | 105101791 A | 11/2015 |

(Continued)

OTHER PUBLICATIONS

Adamczyk-Wozniak et al., "Influence of the Substituents on the Structure and Properties of Benzoxaboroles," The Journal of Physical Chemistry A, vol. 114, No. 6, Jan. 21, 2010, pp. 2324-2330.
Tomsho et al., "Ring Structure and Aromatic Substituent Effects on the pKa of the Benzoxaborole Pharmacophore," ACS Med. Chem. Lett., 3, 2012, pp. 48-52.
CN 201880088201.8, Office Action, dated Mar. 24, 2022, 10 pages (English translation attached).
EP 18883841.1, Partial Supplementary European Search Report, dated Aug. 20, 2021, 16 pages.
IN 202037027381, First Examination Report, dated Nov. 23, 2021, 12 pages.
International Search Report from corresponding PCT/US2020/044071, dated Nov. 10, 2020.

(Continued)

*Primary Examiner* — Alton N Pryor
(74) *Attorney, Agent, or Firm* — Kilpatrick Townsend & Stockton LLP

(57) ABSTRACT

A benzoxaborole formulation composition including a benzoxaborole, a non-ionic surfactant, or a non-ionic and ionic surfactant mixture, and a carrier is described herein. At least one of the non-ionic surfactant, the non-ionic and ionic surfactant mixture, and the carrier comprise a Lewis base or a N—H or O—H bond. The carrier is a solid or a liquid. Benzoxaborole compounds and methods of using the compounds and formulations of the compounds are described. For example, a method for reducing, preventing, ameliorating, or inhibiting an infestation by a pathogen by applying a compound or a formulation of a compound, wherein the pathogen is selected from insects, nematodes, bacteria, microbes, fungi, protozoa, viruses, and parasites, or any combinations thereof is described.

10 Claims, 56 Drawing Sheets

(56) References Cited

U.S. PATENT DOCUMENTS

| | | | |
|---|---|---|---|
| 2014/0221312 A1* | 8/2014 | Maclean | A01N 27/00 514/64 |
| 2014/0259230 A1 | 9/2014 | Bobbio et al. | |
| 2015/0133402 A1 | 5/2015 | Baker et al. | |
| 2015/0223466 A1 | 8/2015 | Malefyt | |
| 2016/0324160 A1 | 11/2016 | Benkovic et al. | |
| 2016/0374344 A9 | 12/2016 | Malefyt et al. | |
| 2017/0000133 A1 | 1/2017 | Rajan et al. | |
| 2017/0037258 A1 | 2/2017 | Benkovic et al. | |
| 2017/0164615 A1 | 6/2017 | Malefyt et al. | |
| 2017/0164616 A1 | 6/2017 | Gane et al. | |
| 2017/0327519 A1† | 11/2017 | Akama | |
| 2018/0009831 A1 | 1/2018 | Kovi et al. | |
| 2019/0159457 A1 | 5/2019 | Liu et al. | |
| 2020/0055878 A1 | 2/2020 | Liu et al. | |
| 2020/0113184 A1 | 4/2020 | MacLean et al. | |
| 2021/0059254 A1 | 3/2021 | Jacobson et al. | |

FOREIGN PATENT DOCUMENTS

| | | |
|---|---|---|
| CN | 105712969 A | 6/2016 |
| CN | 111233908 A | 6/2020 |
| EP | 0493671 A1 | 11/1991 |
| EP | 2810946 B1 | 4/2016 |
| EP | 2950644 B1 | 7/2017 |
| KR | 10-2014-0093598 A | 7/2014 |
| WO | 1995/033754 A1 | 12/1995 |
| WO | 1996/032270 A1 | 10/1996 |
| WO | 1997/033890 A1 | 9/1997 |
| WO | 1998/044140 A1 | 10/1998 |
| WO | 2000/026345 A1 | 5/2000 |
| WO | 2000/026356 A1 | 5/2000 |
| WO | 2002/034946 A2 | 5/2002 |
| WO | 2003/013224 A2 | 2/2003 |
| WO | 2003/100163 A1 | 12/2003 |
| WO | 2004/011601 A2 | 2/2004 |
| WO | 2004/039986 A1 | 5/2004 |
| WO | 2004/053062 A2 | 6/2004 |
| WO | 2004/072235 A2 | 8/2004 |
| WO | 2004/074492 A1 | 9/2004 |
| WO | 2005/054480 A2 | 6/2005 |
| WO | 2005/059103 A2 | 6/2005 |
| WO | 2005/061720 A2 | 7/2005 |
| WO | 2005/103266 A1 | 11/2005 |
| WO | 2005/103301 A2 | 11/2005 |
| WO | 2006/089067 A2 | 8/2006 |
| WO | 2006/108674 A2 | 10/2006 |
| WO | 2006/108675 A2 | 10/2006 |
| WO | 2006/128569 A2 | 12/2006 |
| WO | 2006/128570 A1 | 12/2006 |
| WO | 2006/128571 A2 | 12/2006 |
| WO | 2006/128573 A2 | 12/2006 |
| WO | 2007/017186 A1 | 2/2007 |
| WO | 2007/024782 A2 | 3/2007 |
| WO | 2007/027777 A2 | 3/2007 |
| WO | 2007/078340 A2 | 7/2007 |
| WO | 2007/091277 A2 | 8/2007 |
| WO | 2007/095638 A2 | 8/2007 |
| WO | 2007/131072 A2 | 11/2007 |
| WO | 2007/140256 A1 | 12/2007 |
| WO | 2007/142840 A2 | 12/2007 |
| WO | 2008/022872 A1 | 2/2008 |
| WO | 2008/070257 A2 | 6/2008 |
| WO | 2008/112019 A2 | 9/2008 |
| WO | 2009/064652 A1 | 5/2009 |
| WO | 2009/100188 A2 | 8/2009 |
| WO | 2009/102873 A1 | 8/2009 |
| WO | 2009/111263 A1 | 9/2009 |
| WO | 2009/111676 A2 | 9/2009 |
| WO | 2009-124920 A2 | 10/2009 |
| WO | 2010/024976 A1 | 3/2010 |
| WO | 2010/037016 A1 | 4/2010 |
| WO | 2010/077816 A1 | 7/2010 |
| WO | 2010/110400 A1 | 9/2010 |
| WO | 2010/117735 A1 | 10/2010 |
| WO | 2010/117737 A1 | 10/2010 |
| WO | 2011/022469 A2 | 2/2011 |
| WO | 2011/034704 A1 | 3/2011 |
| WO | 2011/060199 A1 | 5/2011 |
| WO | 2011/062904 A1 | 5/2011 |
| WO | 2011/066360 A1 | 6/2011 |
| WO | 2011/066384 A1 | 6/2011 |
| WO | 2011/075593 A1 | 6/2011 |
| WO | 2011/075595 A1 | 6/2011 |
| WO | 2013-050591 A2 | 4/2013 |
| WO | 2013/050591 A2 | 4/2013 |
| WO | 2014/120715 A2 | 8/2014 |
| WO | 2014-120715 A2 | 8/2014 |
| WO | 2014/173880 A1 | 10/2014 |
| WO | 2014/197634 A2 | 12/2014 |
| WO | 2015/097276 A1 | 7/2015 |
| WO | 2015-097276 A1 | 7/2015 |
| WO | 2015/171186 A1 | 11/2015 |
| WO | 2015-175157 A1 | 11/2015 |
| WO | 2015/175157 A1 | 11/2015 |
| WO | 2016/079536 A1 | 5/2016 |
| WO | 2016-113303 A1 | 7/2016 |
| WO | 2016/113313 A1 | 7/2016 |
| WO | 2016-113313 A1 | 7/2016 |
| WO | 2016/128949 A1 | 8/2016 |
| WO | 2016-128949 A1 | 8/2016 |
| WO | 2016/130658 A1 | 8/2016 |
| WO | 2016/164589 A1 | 10/2016 |
| WO | 2016-164589 A1 | 10/2016 |
| WO | 2017/024022 A1 | 2/2017 |
| WO | 2017/183043 A1 | 10/2017 |
| WO | 2017/195069 A1 | 11/2017 |
| WO | 2019-108982 A1 | 6/2019 |
| WO | 2019/152641 A1 | 8/2019 |
| WO | 2020/123881 A1 | 6/2020 |
| WO | 2021/021932 A1 | 2/2021 |

OTHER PUBLICATIONS

International Search Report from corresponding PCT/US2019/047073, dated Dec. 18, 2019.

Baker, Stephen J., et al., "Discovery of a New Boron-Containing Antifungal Agent, 5-Fluoro-1,3-dihydro-1-hydroxy-2, 1-benzoxaborole (AN2690), for the Potential Treatment of Onychomycosis," Journal of Medicinal Chemistry, vol. 49, No. 15, pp. 4447-4450 (2006).

Baur et al., "Polydisperse ethoxylated fatty alcohol surfactants as accelerators of cuticular penetration. 1. Effects of ethoxy chain length and the size of the penetrants" Pesticide Science 51(2), 131-152, Oct. 1997.

Haynes et al. Arylboronic Acids. VIII. Reactions of Boronophthalide. R.R. Haynes and H.R. Snyder. Nov. 1964; p. 3229-3233.

Hosseinzadeh, R. et al., "A new selective fluorene-based fluorescent internal charge transfer (ICT) sensor for sugar alcohols in aqueous solution", Analytical and bioanalytical chemistry, 2016, vol. 408, No. 7, pp. 1901-1908.

Hui, Xiaoying, et al., "In Vitro Penetration of a Novel Oxaborole Antifungal (AN2690) into the Human Nail Plate," Journal of Pharmaceutical Sciences, vol. 96, No. 10, pp. 2621-2631 (Oct. 2007).

Li, Xianfeng, et al., "Synthesis and SAR of acyclic HCV NS3 protease inhibitors with novel P4-benzoxaborole moieties," Bioorganic & Medicinal Chemistry Letters, 21 (2011) 2048-2054.

Manabe, Kei, et al., "A Repetitive One-Step Method for Oligoarene Synthesis Using Catalyst-Controlled Chemoselective Cross-Coupling," Org. Lett., vol. 13, No. 9, pp. 2436-2439 (2011).

Rock et al., "An Antifungal Agent Inhibits an Aminoacyl-tRNA Synthetase by Trapping tRNA in the Editing Site," Science 316, 1759 (2007).

Sene, Saad, et al., "A combined experimental-computational study of benzoxaborole crystal structures," CrystEngComm, 2014, 16, 4999-5011.

Usutani, H. et al., "Development and scale-up of a flow chemistry lithiation-borylation route to a key boronic acid starting material", Organic process research & development, 2017, vol. 21, No. 4, pp. 669-673.

(56) References Cited

OTHER PUBLICATIONS

Berge et al., Pharmaceutical Salts, Journal of Pharmaceutical Science 66:1-19 (1977).
PUBCHEM 403788 Deposited Mar. 26, 2005, pp. 1-17, p. 2 (https://pubchem.ncbi.nlm.nih.gov/compound/403788#section=Information-Sources).

\* cited by examiner
† cited by third party

| Structure | IUPAC Name | MS (m/z) | HPLC purity (220 nm) | HPLC purity (254 nm) |
|---|---|---|---|---|
| C₈H₈BClO₂ | 5-chloro-7-methylbenzo[c][1,2]oxaborol-1(3H)-ol | [M-H]-=181.0 | 100 | 100 |
| C₈H₈BClO₂ | 5-chloro-6-methylbenzo[c][1,2]oxaborol-1(3H)-ol | [M-H]-=181.1 | 100 | 100 |
| C₈H₇BO₄ | 1-hydroxy-1,3-dihydrobenzo[c][1,2]oxaborole-4-carboxylic acid | [M+H]+=179.1 | 95.77 | 100 |
| C₉H₈BClO₄ | methyl 7-chloro-1-hydroxy-1,3-dihydrobenzo[c][1,2]oxaborole-5-carboxylate | [M+H]+=227.1 | 99.07 | 99.27 |
| C₈H₈BFO₂ | 5-fluoro-7-methylbenzo[c][1,2]oxaborol-1(3H)-ol | [M-H]-=165.1 | 100 | 100 |
| C₈H₆BClO₄ | 7-chloro-1-hydroxy-1,3-dihydrobenzo[c][1,2]oxaborole-5-carboxylic acid | [M-H]-=211.0 | 99.84 | 100 |
| C₉H₈BClO₄ | methyl 7-chloro-1-hydroxy-1,3-dihydrobenzo[c][1,2]oxaborole-4-carboxylate | [M+H]+=227.1 | 100 | 100 |

FIG. 2A

| Structure | IUPAC Name | MS (m/z) | HPLC purity (220 nm) | HPLC purity (254 nm) |
|---|---|---|---|---|
| C₈H₈BClO₂ | 5-chloro-4-methylbenzo[c][1,2]oxaborol-1(3H)-ol | [M-H]-=181.1 | 98.07 | 89.82 |
| C₁₀H₁₁BO₄ | methyl 1-hydroxy-7-methyl-1,3-dihydrobenzo[c][1,2]oxaborole-6-carboxylate | [M+H]+=207.0 | 99 | 95.72 |
| C₈H₈BClO₂S | 5-chloro-4-(methylthio)benzo[c][1,2]oxaborol-1(3H)-ol | [M-H]-=213.0 | 98.4 | 99.54 |
| C₈H₈BClO₃S | 5-chloro-4-(methylsulfinyl)benzo[c][1,2]oxaborol-1(3H)-ol | [M+H]+=230.9 | 99.82 | 100 |
| C₈H₉BClNO₂ | 5-chloro-6-(methylamino)benzo[c][1,2]oxaborol-1(3H)-ol | [M+H]+=198.1 | 97.77 | 99.22 |
| C₉H₁₁BClNO₂ | 5-chloro-6-(dimethylamino)benzo[c][1,2]oxaborol-1(3H)-ol | [M+H]+=212.3 | 99.74 | 100 |
| C₇H₆BClO₃ | 5-chlorobenzo[c][1,2]oxaborole-1,4(3H)-diol | [M-H]-=182.9 | 96.08 | 95.76 |

FIG. 2B

| Structure | IUPAC Name | MS (m/z) | HPLC purity (220 nm) | HPLC purity (254 nm) |
|---|---|---|---|---|
| C₉H₁₁BClNO₂ | 5-chloro-4-(dimethylamino)benzo[c][1,2]oxaborol-1(3H)-ol | [M+H]+=212.0 | 100 | 100 |
| C₉H₁₁BClNO₂ | 5-chloro-6-(ethylamino)benzo[c][1,2]oxaborol-1(3H)-ol | [M+H]+=212.2 | 95.82 | 98 |
| C₇H₅BBrClO₂ | 6-bromo-5-chlorobenzo[c][1,2]oxaborol-1(3H)-ol | [M-H]-=246.9 | 99.32 | 89.16 |
| C₈H₅BClNO₂ | 5-chloro-1-hydroxy-1,3-dihydrobenzo[c][1,2]oxaborole-6-carbonitrile | [M+H]+=194.1 | 100 | 100 |
| C₈H₉BO₃S | 6-(methylsulfinyl)benzo[c][1,2]oxaborol-1(3H)-ol | [M+H]+=197.2 | 97.68 | 100 |
| C₈H₈BFO₃ | 5-fluoro-7-methoxybenzo[c][1,2]oxaborol-1(3H)-ol | [M+H]+=183.0 | 99.22 | 96.82 |
| C₈H₈BClO₂S | 5-chloro-6-(methylthio)benzo[c][1,2]oxaborol-1(3H)-ol | [M-H]-=213.0 | 98.55 | 97.38 |

FIG. 2C

| Structure | IUPAC Name | MS (m/z) | HPLC purity (220 nm) | HPLC purity (254 nm) |
|---|---|---|---|---|
| C$_8$H$_6$BClF$_2$O$_3$ | 5-chloro-4-(difluoromethoxy)benzo[c][1,2]oxaborol-1(3H)-ol | [M-H]-=233.0 | 99.28 | 100 |
| C$_8$H$_9$BClNO$_2$ | 5-chloro-4-(methylamino)benzo[c][1,2]oxaborol-1(3H)-ol | [M-H]-=196.1 | 98.9 | 99.33 |
| C$_8$H$_8$BClO$_3$S | 5-chloro-6-(methylsulfinyl)benzo[c][1,2]oxaborol-1(3H)-ol | [M+H]+=231.2 | 99.69 | 100 |
| C$_8$H$_8$BClO$_4$S | 5-chloro-6-(methylsulfonyl)benzo[c][1,2]oxaborol-1(3H)-ol | [M+H]+=247.0 | 99.85 | 100 |
| C$_7$H$_5$BBrClO$_2$ | 7-bromo-4-chlorobenzo[c][1,2]oxaborol-1(3H)-ol | [M-H]-=244.8 | 100 | 100 |
| C$_8$H$_8$BClO$_2$S | 5-chloro-7-(methylthio)benzo[c][1,2]oxaborol-1(3H)-ol | [M-H]-=213.1 | 100 | 100 |

FIG. 2D

| Structure | IUPAC Name | MS (m/z) | HPLC purity (220 nm) | HPLC purity (254 nm) |
|---|---|---|---|---|
| C₈H₆BClF₂O₃ | 5-chloro-7-(difluoromethoxy)benzo[c][1,2]oxaborol-1(3H)-ol | [M-H]-=233.1 | 100 | 100 |
| C₁₀H₁₂BClO₃ | 5-chloro-7-propoxybenzo[c][1,2]oxaborol-1(3H)-ol | [M-H]-=225.1 | 100 | 100 |
| C₁₁H₁₅BO₃ | 6-(sec-butoxy)benzo[c][1,2]oxaborol-1(3H)-ol | [M+H]=207.1 | 96.8 | |
| C₈H₆BClF₂O₃ | 5-chloro-6-(difluoromethoxy)benzo[c][1,2]oxaborol-1(3H)-ol | [M-H]-=233.0 | 99.4 | 100 |
| C₁₁H₁₃BO₃ | 6-cyclobutoxybenzo[c][1,2]oxaborol-1(3H)-ol | [M+H]=205.1 | 99.46 | 92.47 |
| C₈H₈BClO₃S | 5-chloro-7-(methylsulfinyl)benzo[c][1,2]oxaborol-1(3H)-ol | [M+H]+=231.1 | 100 | 100 |
| C₉H₁₁BClNO₂ | 6-amino-5-chloro-3,3-dimethylbenzo[c][1,2]oxaborol-1(3H)-ol | [M-H]-=210.1 | 98.01 | 100 |

FIG. 2E

| Structure | IUPAC Name | MS (m/z) | HPLC purity (220 nm) | HPLC purity (254 nm) |
|---|---|---|---|---|
| C₇H₇BO₃ | benzo[c][1,2]oxaborole-1,4(3H)-diol | [M-H]-=149 | 99.89 | 99.74 |
| C₉H₁₁BClNO₂ | 6-amino-7-chloro-3,3-dimethylbenzo[c][1,2]oxaborol-1(3H)-ol | [M-H]-=210.0 | 92.39 | 94.26 |
| C₈H₉BClNO₂ | 6-amino-5-chloro-7-methylbenzo[c][1,2]oxaborol-1(3H)-ol | [M-H]-=196.1 | 99.69 | 100 |
| C₁₀H₁₁BO₃ | 6-cyclopropoxybenzo[c][1,2]oxaborol-1(3H)-ol | [M+H]=191.0 | 99.57 | 95.92 |
| C₉H₁₀BCl₂NO₂ | 5,7-dichloro-6-(dimethylamino)benzo[c][1,2]oxaborol-1(3H)-ol | [M+H]+=246.0 | 86.26 | 94.3 |
| C₁₀H₁₃BClNO₂ | 5-chloro-6-(propylamino)benzo[c][1,2]oxaborol-1(3H)-ol | [M+H]+=226.0 | 97.63 | 100 |
| C₁₀H₁₃BClNO₂ | 5-chloro-6-(isopropylamino)benzo[c][1,2]oxaborol-1(3H)-ol | [M-H]-=223.9 | 98.72 | 98.32 |
| C₁₂H₁₅BClNO₂ | 5-chloro-6-((cyclobutylmethyl)amino)benzo[c][1,2]oxaborol-1(3H)-ol | [M+H]+=252.1 | 98.21 | 98.4 |

FIG. 2F

| Structure | IUPAC Name | MS (m/z) | HPLC purity (220 nm) | HPLC purity (254 nm) |
|---|---|---|---|---|
| C$_8$H$_8$BCl$_2$NO$_2$ | 5,7-dichloro-6-(methylamino)benzo[c][1,2]oxaborol-1(3H)-ol | [M+H]+=231.9 | 100 | 100 |
| C$_{11}$H$_{14}$BCl$_2$NO$_2$ | 5,7-dichloro-6-(diethylamino)benzo[c][1,2]oxaborol-1(3H)-ol | [M+H]+=274.0 | 100 | 100 |
| C$_{11}$H$_{15}$BClNO$_2$ | 6-(butylamino)-5-chlorobenzo[c][1,2]oxaborol-1(3H)-ol | [M-H]-=238.1 | 95.35 | 95.44 |
| C$_9$H$_{10}$BCl$_2$NO$_2$ | 5,7-dichloro-6-(ethylamino)benzo[c][1,2]oxaborol-1(3H)-ol | [M+H]+=246.0 | 98.92 | 99.32 |
| C$_{10}$H$_{12}$BCl$_2$NO$_2$ | 5,7-dichloro-6-(propylamino)benzo[c][1,2]oxaborol-1(3H)-ol | [M+H]+=260.0 | 97.45 | 95.61 |
| C$_{11}$H$_{14}$BCl$_2$NO$_2$ | 6-(butylamino)-5,7-dichlorobenzo[c][1,2]oxaborol-1(3H)-ol | [M+H]+=274.0 | 97.25 | 94.9 |
| C$_{11}$H$_{13}$BClNO$_2$ | 5-chloro-6-(cyclobutylamino)benzo[c][1,2]oxaborol-1(3H)-ol | [M-H]-=236.0 | 98.34 | 100 |
| C$_{12}$H$_{15}$BClNO$_2$ | 5-chloro-6-(cyclopentylamino)benzo[c][1,2]oxaborol-1(3H)-ol | [M-H]-=250.1 | 96.42 | 97.94 |

FIG. 2G

| Structure | IUPAC Name | MS (m/z) | HPLC purity (220 nm) | HPLC purity (254 nm) |
|---|---|---|---|---|
| 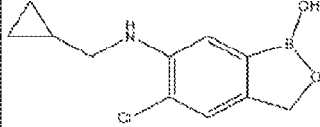 C₁₁H₁₃BClNO₂ | 5-chloro-6-((cyclopropylmethyl)amino)benzo[c][1,2]oxaborol-1(3H)-ol | [M-H]-=236.1 | 95.67 | 96.02 |
| 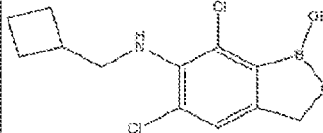 C₁₂H₁₄BCl₂NO₂ | 5,7-dichloro-6-((cyclobutylmethyl)amino)benzo[c][1,2]oxaborol-1(3H)-ol | [M+H]+=286.0 | 98.38 | 97.97 |
| 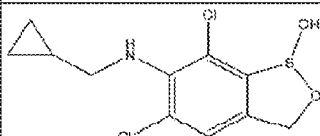 C₁₁H₁₂BCl₂NO₂ | 5,7-dichloro-6-((cyclopropylmethyl)amino)benzo[c][1,2]oxaborol-1(3H)-ol | [M+H]+=272.1 | 100 | 100 |
| 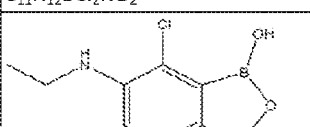 C₉H₁₁BClNO₂ | 7-chloro-6-(ethylamino)benzo[c][1,2]oxaborol-1(3H)-ol | [M+H]+=212.0 | 100 | 100 |
| 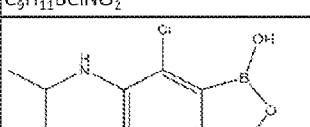 C₁₀H₁₂BCl₂NO₂ | 5,7-dichloro-6-(isopropylamino)benzo[c][1,2]oxaborol-1(3H)-ol | [M+H]+=260.1 | 100 | 100 |
| 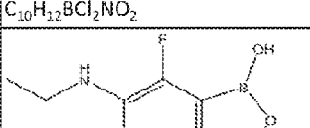 C₉H₁₁BFNO₂ | 6-(ethylamino)-7-fluorobenzo[c][1,2]oxaborol-1(3H)-ol | [M-H]-=194.1 | 97.87 | 94.13 |
| 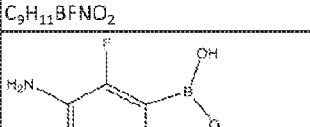 C₇H₆BClFNO₂ | 6-amino-5-chloro-7-fluorobenzo[c][1,2]oxaborol-1(3H)-ol | [M-H]-=200.1 | 100 | 100 |
| 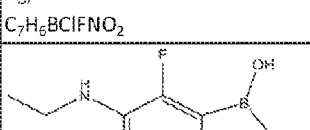 C₉H₁₀BClFNO₂ | 5-chloro-6-(ethylamino)-7-fluorobenzo[c][1,2]oxaborol-1(3H)-ol | [M+H]+=230.1 | 98.76 | 100 |

FIG. 2H

| Structure | IUPAC Name | MS (m/z) | HPLC purity (220 nm) | HPLC purity (254 nm) |
|---|---|---|---|---|
| $C_{10}H_{14}BNO_2$ | 3,3-dimethyl-6-(methylamino)benzo[c][1,2]oxaborol-1(3H)-ol | [M+H]+=192.1 | 98.25 | 100 |
| $C_{10}H_{13}BO_3$ | 6-(hydroxymethyl)-3,3-dimethylbenzo[c][1,2]oxaborol-1(3H)-ol | [M-H]-=191.1 | 99.75 | 100 |

FIG. 21

| Structures | MIC: A. flavus 72hr ppm | MIC: A. solani 72hr ppm | MIC: A. tumefaciens 24hr ppm | MIC: A. tumefaciens 48hr ppm | MIC: B. cinerea 72hr ppm | MIC: E. amylovora 24hr ppm | MIC: E. amylovora 48hr ppm | MIC: E. coli 24hr ppm | MIC: E. coli 48hr ppm | MIC: F. oxysporum 72hr ppm | MIC: M. fijiensis 144hr Agar ppm |
|---|---|---|---|---|---|---|---|---|---|---|---|
| C$_8$H$_8$BFO$_3$ | 1.56 | 101 | 0.39 | 101 | 6.25 | 3.13 | 101 | 6.25 | 201 | 101 | 101 |
| C$_8$H$_8$BClO$_3$ | 0.78 | 101 | 0.78 | 101 | 6.25 | 6.25 | 101 | 12.5 | 201 | 101 | 101 |
| C$_8$H$_8$BClF$_1$O$_3$ | 0.2 | 101 | 1.56 | 101 | 3.13 | 12.5 | 101 | 6.25 | 101 | 101 | 101 |
| C$_9$H$_{10}$BClO$_3$ | 0.2 | 101 | 1.56 | 101 | 0.78 | 6.25 | 101 | 12.5 | 101 | 101 | 101 |
| C$_{10}$H$_{12}$BClO$_3$ | 0.2 | | 6.25 | 101 | 0.78 | 25 | 101 | 25 | 101 | 101 | 101 |

FIG. 3A

| Structures | MIC: M. fijiensis 144hr ppm | MIC: P. capsici 72hr ppm | MIC: R. solani 72hr Agar ppm | MIC: R. solani 72hr ppm | MIC: S. sclerotiorum 72hr ppm | MIC: X. campestris 48hr ppm | MIC: X. campestris 72hr ppm | MIC: C. sublineolum 120 hr Agar ppm | MIC: C. sublineolum 72hr ppm | MIC: P. nodorum 120hr ppm |
|---|---|---|---|---|---|---|---|---|---|---|
| 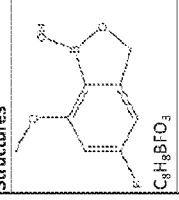 C$_8$H$_8$BF

| Structures | MIC: A. flavus 72hr_ppm | MIC: A. solani 72hr_ppm | MIC: A. tumefaciens 24hr_ppm | MIC: A. tumefaciens 48hr_ppm | MIC: B. cinerea 72hr_ppm | MIC: E. amylovora 24hr_ppm | MIC: E. amylovora 48hr_ppm | MIC: E. coli 24hr_ppm | MIC: E. coli 48hr_ppm | MIC: F. oxysporum 72hr_ppm | MIC: M. fijiensis 144hr Agar_ppm | MIC: M. fijiensis 144hr_ppm |
|---|---|---|---|---|---|---|---|---|---|---|---|---|
| C₇H₈BNO₂ | 101 | | 0.39 | 101 | 25 | 0.78 | 101 | 3.13 | 101 | | 201 | 101 |
| C₇H₆BNO₄ | 3.13 | 101 | 25 | 101 | 3.13 | 101 | 101 | 101 | 101 | 101 | 201 | 1.56 |
| C₉H₉BO₄ | 6.25 | 101 | 6.25 | 101 | 25 | 201 | 201 | 201 | 101 | 101 | 101 | 3.13 |
| C₉H₉BO₄ | 1.56 | 101 | 101 | 201 | 0.78 | 201 | 201 | 101 | 101 | 101 | 101 | 1.56 |
| C₉H₉BO₃ | 201 | 101 | 3.13 | 101 | 50 | 3.13 | 101 | 12.5 | 101 | | 201 | 101 |
| C₈H₈BClO₂ | 3.13 | 101 | 3.13 | 101 | 12.5 | 25 | | 12.5 | 101 | 101 | 101 | 3.13 |
| C₈H₈BClO₂ | 6.25 | 101 | 1.56 | 101 | 3.13 | 101 | 101 | 12.5 | 101 | 101 | 101 | 1.56 |

FIG. 3C

| Structures | MIC: P. capsid 72hr_ppm | MIC: R. solani 72hr Agar_ppm | MIC: R. solani 72hr_ppm | MIC: S. sclerotiorum 72hr_ppm | MIC: X. campestris 48hr_ppm | MIC: X. campestris 72hr_ppm | MIC: C. sublineolum 120 hr Agar_ppm | MIC: C. sublineolum 72hr_ppm | MIC: P. nodorum 120hr_ppm |
|---|---|---|---|---|---|---|---|---|---|
| C₇H₈BNO₂ | | 201 | 100 | | | 101 | 101 | | |
| C₇H₆BNO₄ | 101 | 101 | 50 | 101 | 1.56 | 101 | 201 | 101 | |
| C₉H₉BO₄ | 201 | 101 | 50 | 101 | 101 | 101 | 101 | 6.25 | 1.56 |
| C₉H₉BO₄ | 201 | 101 | 25 | 101 | 101 | 201 | 101 | 6.25 | 6.25 |
| C₈H₉BO₃ | 101 | 201 | 12.5 | 101 | 12.5 | 101 | 101 | 1.56 | 3.13 |
| C₈H₈BClO₂ | | 101 | 6.25 | 101 | 25 | 101 | 201 | 101 | |
| C₈H₈BClO₂ | 201 | 101 | | | 101 | 101 | 101 | 3.13 | 3.13 |
| | | | | | | | 101 | 3.13 | 3.13 |

FIG. 3D

| Structures | MIC: A. flavus 72hr_ppm | MIC: A. solani 72hr_ppm | MIC: A. tumefaciens 24hr_ppm | MIC: A. tumefaciens 48hr_ppm | MIC: B. cinerea 72hr_ppm | MIC: E. amylovora 24hr_ppm | MIC: E. amylovora 48hr_ppm | MIC: E. coli 24hr_ppm | MIC: E. coli 48hr_ppm | MIC: F. oxysporum 72hr_ppm | MIC: M. fijiensis 144hr Agar_ppm | MIC: M. fijiensis 144hr_ppm |
|---|---|---|---|---|---|---|---|---|---|---|---|---|
| C₇H₅BClFO₂ | 0.2 | 101 | 101 | 201 | 1.56 | 101 | 201 | 25 | 101 | 101 | 101 | 0.39 |
| C₉H₈BClO₃ | 3.13 | 101 | 101 | 201 | 25 | 201 | 201 | 201 | 101 | 101 | 101 | 3.13 |
| C₉H₉BO₃ | 12.5 | 101 | 1.56 | 101 | 25 | 6.25 | 101 | 6.25 | 101 | 201 | 101 | 25 |
| C₈H₈BFO₂ | 12.5 | 101 | 0.39 | 101 | 12.5 | 6.25 | 101 | 6.25 | 101 | 101 | 101 | 6.25 |
| C₇H₅BClFO₂ | 0.2 | 101 | 0.78 | 101 | 1.56 | 0.39 | 101 | 25 | 101 | 101 | 101 | 0.78 |
| C₇H₇BClNO₂ | 101 | 101 | 0.39 | 101 | 6.25 | 101 | 101 | 0.39 | 101 | 101 | 101 | 101 |

FIG. 3E

| Structures | MIC: A. flavus 72hr_ppm | MIC: A. solani 72hr_ppm | MIC: A. tumefaciens 24hr_ppm | MIC: A. tumefaciens 48hr_ppm | MIC: B. cinerea 72hr_ppm | MIC: E. amylovora 24hr_ppm | MIC: E. amylovora 48hr_ppm | MIC: E. coli 24hr_ppm | MIC: E. coli 48hr_ppm | MIC: F. oxysporum 72hr_ppm | MIC: M. fijiensis 144hr Agar_ppm | MIC: M. fijiensis 144hr_ppm |
|---|---|---|---|---|---|---|---|---|---|---|---|---|
| C₈H₉BO₃ | 201 | | 0.78 | 101 | 50 | 3.13 | 101 | 6.25 | 101 | | 201 | 201 |
| C₈H₇BO₃ | 101 | | 1.56 | 101 | 25 | 201 | 201 | 101 | 201 | | 101 | 101 |
| C₈H₇BO₃ | 101 | | 3.13 | 101 | 6.25 | 3.13 | 101 | 12.5 | 101 | | 101 | 101 |
| C₈H₁₀BNO₂ | 101 | 101 | 1.56 | 101 | 100 | 0.39 | 101 | 1.56 | 101 | | 201 | 201 |
| C₇H₅BClFO₂ | 0.2 | 101 | 0.78 | 101 | 0.39 | 3.13 | 101 | 6.25 | 101 | 101 | 101 | 0.2 |
| C₇H₅BClNO₄ | 3.13 | | 25 | 101 | 25 | 25 | 101 | 25 | 101 | 101 | 101 | 3.13 |
| C₇H₆BClO₂ | 0.39 | | 1.56 | 101 | 0.2 | 12.5 | 101 | 25 | 101 | | 201 | 0.78 |

FIG. 3G

| Structures | MIC: P. capsici 72hr_ppm | MIC: R. solani 72hr Agar_ppm | MIC: R. solani 72hr_ppm | MIC: S. sclerotiorum 72hr_ppm | MIC: X. campestris 48hr_ppm | MIC: X. campestris 72hr_ppm | MIC: C. sublineolum 120 hr Agar_ppm | MIC: C. sublineolum 72hr _ppm | MIC: P. nodorum 120hr_ppm |
|---|---|---|---|---|---|---|---|---|---|
|  $C_8H_9BO_3$ | | 201 | 201 | | 6.25 | 101 | 201 | 101 | |
|  $C_8H_7BO_3$ | | 201 | 100 | | 101 | 101 | 201 | 101 | |
|  $C_8H_7BO_3$ | | 201 | 100 | | 12.5 | 101 | 101 | 101 | |
|  $C_8H_{10}BNO_2$ | | 201 | 201 | | 1.56 | 101 | 201 | 101 | |
|  $C_7H_5BClFO_2$ | 101 | 101 | 1.56 | 101 | 25 | 101 | 101 | 0.39 | 1.56 |
|  $C_7H_5BClNO_4$ | 101 | 101 | 25 | 101 | 25 | 101 | 201 | 3.13 | 12.5 |
|  $C_7H_6BClO_2$ | | 101 | 0.39 | | 101 | 101 | 101 | 0.39 | |

FIG. 3H

| Structures | MIC: A. flavus 72hr_ppm | MIC: A. solani 72hr_ppm | MIC: A. tumefaciens 24hr_ppm | MIC: A. tumefaciens 48hr_ppm | MIC: B. cinerea 72hr_ppm | MIC: E. amylovora 24hr_ppm | MIC: E. amylovora 48hr_ppm | MIC: E. coli 24hr_ppm | MIC: E. coli 48hr_ppm | MIC: F. oxysporum 72hr_ppm | MIC: M. fijiensis 144hr Agar_ppm | MIC: M. fijiensis 144hr_ppm |
|---|---|---|---|---|---|---|---|---|---|---|---|---|
| C9H8BClO4 | 6.25 | 101 | 201 | 201 | 25 | 201 | 201 | 201 | 201 | 201 | | 3.13 |
| C8H8BClO2 | 0.78 | 101 | 201 | 201 | 6.25 | 201 | 201 | 201 | 201 | 101 | 101 | 1.56 |
| C8H8BClO3 | 101 | | 3.13 | 101 | 12.5 | 12.5 | 12.5 | 12.5 | 101 | | 101 | 101 |
| C8H9BO3 | 101 | | 12.5 | 101 | 6.25 | 6.25 | 12.5 | 12.5 | 101 | | 101 | 101 |
| C8H6BNO3 | 201 | | 201 | 201 | 25 | 101 | 101 | 101 | 101 | | 101 | 101 |
| C10H11BO4 | 101 | | 201 | 101 | 25 | 201 | 201 | 201 | 201 | | 101 | 101 |

FIG. 3I

| Structures | MIC: P. capsici 72hr_ppm | MIC: R. solani 72hr Agar_ppm | MIC: R. solani 72hr_ppm | MIC: S. sclerotiorum 72hr_ppm | MIC: X. campestris 48hr_ppm | MIC: X. campestris 72hr_ppm | MIC: C. sublineolum 120 hr Agar_ppm | MIC: C. sublineolum 72hr_ppm | MIC: P. nodorum 120hr_ppm |
|---|---|---|---|---|---|---|---|---|---|
| 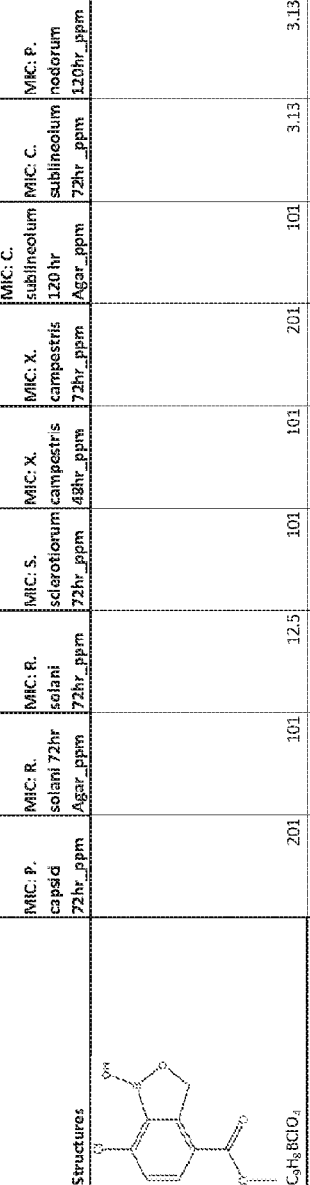 C9H8BClO3 | 201 | | 101 | | | 201 | | | |
| 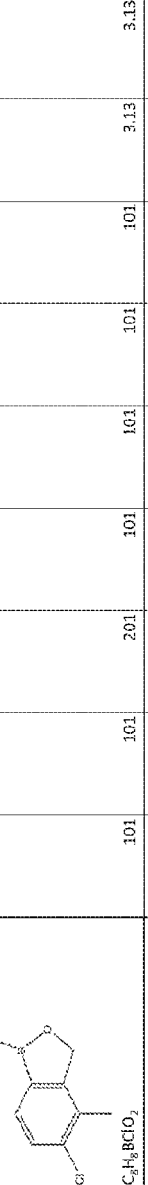 C8H8BClO2 | 101 | 101 | 201 | 101 | 101 | 201 | 101 | 3.13 | 3.13 |
| 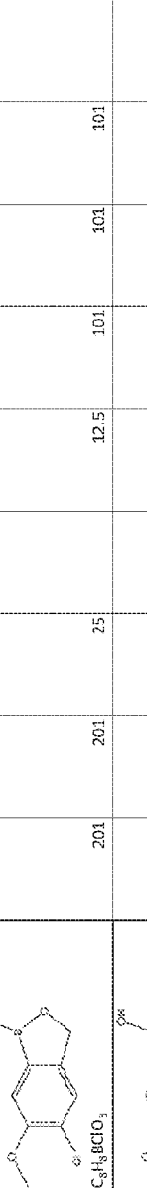 C8H8BClO3 | 201 | 201 | 25 | 101 | 12.5 | 101 | 101 | 3.13 | 3.13 |
| 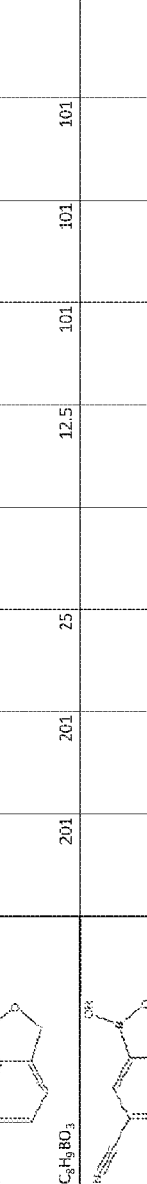 C8H9BO3 | 201 | 201 | 25 | | 12.5 | 101 | 101 | 101 | |
| 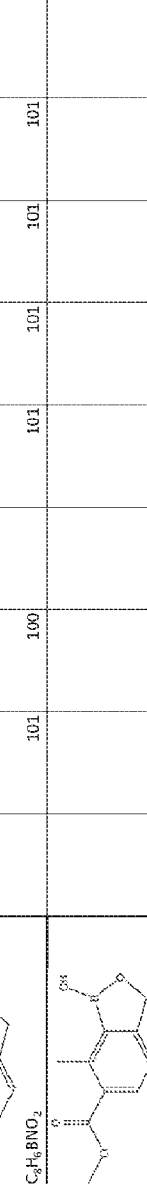 C8H6BNO2 | 101 | 101 | 100 | | 101 | 101 | 101 | 101 | |
| 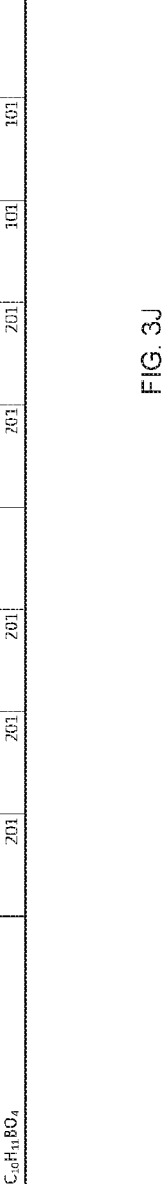 C10H11BO4 | 201 | 201 | 201 | | 201 | 201 | 101 | 101 | |
FIG. 3J

| Structures | MIC: A. flavus 72hr_ppm | MIC: A. solani 72hr_ppm | MIC: A. tumefaciens 24hr_ppm | MIC: A. tumefaciens 48hr_ppm | MIC: B. cinerea 72hr_ppm | MIC: E. amylovora 24hr_ppm | MIC: E. amylovora 48hr_ppm | MIC: E. coli 24hr_ppm | MIC: E. coli 48hr_ppm | MIC: F. oxysporum 72hr_ppm | MIC: M. fijiensis 144hr Agar_ppm | MIC: M. fijiensis 144hr_ppm |
|---|---|---|---|---|---|---|---|---|---|---|---|---|
| C9H8BClO4 | 201 | | 201 | 201 | 100 | 25 | 201 | 25 | 101 | | 101 | 101 |
| C8H8BClO2S | 3.13 | 101 | 201 | 101 | 12.5 | 201 | 201 | 201 | 201 | 101 | 101 | 0.39 |
| C7H8BClO2S | 201 | | 201 | 101 | 100 | 201 | 201 | 201 | 201 | | 101 | 201 |
| C7H8BClNO2 | 201 | | 201 | 101 | 100 | 201 | 201 | 201 | 201 | | 201 | 201 |
| C8H8BClO2S | 6.25 | 101 | 201 | 101 | 12.5 | 101 | 101 | 12.5 | 101 | 101 | 101 | 0.78 |
| C7H6BClO3 | 101 | | 0.78 | 101 | 25 | 1.56 | 101 | 3.13 | 101 | | 101 | 201 |

FIG. 3K

| Structures | MIC: P. capsici 72hr_ppm | MIC: R. solani 72hr Agar_ppm | MIC: R. solani 72hr_ppm | MIC: S. sclerotiorum 72hr_ppm | MIC: X. campestris 48hr_ppm | MIC: X. campestris 72hr_ppm | MIC: C. sublineolum 120 hr Agar_ppm | MIC: C. sublineolum 72hr_ppm | MIC: P. nodorum 120hr_ppm |
|---|---|---|---|---|---|---|---|---|---|
| C₉H₈BClO₃ |  | 201 | 50 |  | 25 | 101 | 101 | 101 |  |
| C₈H₈BClO₂S |  | 101 | 201 | 101 | 101 | 101 | 101 | 3.13 | 3.13 |
| C₈H₈BClNO₃ |  | 201 | 100 |  | 101 | 101 | 101 |  |  |
| C₉H₈BClO₃ | 101 | 201 | 201 | 101 | 101 | 201 | 201 | 101 |  |
| C₉H₈BClO₃ |  | 201 | 12.5 |  | 25 | 101 | 101 | 101 |  |
| C₈H₈BClO₃ |  | 201 | 100 |  | 6.25 | 101 | 201 | 3.13 | 12.5 |
| C₇H₆BClO₃ | 201 | 201 |  |  |  | 101 | 201 | 101 |  |

FIG. 3L

| Structures | MIC: A. flavus 72hr_ppm | MIC: A. solani 72hr_ppm | MIC: A. tumefaciens 24hr_ppm | MIC: A. tumefaciens 48hr_ppm | MIC: B. cinerea 72hr_ppm | MIC: E. amylovora 24hr_ppm | MIC: E. amylovora 48hr_ppm | MIC: E. coli 24hr_ppm | MIC: E. coli 48hr_ppm | MIC: F. oxysporum 72hr_ppm | MIC: M. fijiensis 144hr Agar_ppm | MIC: M. fijiensis 144hr_ppm |
|---|---|---|---|---|---|---|---|---|---|---|---|---|
| C9H9BClNO2 | 101 | | 0.78 | 101 | 12.5 | 3.13 | 101 | | | | 101 | 101 |
| C9H11BClNO2 | 201 | 101 | 101 | 101 | 100 | 201 | 201 | 6.25 | 101 | | 101 | 201 |
| C9H11BClNO2 | 0.2 | | 0.78 | 101 | 0.39 | 1.56 | 201 | 12.5 | 101 | 101 | 101 | 12.5 |
| C7H6BClO3 | 201 | | 101 | 201 | 100 | 201 | 201 | 12.5 | 201 | | 101 | 201 |
| C9H11BClNO2 | 101 | 101 | 201 | 201 | 50 | 201 | 201 | 201 | 201 | | 101 | 101 |
| C7H6BClNO2 | 12.5 | | 0.39 | 101 | 3.13 | 1.56 | 101 | 201 | 101 | 101 | 101 | 6.25 |
| C9H11BClNO2 | 0.39 | 101 | 3.13 | 101 | 0.78 | 25 | 201 | 101 | 101 | 101 | 101 | 1.56 |

FIG. 3M

| Structures | MIC: P. capsici 72hr_ppm | MIC: R. solani 72hr Agar_ppm | MIC: R. solani 72hr_ppm | MIC: S. sclerotiorum 72hr_ppm | MIC: X. campestris 48hr_ppm | MIC: X. campestris 72hr_ppm | MIC: C. sublineolum 120 hr Agar_ppm | MIC: C. sublineolum 72hr_ppm | MIC: P. nodorum 120hr_ppm |
|---|---|---|---|---|---|---|---|---|---|
| C₈H₉BClNO₂ | | 201 | 25 | | 1.56 | 101 | 101 | 101 | |
| C₉H₁₁BClNO₂ | | 201 | 201 | | 6.25 | 101 | 101 | 101 | |
| C₇H₇BO₂ | 101 | 101 | 1.56 | 101 | 6.25 | 101 | 101 | 3.13 | 3.13 |
| C₉H₆BClO₃ | | 201 | 100 | | 101 | 101 | 201 | 101 | |
| C₉H₁₁BClNO₂ | 101 | 101 | 201 | 101 | 101 | 201 | 201 | 201 | |
| C₇H₇BClNO₂ | | 101 | 25 | | 6.25 | 101 | 101 | 6.25 | 3.13 |
| C₉H₁₁BClNO₂ | 101 | 101 | 0.78 | 101 | 25 | 101 | 201 | 6.25 | 1.56 |

FIG. 3N

| Structures | MIC: A. flavus 72hr_ppm | MIC: A. solani 72hr_ppm | MIC: A. tumefaciens 24hr_ppm | MIC: A. tumefaciens 48hr_ppm | MIC: B. cinerea 72hr_ppm | MIC: E. amylovora 24hr_ppm | MIC: E. amylovora 48hr_ppm | MIC: E. coli 24hr_ppm | MIC: E. coli 48hr_ppm | MIC: F. oxysporum 72hr_ppm | MIC: M. fijiensis 144hr Agar_ppm | MIC: M. fijiensis 144hr_ppm |
|---|---|---|---|---|---|---|---|---|---|---|---|---|
| C7H5BBrClO2 | 3.13 | 101 | 12.5 | 101 | 0.78 | 101 | 201 | 101 | 101 | | | 0.39 |
| C9H10BClO3 | 0.2 | | 101 | 201 | 0.78 | 101 | 101 | 101 | 101 | 101 | 101 | 0.78 |
| C10H12BClO3 | 101 | 101 | 101 | 101 | 12.5 | 201 | 201 | 201 | 201 | | 101 | 101 |
| C7H6BFO2 | 0.2 | | 0.39 | 101 | 0.01 | 1.56 | 101 | 12.5 | 101 | 101 | 101 | 0.78 |
| C9H8BNO2 | 101 | | 0.78 | 101 | 100 | 201 | 201 | 201 | 201 | | 101 | 101 |
| C9H9BO2 | 0.39 | | 6.25 | 101 | 0.78 | 12.5 | 101 | 101 | 201 | 101 | 101 | 3.13 |
| C8H5BClNO2 | 101 | | 25 | 101 | 100 | 201 | 201 | 201 | 201 | | 101 | 101 |

FIG. 30

| Structures | MIC: P. capsid 72hr_ppm | MIC: R. solani 72hr Agar_ppm | MIC: R. solani 72hr_ppm | MIC: S. sclerotiorum 72hr_ppm | MIC: X. campestris 48hr_ppm | MIC: X. campestris 72hr_ppm | MIC: C. sublineolum 120 hr Agar_ppm | MIC: C. sublineolum 72hr_ppm | MIC: P. nodorum 120hr_ppm |
|---|---|---|---|---|---|---|---|---|---|
| 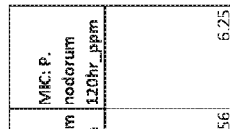 $C_7H_5BBrClO_2$ | 201 | 101 | 3.13 | 101 | 101 | 101 | 101 | 1.56 | 6.25 |
| 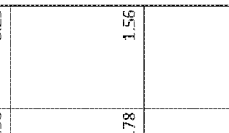 $C_9H_{10}BClO_3$ | 201 | 101 | 25 | 101 | 101 | 101 | 101 | 0.78 | 1.56 |
|  $C_{10}H_{12}BClO_3$ | | 201 | 201 | 101 | 101 | 101 | 201 | 101 | |
| 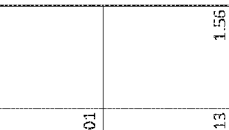 $C_7H_6BFO_2$ | 101 | 101 | 0.39 | 101 | 6.25 | 101 | 101 | 0.78 | 0.39 |
| 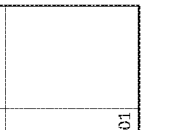 $C_8H_6BNO_2$ | 101 | 201 | 201 | | 101 | 101 | 201 | 101 | |
|  $C_8H_9BO_2$ | | 101 | 3.13 | | 101 | 101 | 101 | 3.13 | 1.56 |
|  $C_8H_5BClNO_2$ | | 201 | 201 | | 101 | 101 | 101 | 101 | |
FIG. 3P

| Structures | MIC: A. flavus 72hr_ppm | MIC: A. solani 72hr_ppm | MIC: A. tumefaciens 24hr_ppm | MIC: A. tumefaciens 48hr_ppm | MIC: B. cinerea 72hr_ppm | MIC: E. amylovora 24hr_ppm | MIC: E. amylovora 48hr_ppm | MIC: E. coli 24hr_ppm | MIC: E. coli 48hr_ppm | MIC: F. oxysporum 72hr_ppm | MIC: M. fijiensis 144hr Agar_ppm | MIC: M. fijiensis 144hr_ppm |
|---|---|---|---|---|---|---|---|---|---|---|---|---|
| 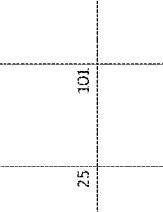 C8H9BO3S | 1.56 | 101 | 12.5 | 101 | 6.25 | 101 | 101 | 25 | 101 | 101 | 101 | 1.56 |
| 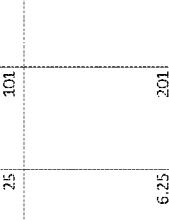 C8H9BO3S | 201 | 101 | 12.5 | 101 | 201 | 201 | 101 | 25 | 101 | 101 | 201 | 201 |
| 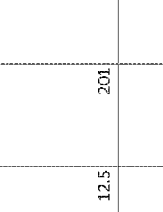 C8H8BFO3 | 1.56 | 101 | 0.39 | 101 | 6.25 | 3.13 | 101 | 6.25 | 201 | 101 | 101 | 1.56 |
| 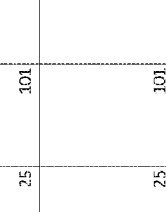 C8H8BClO3 | 0.78 | 101 | 0.78 | 101 | 6.25 | 6.25 | 101 | 12.5 | 201 | 101 | 101 | 0.78 |
|  C7H5BClO2 | 3.13 | 101 | 25 | 201 | 50 | 101 | 101 | 25 | 101 | 101 | 101 | 0.39 |
|  C8H8BClO2S | 101 | 101 | 6.25 | 101 | 50 | 12.5 | 101 | 25 | 101 | 101 | 101 | 101 |
FIG. 3Q

| Structures | MIC: P. capsici 72hr_ppm | MIC: R. solani 72hr Agar_ppm | MIC: R. solani 72hr_ppm | MIC: S. sclerotiorum 72hr_ppm | MIC: X. campestris 48hr_ppm | MIC: X. campestris 72hr_ppm | MIC: C. sublineolum 120 hr Agar_ppm | MIC: C. sublineolum 72hr _ppm | MIC: P. nodorum 120hr_ppm |
|---|---|---|---|---|---|---|---|---|---|
|  $C_8H_9BO_2S$ | 101 | 101 | 12.5 | 101 | 25 | 101 | 101 | 3.13 | 3.13 |
|  $C_8H_9BO_3S$ | | 201 | 201 | | 101 | 101 | 201 | 201 | |
|  $C_8H_8BFO_3$ | 101 | 101 | 3.13 | 101 | 3.13 | 101 | 101 | 6.25 | |
|  $C_8H_8BClO_3$ | 101 | 101 | 1.56 | 101 | 12.5 | 101 | 101 | 1.56 | 0.78 |
|  $C_7H_5BClIO_2$ | 101 | 101 | 12.5 | 101 | 101 | 101 | 101 | 0.78 | 1.56 |
|  $C_8H_8BClO_2S$ | 201 | 101 | 12.5 | | 25 | 101 | 101 | 101 | 201 |

FIG. 3R

| Structures | MIC: A. flavus 72hr_ppm | MIC: A. solani 72hr_ppm | MIC: A. tumefaciens 24hr_ppm | MIC: A. tumefaciens 48hr_ppm | MIC: B. cinerea 72hr_ppm | MIC: E. amylovora 24hr_ppm | MIC: E. amylovora 48hr_ppm | MIC: E. coli 24hr_ppm | MIC: E. coli 48hr_ppm | MIC: F. oxysporum 72hr_ppm | MIC: M. fijiensis 144hr Agar_ppm | MIC: M. fijiensis 144hr_ppm |
|---|---|---|---|---|---|---|---|---|---|---|---|---|
|  C₃H₆BClF₂O₃ | 3.13 | 101 | 201 | 201 | 50 | 201 | 201 | 201 | 201 | 101 | 101 | 0.2 |
|  C₃H₉BClNO₂ | 201 | | 201 | 201 | 100 | 201 | 201 | 201 | 201 | | 101 | 101 |
| 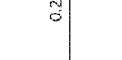 C₃H₈BClO₃S | 201 | | 201 | 201 | 201 | 201 | 201 | 25 | 101 | | 201 | 201 |
|  C₃H₈BClO₃ | 201 | | 0.39 | 101 | 201 | 3.13 | 201 | 101 | 201 | | 101 | 201 |
|  C₇H₅BBrClO₂ | 1.56 | 101 | 201 | 201 | 12.5 | 201 | 201 | 201 | 201 | 101 | 101 | 0.78 |
|  C₃H₁₁BO₂ | 0.78 | 101 | 25 | 201 | 12.5 | 201 | 201 | 101 | 101 | 101 | 101 | 12.5 |
FIG. 3S

| Structures | MIC: A. flavus 72hr_ppm | MIC: A. solani 72hr_ppm | MIC: A. tumefaciens 24hr_ppm | MIC: A. tumefaciens 48hr_ppm | MIC: B. cinerea 72hr_ppm | MIC: E. amylovora 24hr_ppm | MIC: E. amylovora 48hr_ppm | MIC: E. coli 24hr_ppm | MIC: E. coli 48hr_ppm | MIC: F. oxysporum 72hr_ppm | MIC: M. fijiensis 144hr Agar_ppm | MIC: M. fijiensis 144hr_ppm |
|---|---|---|---|---|---|---|---|---|---|---|---|---|
| C$_{10}$H$_{13}$BO$_3$ | 101 | | | | 100 | | | | | | | 101 |
| C$_8$H$_8$BClO$_2$S | 3.13 | 101 | 6.25 | 201 | 101 | 25 | 101 | 25 | 101 | 101 | 101 | 0.78 |
| C$_{11}$H$_{15}$BO$_3$ | 12.5 | 101 | 201 | 101 | 100 | 201 | 201 | 101 | 101 | 201 | 101 | 6.25 |
| C$_{10}$H$_{13}$BO$_3$ | 1.56 | 101 | 201 | 101 | 25 | 201 | 201 | 201 | 201 | 201 | 101 | 12.5 |
| C$_8$H$_6$BClF$_2$O$_3$ | 0.2 | 101 | 1.56 | 101 | 3.13 | 12.5 | 101 | 6.25 | 101 | 101 | 101 | 0.78 |
| C$_9$H$_{10}$BClO$_3$ | 0.2 | 101 | 1.56 | 101 | 0.78 | 6.25 | 101 | 12.5 | 101 | 101 | 101 | 0.39 |

FIG. 3U

| Structures | MIC: P. capsici 72hr_ppm | MIC: R. solani 72hr Agar_ppm | MIC: R. solani 72hr_ppm | MIC: S. sclerotiorum 72hr_ppm | MIC: X. campestris 48hr_ppm | MIC: X. campestris 72hr_ppm | MIC: C. sublineolum 120 hr Agar_ppm | MIC: C. sublineolum 72hr _ppm | MIC: P. nodorum 120hr_ppm |
|---|---|---|---|---|---|---|---|---|---|
|  $C_{10}H_{13}BO_3$ | | 201 | 50 | | 101 | 101 | 201 | 101 | |
|  $C_8H_8BClO_2S$ | 101 | 101 | 25 | 101 | 12.5 | 101 | 101 | 0.78 | 3.13 |
|  $C_{11}H_{15}BO_3$ | 201 | 101 | 25 | 101 | 101 | 101 | 101 | 6.25 | 6.25 |
|  $C_{10}H_{13}BO_3$ | 201 | 101 | 25 | 101 | 201 | 201 | 201 | 25 | 12.5 |
|  $C_8H_6BClF_2O_3$ | 101 | 101 | 3.13 | 101 | 6.25 | 101 | 101 | 0.78 | 1.56 |
|  $C_9H_{10}BClO_3$ | 101 | 101 | 0.05 | 101 | 6.25 | 101 | 101 | 0.2 | 0.2 |

FIG. 3V

| Structures | MIC: A. flavus 72hr_ppm | MIC: A. solani 72hr_ppm | MIC: A. tumefaciens 24hr_ppm | MIC: A. tumefaciens 48hr_ppm | MIC: B. cinerea 72hr_ppm | MIC: E. amylovora 24hr_ppm | MIC: E. amylovora 48hr_ppm | MIC: E. coli 24hr_ppm | MIC: E. coli 48hr_ppm | MIC: F. oxysporum 72hr_ppm | MIC: M. fijiensis 144hr Agar_ppm | MIC: M. fijiensis 144hr_ppm |
|---|---|---|---|---|---|---|---|---|---|---|---|---|
| $C_{10}H_{12}BClO_3$ | 0.2 | 101 | 6.25 | 101 | 0.78 | 25 | 101 | 101 | 101 | 101 | 101 | 0.39 |
| $C_{11}H_{15}BO_3$ | 3.13 | 101 | 201 | 201 | 25 | 201 | 201 | 201 | 201 | 201 | 101 | 6.25 |
| $C_9H_6BClF_2O_3$ | 1.56 | 101 | 101 | 101 | 50 | 201 | 201 | 101 | 101 | 101 | 101 | 0.78 |
| $C_{11}H_{13}BO_3$ | 0.78 | 101 | 201 | 201 | 50 | 101 | 101 | 201 | 201 | 201 | 101 | 6.25 |
| $C_9H_8BClO_5S$ | 201 | | 101 | 101 | 101 | 101 | 101 | 101 | 101 | | 101 | 101 |
| $C_9H_{10}BNO_4$ | 201 | | 201 | 201 | 101 | 201 | 201 | 201 | 201 | | 101 | 201 |

FIG. 3W

| Structures | MIC: P. capsici 72hr_ppm | MIC: R. solani 72hr Agar_ppm | MIC: R. solani 72hr_ppm | MIC: S. sclerotiorum 72hr_ppm | MIC: X. campestris 48hr_ppm | MIC: X. campestris 72hr_ppm | MIC: C. sublineolum 120 hr Agar_ppm | MIC: C. sublineolum 72hr_ppm | MIC: P. nodorum 120hr_ppm |
|---|---|---|---|---|---|---|---|---|---|
|  C$_{10}$H$_{12}$BClO$_3$ | 101 | 101 | 0.05 | | 25 | | | 0.2 | 0.2 |
|  C$_{11}$H$_{15}$BO$_3$ | 201 | 101 | 50 | 101 | 201 | 201 | 101 | 6.25 | 1.56 |
|  C$_9$H$_6$BClF$_2$O$_3$ | 201 | 101 | 25 | 101 | 201 | 201 | 101 | 1.56 | 1.56 |
|  C$_{11}$H$_{13}$BO$_3$ | 201 | 101 | 50 | 101 | | | 101 | 6.25 | 1.56 |
| 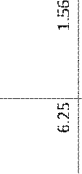 C$_8$H$_8$BClO$_3$S | | 201 | 201 | | | | 201 | 101 | |
|  C$_9$H$_{10}$BNO$_3$ | | 201 | 100 | | | | 201 | 101 | |
FIG. 3X

| Structures | MIC: A. flavus 72hr_ppm | MIC: A. solani 72hr_ppm | MIC: A. tumefaciens 24hr_ppm | MIC: A. tumefaciens 48hr_ppm | MIC: B. cinerea 72hr_ppm | MIC: E. amylovora 24hr_ppm | MIC: E. amylovora 48hr_ppm | MIC: E. coli 24hr_ppm | MIC: E. coli 48hr_ppm | MIC: F. oxysporum 72hr_ppm | MIC: M. fijiensis 144hr Agar_ppm | MIC: M. fijiensis 144hr_ppm |
|---|---|---|---|---|---|---|---|---|---|---|---|---|
| $C_9H_9BClNO_3$ | 201 | | 201 | 201 | 100 | 201 | 201 | 201 | 201 | | 101 | 101 |
| $C_9H_{11}BClNO_2$ | 201 | | 201 | 201 | 201 | 201 | 201 | 201 | 201 | | 201 | 201 |
| $C_8H_8BNO_4$ | 6.25 | 101 | 101 | 201 | 50 | 101 | 201 | 101 | 201 | 101 | 101 | 0.78 |
| $C_9H_{11}BClNO_2$ | 201 | | 201 | 201 | 201 | 201 | 201 | 201 | 201 | | 101 | 201 |
| $C_8H_8BClNO_2$ | 25 | 101 | | | 201 | | | | | 101 | 101 | 6.25 |
| $C_{10}H_{11}BO_3$ | 101 | 201 | | | 1.56 | | | | | 201 | 101 | 101 |

FIG. 3Y

| Structures | MIC: P. capsici 72hr_ppm | MIC: R. solani 72hr Agar_ppm | MIC: R. solani 72hr_ppm | MIC: S. sclerotiorum 72hr_ppm | MIC: X. campestris 48hr_ppm | MIC: X. campestris 72hr_ppm | MIC: C. sublineolum 120 hr Agar_ppm | MIC: C. sublineolum 72hr_ppm | MIC: P. nodorum 120hr_ppm |
|---|---|---|---|---|---|---|---|---|---|
| $C_9H_9BClNO_4$ | | 101 | 100 | | | | 101 | 101 | |
| $C_9H_{11}BClNO_2$ | | 201 | 201 | | | | 201 | 101 | |
| $C_8H_8BNO_4$ | 101 | 101 | 25 | 101 | | | 101 | 6.25 | |
| $C_9H_{11}BClNO_2$ | | 201 | 201 | 101 | | | 201 | 201 | |
| $C_8H_9BClNO_2$ | 101 | 101 | 12.5 | 201 | | | 101 | 6.25 | |
| $C_{10}H_{11}BO_3$ | 201 | 101 | | | | | 101 | 101 | |

FIG. 3Z

| Structures | MIC: A. flavus 72hr_ppm | MIC: A. solani 72hr_ppm | MIC: A. tumefaciens 24hr_ppm | MIC: A. tumefaciens 48hr_ppm | MIC: B. cinerea 72hr_ppm | MIC: E. amylovora 24hr_ppm | MIC: E. amylovora 48hr_ppm | MIC: E. coli 24hr_ppm | MIC: E. coli 48hr_ppm | MIC: F. oxysporum 72hr_ppm | MIC: M. fijiensis 144hr Agar_ppm | MIC: M. fijiensis 144hr_ppm |
|---|---|---|---|---|---|---|---|---|---|---|---|---|
| C₉H₁₀BCl₂NO₂ | 101 | | | | 25 | | | | | | | 0.39 |
| C₁₀H₁₃BClNO₂ | 101 | | | | 101 | | | | | 25 | | 1.56 |
| C₁₀H₁₃BClNO₂ | 12.5 | | | | 12.5 | | | | | | | 0.78 |
| C₁₂H₁₃BClNO₂ | 201 | | | | 201 | | | | | | | 1.56 |
| C₉H₈BCl₂NO₂ | 101 | | | | 201 | | | | | | | 0.78 |
| C₁₁H₁₄BCl₂NO₂ | 201 | | | | 201 | | | | | | | 3.13 |
| C₁₁H₁₅BClNO₂ | 101 | | | | 201 | | | | | | | 1.56 |

FIG. 3AA

| Structures | MIC: P. capsid 72hr_ppm | MIC: R. solani 72hr Agar_ppm | MIC: R. solani 72hr_ppm | MIC: S. sclerotiorum 72hr_ppm | MIC: X. campestris 48hr_ppm | MIC: X. campestris 72hr_ppm | MIC: C. sublineolum 120 hr Agar_ppm | MIC: C. sublineolum 72hr_ppm | MIC: P. nodorum 120hr_ppm |
|---|---|---|---|---|---|---|---|---|---|
| C$_9$H$_{10}$BCl$_2$NO$_2$ | 201 | | 6.25 | 6.25 | | | | 6.25 | |
| C$_{10}$H$_{13}$BClNO$_2$ | | | 0.78 | | | | | 12.5 | |
| C$_{10}$H$_{13}$BClNO$_2$ | 201 | | 6.25 | 6.25 | | | | 25 | |
| C$_{12}$H$_{15}$BClNO$_2$ | | | 1.56 | | | | | 101 | |
| C$_8$H$_8$BCl$_2$NO$_2$ | | | 25 | | | | | 12.5 | |
| C$_{13}$H$_{18}$BCl$_2$NO$_2$ | | | 201 | | | | | 101 | |
| C$_{11}$H$_{15}$BClNO$_2$ | | | 3.13 | | | | | 25 | |

FIG. 3BB

| Structures | MIC: A. flavus 72hr_ppm | MIC: A. solani 72hr_ppm | MIC: A. tumefaciens 24hr_ppm | MIC: A. tumefaciens 48hr_ppm | MIC: B. cinerea 72hr_ppm | MIC: E. amylovora 24hr_ppm | MIC: E. amylovora 48hr_ppm | MIC: E. coli 24hr_ppm | MIC: E. coli 48hr_ppm | MIC: F. oxysporum 72hr_ppm | MIC: M. fijiensis 144hr Agar_ppm | MIC: M. fijiensis 144hr_ppm |
|---|---|---|---|---|---|---|---|---|---|---|---|---|
| $C_9H_{10}BCl_2NO_2$ | 101 | | | | 25 | | | | | | | 0.78 |
| $C_{10}H_{12}BCl_2NO_2$ | 101 | | | | 25 | | | | | | | 0.39 |
| $C_{11}H_{14}BCl_2NO_2$ | 12.5 | | | | 25 | | | | | | | 0.39 |
| $C_{11}H_{13}BClNO_2$ | 12.5 | | | | 101 | | | | | | | 0.39 |
| $C_{12}H_{15}BClNO_2$ | 12.5 | | | | 101 | | | | | | | 0.2 |
| $C_{11}H_{13}BClNO_2$ | 101 | | | | 201 | | | | | | | 1.56 |
| $C_{12}H_{14}BCl_2NO_2$ | 12.5 | | | | 101 | | | | | | | 3.13 |

FIG. 3CC

| Structures | MIC: P. capsid 72hr_ppm | MIC: R. solani 72hr Agar_ppm | MIC: R. solani 72hr_ppm | MIC: S. sclerotiorum 72hr_ppm | MIC: X. campestris 48hr_ppm | MIC: X. campestris 72hr_ppm | MIC: C. sublineolum 120 hr Agar_ppm | MIC: C. sublineolum 72hr_ppm | MIC: P. nodorum 120hr_ppm |
|---|---|---|---|---|---|---|---|---|---|
| $C_9H_{10}BCl_2NO_2$ | | | 25 | | | | | 12.5 | |
| $C_{10}H_{12}BCl_2NO_2$ | | | 12.5 | | | | | 25 | |
| $C_{11}H_{14}BCl_2NO_2$ | | | 12.5 | | | | | 101 | |
| $C_{11}H_{13}BClNO_2$ | | | 0.78 | | | | | 3.13 | |
| $C_{11}H_{14}BClNO_2$ | | | 0.78 | | | | | 25 | |
| $C_{12}H_{15}BClNO_2$ | | | 0.78 | | | | | 12.5 | |
| $C_{12}H_{14}BClNO_2$ | | | 12.5 | | | | | 3.13 | |

FIG. 3DD

| Structures | MIC: A. flavus 72hr_ppm | MIC: A. solani 72hr_ppm | MIC: A. tumefaciens 24hr_ppm | MIC: A. tumefaciens 48hr_ppm | MIC: B. cinerea 72hr_ppm | MIC: E. amylovora 24hr_ppm | MIC: E. amylovora 48hr_ppm | MIC: E. coli 24hr_ppm | MIC: E. coli 48hr_ppm | MIC: F. oxysporum 72hr_ppm | MIC: M. fijiensis 144hr Agar_ppm | MIC: M. fijiensis 144hr_ppm |
|---|---|---|---|---|---|---|---|---|---|---|---|---|
| $C_{11}H_{12}BCl_2NO_2$ | 101 | | | | 101 | | | | | | | 1.56 |
| $C_9H_{11}BClNO_2$ | 101 | | | | 25 | | | | | | | 1.56 |
| $C_{10}H_{12}BCl_2NO_2$ | 201 | | | | 101 | | | | | | | 1.56 |
| $C_8H_8BFO_2$ | 201 | | | | 201 | | | | | | | 25 |
| $C_{10}H_{13}BO_2$ | 201 | | | | 201 | | | | | | | 101 |
| $C_7H_7BFNO_2$ | 101 | | | | 12.5 | | | | | | | 101 |

FIG. 3EE

| Structures | MIC: P. capsici 72hr_ppm | MIC: R. solani 72hr Agar_ppm | MIC: R. solani 72hr_ppm | MIC: S. sclerotiorum 72hr_ppm | MIC: X. campestris 48hr_ppm | MIC: X. campestris 72hr_ppm | MIC: C. sublineolum 120 hr Agar_ppm | MIC: C. sublineolum 72hr_ppm | MIC: P. nodorum 120hr_ppm |
|---|---|---|---|---|---|---|---|---|---|
|  $C_{11}H_{12}BCl_2NO_2$ | | | 25 | | | | | 6.25 | |
|  $C_9H_{11}BClNO_2$ | | | 25 | | | | | 25 | |
|  $C_{10}H_{12}BCl_2NO_2$ | | | 25 | | | | | 25 | |
|  $C_8H_8BFO_2$ | | | 3.13 | | | | | 201 | |
|  $C_{10}H_{13}BO_2$ | | | 201 | | | | | 201 | |
|  $C_7H_7BFNO_2$ | | | 25 | | | | | 201 | |
FIG. 3FF

| Structures | MIC: A. flavus 72hr_ppm | MIC: A. solani 72hr_ppm | MIC: A. tumefaciens 24hr_ppm | MIC: A. tumefaciens 48hr_ppm | MIC: B. cinerea 72hr_ppm | MIC: E. amylovora 24hr_ppm | MIC: E. amylovora 48hr_ppm | MIC: E. coli 24hr_ppm | MIC: E. coli 48hr_ppm | MIC: F. oxysporum 72hr_ppm | MIC: M. fijiensis 144hr Agar_ppm | MIC: M. fijiensis 144hr_ppm |
|---|---|---|---|---|---|---|---|---|---|---|---|---|
| C$_{10}$H$_{13}$BO$_2$ | 201 | | | | 201 | | | | | | | 101 |
| C$_9$H$_{11}$BFNO$_2$ | 201 | | | | 101 | | | | | | | 6.25 |
| C$_7$H$_6$BClFNO$_2$ | 12.5 | | | | 1.56 | | | | | | | 0.2 |
| C$_8$H$_9$BO$_3$ | 201 | | | | 201 | | | | | | | 25 |
| C$_9$H$_{10}$BClFNO$_2$ | 12.5 | | | | 201 | | | | | | | 0.39 |
| C$_{10}$H$_{14}$BNO$_2$ | 201 | | | | 201 | | | | | | | 101 |
| C$_{11}$H$_{14}$BNO$_2$ | | | | | | | | | | | | |

FIG. 3GG

| Structures | MIC: P. capsici 72hr_ppm | MIC: R. solani 72hr Agar_ppm | MIC: R. solani 72hr_ppm | MIC: S. sclerotiorum 72hr_ppm | MIC: X. campestris 48hr_ppm | MIC: X. campestris 72hr_ppm | MIC: C. sublineolum 120 hr Agar_ppm | MIC: C. sublineolum 72hr_ppm | MIC: P. nodorum 120hr_ppm |
|---|---|---|---|---|---|---|---|---|---|
| $C_{10}H_{13}BO_2$ | | | 20↓ | 20↓ | | | | 20↓ | |
| $C_9H_{11}BFNO_2$ | | | 10↓ | 10↓ | | | | 10↓ | |
| $C_7H_6BClFNO_2$ | | | 1.56 | | | | | 0.2 | |
| $C_8H_9BO_3$ | | | 10↓ | 10↓ | | | | 20↓ | |
| $C_9H_{10}BClFNO_2$ | | | 6.25 | 6.25 | | | | 6.25 | |
| $C_{10}H_{13}BNO_2$ | | | 20↓ | 20↓ | | | | 20↓ | |
| $C_{11}H_{13}BNO_2$ | | | | | | | | | |

FIG. 3HH

| Structures | MIC: P. capsid 72hr_ppm | MIC: R. solani 72hr Agar_ppm | MIC: R. solani 72hr_ppm | MIC: S. sclerotiorum 72hr_ppm | MIC: X. campestris 48hr_ppm | MIC: X. campestris 72hr_ppm | MIC: C. sublineolum 120 hr Agar_ppm | MIC: C. sublineolum 72hr_ppm | MIC: P. nodorum 120hr_ppm |
|---|---|---|---|---|---|---|---|---|---|
| 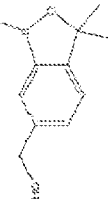 $C_{10}H_{13}BO_3$ | | |

| Structure | MIC: A. flavus 72hr ppm | MIC: A. solani 72hr ppm | MIC: A. tumefaciens 24hr ppm | MIC: A. tumefaciens 48hr ppm | MIC: B. cinerea 72hr ppm | MIC: E. amylovora 24hr ppm | MIC: E. amylovora 48hr ppm | MIC: E. coli 24hr ppm | MIC: E. coli 48hr ppm | MIC: F. oxysporum 72hr ppm | MIC: M. fijiensis 144hr Agar ppm |
|---|---|---|---|---|---|---|---|---|---|---|---|
|  C8H8BClO2 | 3.13 | 101 | 3.13 | 101 | 12.5 | 25 | 101 | 12.5 | 101 | 101 | 101 |
| 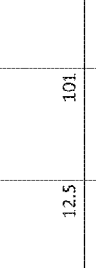 C8H8BFO2 | 12.5 | 101 | 0.39 | 101 | 12.5 | 6.25 | 101 | 6.25 | 101 | 101 | 101 |
|  C7H5BClFO2 | 0.2 | 101 | 0.78 | 101 | 0.39 | 3.13 | 101 | 6.25 | 101 | 101 | 101 |
|  C7H6BFO2 | 0.2 | 101 | 0.39 | 101 | 0.01 | 1.56 | 101 | 12.5 | 101 | 101 | 101 |
FIG. 3KK

| Structure | MIC: M. fijiensis 144hr_ppm | MIC: P. capsici 72hr_ppm | MIC: R. solani 72hr Agar_ppm | MIC: R. solani 72hr_ppm | MIC: S. sclerotiorum 72hr_ppm | MIC: X. campestris 48hr_ppm | MIC: X. campestris 72hr_ppm | MIC: C. sublineolum 120 hr Agar_ppm | MIC: C. sublineolum 72hr_ppm | MIC: P. nodorum 120hr_ppm |
|---|---|---|---|---|---|---|---|---|---|---|
| $C_8H_8BClO_2$ | 3.13 | 101 | 101 | 12.5 | 101 | 25 | 101 | 101 | 3.13 | 3.13 |
| $C_8H_8BFO_2$ | 6.25 | 101 | 101 | 25 | 101 | 3.13 | 101 | 201 | 12.5 | 3.13 |
| $C_7H_5BClFO_2$ | 0.2 | 101 | 101 | 1.56 | 101 | 25 | 101 | 101 | 0.39 | 1.56 |
| $C_7H_5BFO_2$ | 0.78 | 101 | 101 | 0.39 | 101 | 6.25 | 101 | 101 | 0.78 | 0.39 |

FIG. 3LL

| Structures | MIC: A. flavus 72hr_ppm | MIC: A. solani 72hr_ppm | MIC: A. tumefaciens 24hr_ppm | MIC: A. tumefaciens 48hr_ppm | MIC: B. cinerea 72hr_ppm | MIC: E. amylovora 24hr_ppm | MIC: E. amylovora 48hr_ppm | MIC: E. coli 24hr_ppm | MIC: E. coli 48hr_ppm | MIC: F. oxysporum 72hr_ppm | MIC: M. fijiensis 144hr Agar_ppm | MIC: M. fijiensis 144hr_ppm |
|---|---|---|---|---|---|---|---|---|---|---|---|---|
| C9H7BO3 | 6.25 | 101 | 6.25 | 101 | 6.25 | 6.25 | 101 | 101 | 101 | 101 | 101 | 3.13 |
| C9H5BClNO2 | 6.25 | 101 | 101 | 101 | 6.25 | 201 | 201 | 201 | 101 | 101 | 101 | 0.78 |
| C9H5BClNO2 | 201 | 101 | 0.78 | 101 | 100 | 6.25 | 6.25 | 12.5 | 101 | 101 | 101 | 201 |
| C9H6BClO2 | 6.25 | 101 | 3.13 | 101 | 100 | 101 | 101 | 101 | 101 | 101 | 101 | 6.25 |
| C9H6BNO4 | 3.13 | 101 | 101 | 101 | 25 | 101 | 101 | 101 | 201 | 101 | 101 | 1.56 |
| C9H6BClNO4 | 3.13 | 101 | 101 | 201 | 50 | 101 | 101 | 101 | 201 | 101 | 101 | 1.56 |

FIG. 3MM

| Structures | MIC: P. capsici 72hr_ppm | MIC: R. solani 72hr Agar_ppm | MIC: R. solani 72hr_ppm | MIC: S. sclerotiorum 72hr_ppm | MIC: X. campestris 48hr_ppm | MIC: X. campestris 72hr_ppm | MIC: C. sublineolum 120 hr Agar_ppm | MIC: C. sublineolum 72hr _ppm | MIC: P. nodorum 120hr_ppm |
|---|---|---|---|---|---|---|---|---|---|
|  $C_8H_7BO_3$ | 101 | 101 | 12.5 | 101 | 101 | 101 | 101 | 3.13 | 1.56 |
|  $C_7H_5BClNO_4$ | 101 | 101 | 25 | 101 | 101 | 101 | 101 | 6.25 | 6.25 |
|  $C_8H_5BClNO_2$ | | 201 | 100 | | 25 | 101 | 201 | 101 | |
|  $C_8H_6BClO_3$ | 101 | 201 | 100 | 101 | 101 | 201 | 101 | 0.78 | 6.25 |
|  $C_7H_6BNO_4$ | 101 | 101 | 12.5 | 101 | | | 101 | 3.13 | 3.13 |
|  $C_7H_5BClNO_4$ | 101 | 201 | 50 | 101 | | | 101 | 6.25 | |

FIG. 3NN

| Structures | MIC: A. flavus 72hr_ppm | MIC: A. solani 72hr_ppm | MIC: A. tumefaciens 24hr_ppm | MIC: A. tumefaciens 48hr_ppm | MIC: B. cinerea 72hr_ppm | MIC: E. amylovora 24hr_ppm | MIC: E. amylovora 48hr_ppm | MIC: E. coli 24hr_ppm | MIC: E. coli 48hr_ppm | MIC: F. oxysporum 72hr_ppm | MIC: M. fijiensis 144hr Agar_ppm | MIC: M. fijiensis 144hr_ppm |
|---|---|---|---|---|---|---|---|---|---|---|---|---|
| OB1OCC2=CC(C)=C(C=C12)NC | 201 | | | | 201 | | | | | | | 3.13 |
| OB1OCC2=CC(C)=C(C=C12)NC | | 101 | | | 201 | | | | | | | 0.78 |
| OB1OCC2=CC(C)=C(C=C12)NC | 201 | | | | 201 | | | | | | | 12.5 |
| OB1OCC2=CC(C)=C(C=C12)NC | 201 | | | | 201 | | | | | | | 101 |
| $C_{13}H_{18}BClN_2O_3$ | | | | | | | | | | | | |
| $C_{10}H_{11}BO_3$ | 201 | | | | 201 | | | | | | | 101 |

FIG. 30O

| Structures | MIC: P. capsici 72hr_ppm | MIC: R. solani 72hr Agar_ppm | MIC: R. solani 72hr_ppm | MIC: S. sclerotiorum 72hr_ppm | MIC: X. campestris 48hr_ppm | MIC: X. campestris 72hr_ppm | MIC: C. sublineolum 120 hr Agar_ppm | MIC: C. sublineolum 72hr_ppm | MIC: P. nodorum 120hr_ppm |
|---|---|---|---|---|---|---|---|---|---|
| OB1OCC2=CC(C)=C(C=C12)NC... | | | 201 | | | | | 201 | |
| OB1OCC2=CC(C)=C(C=C12)NC... | | | 1.56 | | | | | 12.5 | |
| OB1OCC2=CC(C)=C(C=C12)NC... | | | 12.5 | | | | | 12.5 | |
| OB1OCC2=CC(C)=C(C=C12)NC... | | | 201 | | | | | 201 | |
| $C_{13}H_{18}BClN_2O_3$ | | | 201 | | | | | 101 | |
| $C_{10}H_{11}BO_3$ | | | | | | | | | |

FIG. 3PP

| Structures | MIC: A. flavus 72hr_ppm | MIC: A. solani 72hr_ppm | MIC: A. tumefaciens 24hr_ppm | MIC: A. tumefaciens 48hr_ppm | MIC: B. cinerea 72hr_ppm | MIC: E. amylovora 24hr_ppm | MIC: E. amylovora 48hr_ppm | MIC: E. coli 24hr_ppm | MIC: E. coli 48hr_ppm | MIC: F. oxysporum 72hr_ppm | MIC: M. fijiensis 144hr Agar_ppm | MIC: M. fijiensis 144hr_ppm |
|---|---|---|---|---|---|---|---|---|---|---|---|---|
| $C_{10}H_{11}BO_3$ | 201 | | | | 201 | | | | | | | 101 |
| $C_{10}H_{11}BO_3$ | 201 | | | | 201 | | | | | | | 101 |
| $C_{11}H_{14}BNO_3$ | | | | | | | | | | | | |

FIG. 3QQ

| Structures | MIC: P. capsici 72hr_ppm | MIC: R. solani 72hr Agar_ppm | MIC: R. solani 72hr_ppm | MIC: S. sclerotiorum 72hr_ppm | MIC: X. campestris 48hr_ppm | MIC: X. campestris 72hr_ppm | MIC: C. sublineolum 120 hr Agar_ppm | MIC: C. sublineolum 72hr_ppm | MIC: P. nodorum 120hr_ppm |
|---|---|---|---|---|---|---|---|---|---|
| $C_{10}H_{11}BO_3$ | | | 201 | | | | | 201 | |
| $C_{10}H_{11}BO_3$ | | | 101 | | | | | 101 | |
| $C_{11}H_{13}BNO_3$ | | | | | | | | | |

FIG. 3RR

| Structure | MIC: A. flavus 72hr Agar_ppm | MIC: A. flavus 72hr_ppm | MIC: A. solani 72hr_ppm | MIC: A. tumefaciens 24hr_ppm | MIC: A. tumefaciens 48hr_ppm | MIC: B. cinerea 72hr_ppm | MIC: E. amylovora 24hr_ppm | MIC: E. amylovora 48hr_ppm | MIC: E. coli 24hr_ppm | MIC: E. coli 48hr_ppm | MIC: F. oxysporum 72hr_ppm | MIC: M. fijiensis 144hr Agar_ppm |
|---|---|---|---|---|---|---|---|---|---|---|---|---|
| NC1=C(Cl)C2=C2COB(O)C2=C1Cl | >100 | | 6.25 >100 | 0.39 >100 | >100 | 3.13 | 1.56 >100 | 0.78 >100 | | | | |
| OB1OCC2=C(C=CC=C12)C(O)=O | >100 | >100 | | >100 | >100 | >100 | >100 | >100 | >100 | >100 | >100 | >100 |
| OB1OCC2=CC(=CC(Cl)=C12)C(O)=O | >100 | | | >100 | >100 | >100 | >100 | >100 | >100 | >100 | >100 | |
| CS(=O)(=O)C1=C(Cl)C=C2COB(O)C2=C1O | >100 | >100 | | >100 | >100 | >100 | >100 | >100 | >100 | >100 | | >100 |
| OB1OCC2=C(C)C=CC=C12 | >100 | >100 | | >100 | >100 | >100 | >100 | >100 | >100 | >100 | | >100 |

FIG. 3SS

| Structure | MIC: M. fijiensis 144hr_ppm | MIC: P. capsici 72hr_ppm | MIC: R. solani 72hr Agar_ppm | MIC: R. solani 72hr_ppm | MIC: S. sclerotiorum 72hr_ppm | MIC: X. campestris 48hr_ppm | MIC: X. campestris 72hr_ppm | MIC: C. sublineolum 120 hr Agar_ppm | MIC: C. sublineolum 72hr_ppm | MIC: P. nodorum 120hr_ppm |
|---|---|---|---|---|---|---|---|---|---|---|
| NC1=C(Cl)C(=C2COB(O)C2=C1Cl | 0.78125 | >100 | >100 | 12.5 | >100 | 0.78 | >100 | >100 | 0.78125 | 6.25 |
| OB1OCC2=C(C(=CC=C12)C(O)=O | | | >100 | >100 | >100 | | >100 | >100 | >100 | |
| OB1OCC2=C(C(=CC(Cl)=C12)C(O)=O | >100 | | | >100 | | >100 | >100 | >100 | >100 | >100 |
| CS(=O)(=O)C1=C(C)C(=CC2COB(O)C2 | >100 | | | >100 | | | >100 | >100 | >100 | |
| OB1OCC2=C(O)C=CC=C12 | >100 | | >100 | | | | | >100 | >100 | |

FIG. 3TT

BENZOXABOROLE COMPOUNDS AND FORMULATIONS THEREOF

CROSS-REFERENCE TO RELATED APPLICATIONS

This application is a National Stage application of International Application No. PCT/US2018/063389, filed Nov. 30, 2018, which claims the benefit of U.S. Provisional Application No. 62/593,226, filed on Nov. 30, 2017, and U.S. Provisional Application No. 62/743,489, filed on Oct. 9, 2018.

TECHNICAL FIELD

The present invention relates to benzoxaborole compounds and to formulations of benzoxaborole compounds comprising surfactants and/or suitable carriers for agricultural or therapeutic use (e.g., as phytopathogenic and/or infectious agent control, growth enhancement or control). The invention also relates to methods of using the benzoxaborole compounds and the formulations thereof.

BACKGROUND

Boron is a unique, and often misconstrued, element of the periodic table due to its powerfully effective and potentially high toxicological properties. Initial innovation in the field of boron chemistry was impaired due to the incapacity to prepare pure boron, especially in its crystalline form. Early characterization of boron-containing molecules was also stymied by contamination of that crystalline form by aluminum. While the use of boron, in the form of boric acid, is well known for its use in agriculture, the construction and characterization of more complex boron-containing molecules that are both safe and effective has been relatively unexplored. Only recently has boron been explored by skilled organo-metallic chemists for novel and useful applications across human/animal health and agriculture. For example, boron-containing molecules such as oxaboroles and benzoxaboroles demonstrate use as antimicrobials, antiparasitics, and antifungals. (See Publication No. WO2016128949 (antimicrobial), U.S. Pat. No. 9,617,285 (antiparasitic), and Publication No. WO2016164589 (antifungal)).

The creation and development of such boron-containing compounds has proven to be unpredictable. Even in the hands of experts, boron containing scaffolds present compounds that must be tested from a toxicology, mode of action, and activity perspective. Moreover, once the target compounds are made and tested, formulation of those compounds can be laborious due to issues such as pKa, pH, and solubility. The duplicitous nature of boron-containing compounds places their activity on a broad continuum; including those that are highly toxic, and those that are exceptionally benign. Thus, creation of novel and useful boron-containing compounds requires skilled attention to design, synthesis, formulation, as well as thoughtful screening to determine toxicity, mode of action, and efficacy.

Moreover, boron's ability to covalently bond with other molecules makes it both attractive and difficult to work with. Boron-containing products have traditionally suffered in becoming commercially viable products due to synthetic and pharmacological uncertainties. However, these characteristics can be leveraged, in the right hands, to make great impact in the areas of crop protection and animal health.

In addition to being capable of affecting a diverse array of pathogens by themselves, previous literature demonstrates the unique ability of boron-chemistry to enhance the efficacy of known active ingredients. See U.S. Pat. No. 9,737,075.

Within the field of plant health, fungal, bacterial, insect, and nematode plant pathogens lead to a wide range of diseases (rusts, spots, downy mildews, blasts, blotches, stripes, rots, smuts, pathogenic nematodes, erwinia, insects, etc.) across all crops, resulting in massive losses. Current solutions are limited; providing only a partial level of control (as with resistant cultivars), or adding significant costs relative to currently available, conventional, and outdated chemical pesticides. While breeding for resistance traits to specific crop/pathogen combinations in germplasm offers some hope in circumventing the problem, it is widely recognized that novel antifungals must be developed.

Antifungals, insecticides, and pesticides are costly to both purchase and use, as well as often being toxic and/or otherwise detrimental to off-target vegetation near the site of application including runoff, affecting the watershed. Moreover, many antifungals, insecticides, and pesticides lose efficacy over time, concomitantly with pathogens becoming resistant to treatment. It is beneficial to farmers, consumers, and their surrounding communities to use the minimum required dose of antifungals, insecticides, and/or pesticides to achieve maximum crop yield, while mitigating onset of resistance and environmental detriment.

While some benzoxaboroles have been demonstrated to exhibit antibacterial and antifungal activities, they have not been successfully employed as a commercial product for crop protection and agricultural pest-control. One reason may be the fluxional and reactive nature of benzoxaboroles. Benzoxaboroles can exist in a neutral trigonal planar geometry, an ionic tetrahedral geometry, or a mixture of both of these geometries depending on the specific environment of the benzoxaborole. Specifically, solvents, surfactants, stabilizers, antioxidants, pH, and other adjuvants commonly used as formulation ingredients can easily alter the benzoxaborole's geometry, formal charge (neutral trigonal or ionic tetrahedral) and complexation species in unpredictable ways. Further, this difference in formal charge (neutral vs. ionic), geometry (trigonal vs. tetrahedral), and complexation can greatly affect the biological activity of the benzoxaborole. For example, each benzoxaborole geometry can bind to a target protein differently, and the charge (neutral vs. ionic) can influence the cell permeability. Depending on the geometry and charge of the benzoxaborole, the benzoxaborole can ultimately be an effective, potent compound, or a compound that shows little or no bioactivity. Furthermore, the neutral trigonal planar benzoxaborole and ionic tetrahedral benzoxaborole each have unique physical chemical properties that are important to consider to develop an efficacious formulation of the benzoxaborole (e.g. solubility, stability, and pH).

It is an object of the present disclosure to provide compounds exhibiting control (e.g., curative, inhibitive, ameliorative, and/or preventative activity) of phytopathogens, fungi, pathogenic bacteria and/or microorganisms, and the like.

Surprisingly, the compounds described herein, when applied to plants, seeds, plant parts, harvested fruits, vegetables and/or plant's locus of growth allows for effective control of pathogenic microorganisms, fungi, bacteria, and other phytopathogens.

While the formulation of traditional, non-boron containing, organic active ingredients can be predicted by the physical characteristics of the overall molecule (log P, melting point, solubility, compound polarity, etc), the formulation of benzoxaboroles has an aspect of unpredictability—the formulation of the relatively reactive benzoxaborole functional group. In contrast to traditional, non-boron containing, organic active ingredients, the charge and geometry of the benzoxaborole is not static. Rather, the benzoxaborole can exist in a fluxional state, wherein the compound is in a dynamic equilibrium between the neutral, trigonal planar state and the ionic, trigonal planar state (Scheme 1). Additionally, substitutions on the benzoxaborole can have profound effects on this dynamic equilibrium. These characteristics together make the formulation of benzoxaborole compounds an unpredictable and challenging endeavor.

Scheme 1

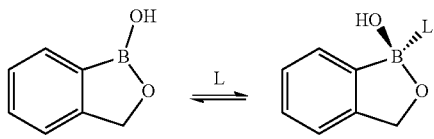

Furthermore, benzoxaboroles are primarily organic (easier to dissolve in organic solvents than in more water-like solvents) in nature due to being composed of predominately hydrocarbons. However, they also possess a relatively polar boron-hydroxyl group in the overall chemical structure, and the boron-hydroxyl group prefers to be in more water-like solvent. Additionally, the boron atom has an empty p-orbital, which readily forms covalent bonds with Lewis bases that may be present in the formulation (potentially affecting biological activity). Thus, the empty p-orbital on the boron of the benzoxaborole makes formulation of benzoxaborole active ingredients unpredictable and difficult relative to traditional, non-boron containing, organic molecules. This Lewis acidic center readily interacts with formulation components (solvents, surfactants, and other adjuvants) in unexpected ways. Accordingly, the formulation of benzoxaborole active ingredients requires novel approaches that heretofore have not been developed or considered for the formulation of traditional, non-boron containing agricultural or therapeutic formulations.

Therefore, there is a need for formulations comprising benzoxaboroles for the treatment of crops to control pathogenic infection to make this class of chemistry applicable beyond simple in vitro assays. While benzoxaborole formulations can be used in multiple applications, a preferred application is agricultural use. Moreover, these benzoxaborole formulations may be coupled with known active ingredients, or other additives to increase efficacy, stability, combat resistance, and/or spectrum broadening.

BRIEF SUMMARY OF THE INVENTION

In a first aspect of the invention, a benzoxaborole formulation composition comprises a benzoxaborole, a non-ionic surfactant, or a non-ionic and ionic surfactant mixture, and a carrier. At least one of the non-ionic surfactant, the non-ionic and ionic surfactant mixture, and the carrier comprise a Lewis base or a N—H or O—H bond. The carrier is a solid or a liquid.

In a feature of this aspect, the benzoxaborole has a structure (Ib):

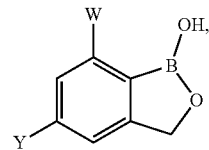

wherein Y is selected from the group consisting of: hydrogen, fluorine, chlorine, bromine, and iodine; and W is selected from the group consisting of: hydrogen, methyl, fluorine, chlorine, bromine, and iodine. The benzoxaborole may be a salt, stereoisomer, enantiomer, or tautomer of the compound of structure (Ib).

In another feature of this aspect, the benzoxaborole has a structure (Ic):

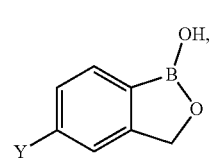

wherein Y is selected from the group consisting of: hydrogen, fluorine, chlorine, bromine, and iodine. The benzoxaborole may be a salt, stereoisomer, enantiomer, or tautomer of the compound of structure (Ic).

With regard to this feature, Y can be selected from the group consisting of: fluorine, chlorine, and hydrogen. In a feature of this aspect, the benzoxaborole is:

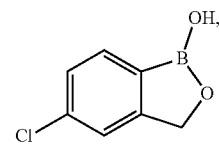 [SMILES: OB1OCc2cc(Cl)ccc21]

or a salt, stereoisomer, enantiomer, or tautomer thereof.

In a feature of this aspect, the non-ionic and ionic surfactants are independently selected from the group consisting of: high molecular weight polymers, polycondensates of ethylene oxide with fatty alcohols or with fatty acids or with fatty amines, substituted phenols (in particular alkylphenols or arylphenols such as mono- and di-(polyoxyalkylene alkylphenol), polycondensates of ethylene oxide with phosphate tristyrylphenols and polycondensates of ethylene oxide with phosphoric esters of alcohols or phenols, amine ethoxylates, castor oil ethoxylates and polyethylene glycol derivatives of hydrogenated castor oil, sorbitan fatty acid ester ethoxylates, polyoxyethylene sorbitan monolaurates, sorbitan fatty acid esters, sorbitan monolaurate, sorbitan monostearate, polyoxyethylene polyoxypropylene sorbitan monolaurates, non-ionic ethoxylates, branched and unbranched secondary alcohol ethoxylates, nonylphenol ethoxylates, octylphenol ethoxylates, fatty alcohol ethoxylates, alkyl phenol ethoxylates, castor oil based ethoxylates, fatty acid ethoxylates, EO-PO block co-polymers, acrylic co-polymers, styrene acrylic polymers, polyalkylene oxide block copolymers, sorbitan(ol) ester ethoxylates, sarcosinates, alkyl polysaccrharides, alkyl amine ethoxylates, amine oxides, siliconics, ethoxylated Graft & Comb polymers, propoxylated and non-ethoxylated Graft & Comb polymers, alkyl ether phosphates, alkyl phenol ether phosphates, alkyl phenol ether sulphates, condensed naphthalene sulfonates and salts, sodium alkyl naphthalene sulphonate blends, sodium alkyl naphthalene sulfonate, sodium alkylnapthalene formaldehyde condensates, sodium naphthalene sulphonate condensate, aromatic hydrocarbon sulfonic acids, aromatic hydrocarbon sulfonic salts, aromatic hydrocarbon sulfonic blends, fatty alcohol sulphates, alkyl ether carboxylic acids, alkyl ether carboxylic salts, alkyl ether sulphates, monosulphosuccinates, polysulphosuccinates, alkyl phosphates, alkyl benzene sulphonic acids, alkyl benzene sulphonic salts, lignosulphonates and salts, alkylaryl sulphonates, alkylbenzene sulphonates, calcium alkylaryl sulphonates, and alpha olefin sulphonates.

With regard to this feature, the pKa of the benzoxaborole is between 6 and 10, preferably between 6 and 8.

In another feature of this aspect, the weight/weight % of benzoxaborole in the benzoxaborole formulation is 5% to 60% w/w if the carrier is a liquid, and the weight/weight % of benzoxaborole in the benzoxaborole formulation is 20% to 99.9% w/w if the carrier is a solid. Preferably, the weight/weight % of benzoxaborole in the benzoxaborole formulation is 10% to 50% w/w if the carrier is a liquid, and the weight/weight % of benzoxaborole in the benzoxaborole formulation is 20% to 80% w/w if the carrier is a solid.

In an additional feature of this aspect, the concentration of surfactant in the benzoxaborole formulation is between 0.1% and 35% w/w. In another feature of this aspect, the composition further comprises an antioxidant.

In yet another feature of this aspect, the carrier is a liquid and comprises a solvent selected from the group consisting of: a protic solvent, water, $C_1$-$C_{15}$ branched alcohols, $C_1$-$C_{15}$ linear alcohols, benzyl alcohol, oleyl alcohol, cetyl alcohol, lauryl alcohol, 2-propanol, methanol, n-decanol, 1-propanol, ethanol, 1-hexanol, isobutyl alcohol, n-octanol, 1-butanol, pentanol, cyclohexanol, and mixtures thereof, alcohols, ethylene glycol monomethyl ether, or a mixture thereof. With regard to this feature, the carrier further comprises a second liquid carrier selected from the group consisting of: an aprotic solvent, a ketone, cyclohexanone, isophorone, or N-methyl-2-pyrrolidone. The carrier may comprise a mixture of a protic solvent and an aprotic solvent, preferably the aprotic solvent is polar. Moreover, the carrier may be a solid.

In a feature of this aspect, the benzoxaborole formulation is an emulsion concentrate (EC), a suspension concentrate (SC), a wettable powder (WP), a water dispersible granule (WDG), or a seed treatment. The formulation composition may further comprise an aqueous diluent. The aqueous diluent may have a pH between about 5.5 and 9.5, for example, between about 6 and 8.

In another feature of the aspect, the composition further comprises at least one fungicide selected from the group consisting of: carbendazim, thiabendazole, thiophanate, thiophanate-methyl, diethofencarb, zoxamide, ethaboxam, pencycuron, flupicolide, flutolanil, fluopyram, fluxapyroxad, penthiopyrad, benodanil, mepronil, isofetamid, fenfuram, carboxin, oxycarboxin, thifluzamide, benzovindiflupyr, bixafen, furametpyr, isopyrazam, penflufen, sedaxane, boscalid, benomyl, fuberidazole, diflumetorim, tolfenpyrad, azoxystrobin, coumoxystrobin, enoxastrobin, flufenoxystrobin, picoxystrobin, pyraoxystrobin, mandestrobin, pyraclostrobin, pyrametostrobin, triclopyricarb, kresoximmethyl, trifloxystrobin, dimeoxystrobin, fenamistrobin, methominostrobin, orysastrobin, famoxadone, fluoxastrobin, fenamidone, pyribencarb, cyazofamid, amisulbrom, binapacryl, meptyldinocap, dinocap, fluazinam, fentin chloride, fentin acetate, fentin hydroxide, silthiofam, ametoctradin, cyprodinil, mepanipyrim, pyrimethanil, kasugamycin, quinoxyfen, proquinazid, fenpiclonil, fludioxonil, chlozolinate, dimethachlone, iprodione, procymidone, vinclozolin, triforine, pyrifenox, pyrisoxazole, fenarimol, nuarimol, imazalil, oxpoconazole, pefurazoate, prochloraz, triflumizole, azaconazole, bitertanol, bromuconazole, cyproconazole, diniconazole, epoxiconazole, etanconazole, fenbuconazole, fluquinconazole, flusilazole, flutriafol, hexaconazole, imibenconazole, ipconazole, metconazole, myclobutanil, penconazole, propiconazole, simeconazole, tebuconazole, tetraconazole, triadimefon, triadimenol, triticonazole, prothioconazole, aldimorph, dodemorph, fenpropimorph, tridemorph, fenpropidin, piperalin, spiroxamine, fenhexamid, fenpyrazamine, pyributicarb, naftifine, terbinafine, validamycin, polyoxin, dimethomorph, flumorph, pyrimorph, benthiavalicarb, iprovalicarb, valifenalate, mandipropamid, ferbam, macozeb, maneb, metiram, propineb, thiram, zineb, ziram, captan, captafol, folpet, dichlofluanid, tolylfluanid, and chlorothalonil.

In an additional feature of the aspect, the composition further comprises at least one insecticide/nematicide selected from the group consisting of: avermectin group, such as abamectin; carbamate group, such as, aldicarb, thiadicarb, carbofuran, carbosulfan, oxamyl, aldoxycarb, ethoprop, methomyl, benomyl, alanycarb; and organophosphorus group, such as, fenamiphos, fensulfothion, terbufos, fosthiazate, dimethoate, phosphocarb, dichlofenthion, isamidofos, fosthietan, isazofos ethoprophos, cadusafos, terbufos, chlorpyrifos, dichlofenthion, heterophos, isamidofos, mecarphon, phorate, thionazin, triazophos, diamidafos, fosthietan, phosphamidon, and dichloropropene.

Additionally, the composition may comprise at least one insecticide selected from the group consisting of: a phenylpyrazole group, such as ethiprole and fipronil; a pyrethroid group, such as acrinathrin, allethrin, bifenthrin, bioallenthrin, bioresmethrin, cycloprothrin, cyfluthrin, cyhalothrin, cypermethrin, cyphenothrin, deltamethrin, esfenvalerate, etofenprox, fenpropathrin, fenvalerate, flucythrinate, flumethrin, halfenprox, imiprothrin, kadethrin, permethrin, prallethrin, pyrethrins, resmethrin, silafluofen, tefluthrin, tetramethrin, tetramethrin, tralomethrin, and transfluthrin; and a neonicotinoid group: such as acetamiprid, clothianidin, dinotefuran, imidacloprid, nitenpyram, thiacloprid, and thiamethoxam; and a spinosyn group: such as spinetoram and spinosad.

In a second aspect of the invention, a method of controlling a phytopathogenic disease on crops, seeds, plants, plant parts, or plant propagation material comprises applying an effective amount of the composition of the first aspect to said crops, seeds, plants, plant parts, or plant propagation material.

In a third aspect of the invention, a method of controlling a phytopathogenic disease on crops, seeds, plants, plant parts, or plant propagation material comprises applying an effective amount of the composition of the first aspect, wherein said application is topical, to the soil, foliar, a foliar spray, systemic, a seed coating, a soil drench, directly in-furrow dipping, drenching, soil drenching, spraying, atomizing, irrigating, evaporating, dusting, fogging, broadcasting, foaming, painting, spreading-on, watering (drenching), and/or drip irrigating.

In a fourth aspect of the invention, a benzoxaborole compound is represented by formula (I):

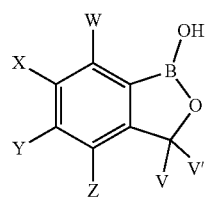
(I)

wherein:
W is selected from the group consisting of: hydrogen, halogen, $CH_3$, $CF_3$, Ethyl, $OCH_3$, $OCF_3$, $OCF_2H$, $CFH_2$, OEthyl, O-n-propyl, O-n-butyl, O-iso-propyl, O-sec-butyl, O-iso-butyl, O-cyclopropyl, O-cyclbutyl, C(O)H, CN, $CH_2OH$, $SR^1$, and $S(O)R^1$, wherein $R^1$ is selected from C1-C3 hydrocarbyl;

X is selected from the group consisting of: hydrogen, $R^2$, $OR^2$, $OCF_2H$, $NR^2_2$, $NHR^2$, $NH_2$, halogen, $CO_2R^2$, CN, OH, $CH_2OH$, $NO_2$, C(O)H, $SR^2$, and $S(O)R^2$, wherein each $R^2$ is independently selected from C1-C7 hydrocarbyl and C3-C6 cyclohydrocarbyl or each $R^2$ can be taken together to form a ring;

Y is selected from the group consisting of: hydrogen, halogen, $CH_3$, $NO_2$, C(O)H, and $CO_2R^3$, wherein $R^3$ is selected from C1-C4 hydrocarbyl and C3-C4 cyclohydrocarbyl;

Z is selected from the group consisting of: hydrogen, halogen, $R^4$, $NR^4_2$, $NHR^4$, $NH_2$, $NO_2$, $CO_2R^4$, $OR^4$, OH, $OCF_2H$, $SR^4$, and $S(O)R^4$, wherein $R^4$ is selected from C1-C3 hydrocarbyl and C3 cyclohydrocarbyl; and V and V' are independently selected from the group consisting of hydrogen and $CH_3$, or a salt, stereoisomer, enantiomer, or tautomer thereof.

In a fifth aspect of the invention, a benzoxaborole compound is represented by formula IaI:

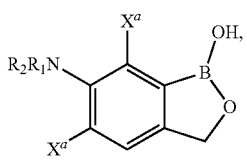
(IaI)

wherein:
$R_1$ is equal to $R_2$, or $R_1$ is not equal to $R_2$, and
  $R_1$ and/or $R_2$ are selected from the group consisting of: hydrogen, methyl, ethyl, propyl, butyl, and pentyl, or
  $R_1$ and $R_2$ are taken together to form a 3 to 6 membered ring; and
each $X^a$ is independently selected from the group consisting of: fluorine, chlorine, bromine, and iodine, or a salt, stereoisomer, enantiomer, or tautomer thereof.

In a sixth aspect of the invention, a benzoxaborole compound is represented by formula IaII:

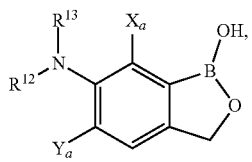
(IaII)

wherein:
each $R^{12}$ or $R^{13}$ is independently selected from the group consisting of hydrogen, methyl, ethyl, propyl, butyl, pentyl, $C_1$-$C_7$ hydrocarbyl, C3-C6 cyclohydrocabyl, $-CH_2C\equiv CR_4^a$, $-CH_2C\equiv CPh$, $CH_2C\equiv CCH_2Ph$, and $C_1$-$C_7$ hydrocarbyl having 1-15 $R_4^a$ substitutions; or
$R^{12}$ and $R^{13}$ taken together, form a 3 to 6 membered ring with the nitrogen atom to which they are bonded to;

each $X^a$ is independently selected from the group consisting of: hydrogen, fluorine, chlorine, bromine, and iodine;

each $Y_a$ is independently selected from the group consisting of hydrogen, fluorine, chlorine, bromine, and iodine; and each $R_4^a$ is independently selected from the group consisting of alkyl, substituted alkyl, cyclopropyl and cyclobutyl, or a salt, stereoisomer, enantiomer, or tautomer thereof.

In a seventh aspect of the invention, the benzoxaborole compound is selected from the group consisting of:

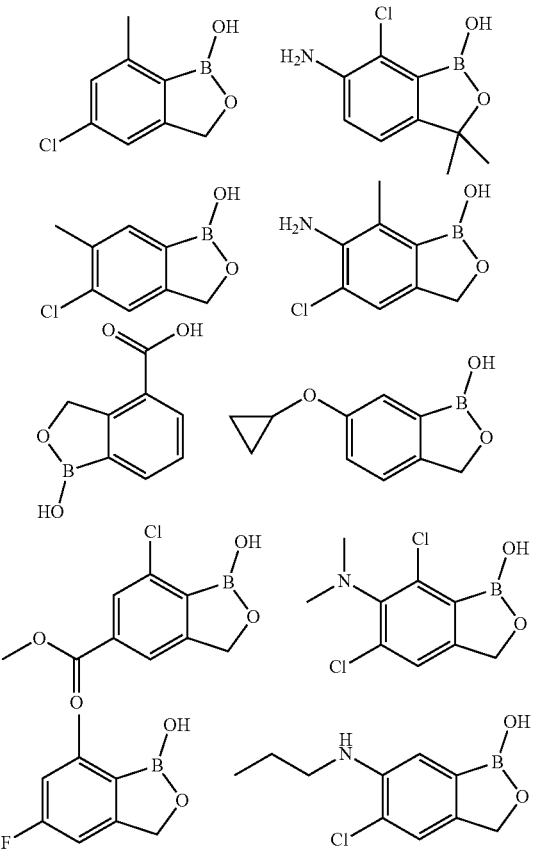

-continued

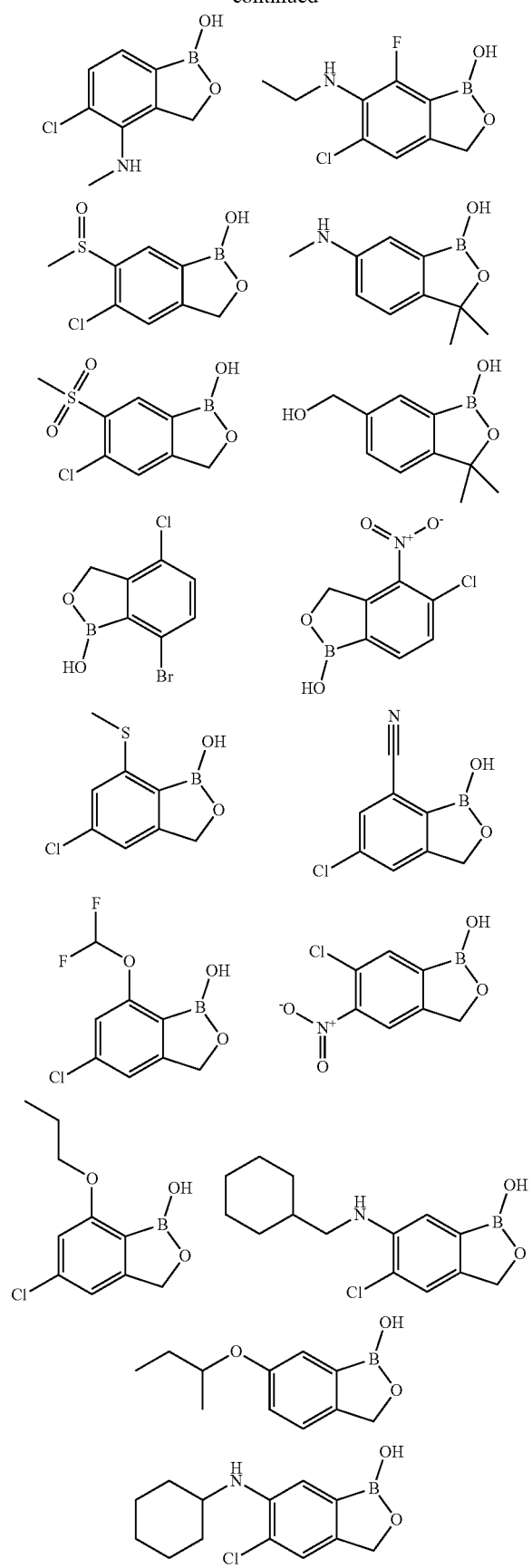
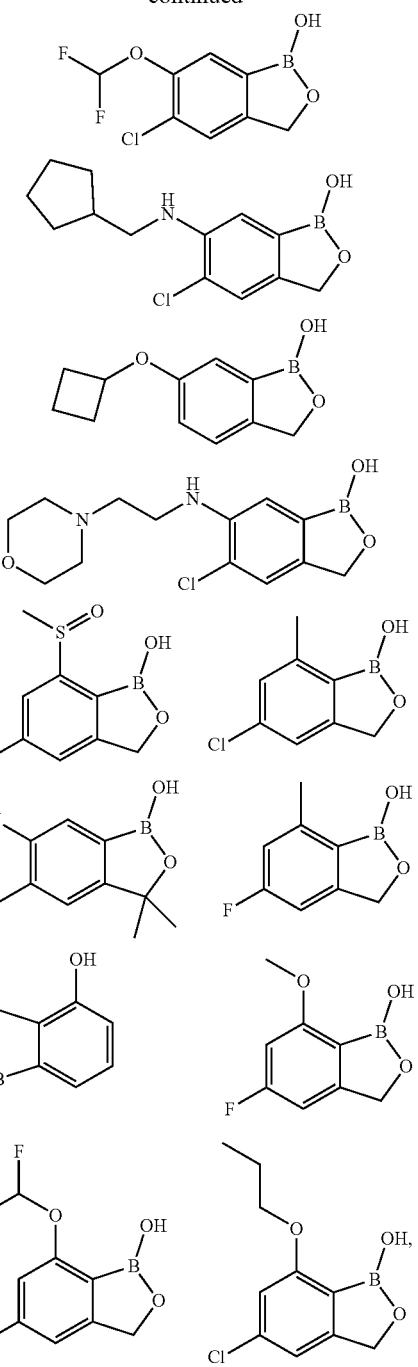

or a salt, stereoisomer, enantiomer, or tautomer thereof.

In a feature of the sixth aspect, at least one of $R^{12}$ and $R^{13}$ is $CH_2C\equiv CR_4^a$, wherein $R_4^a$ is selected from the group consisting of alkyl, substituted alkyl, cyclopropyl and cyclobutyl. In another feature of the sixth aspect, at least one of $R^{12}$ and $R^{13}$ is -$CH_2C\equiv CPh$ or $CH_2=CCH_2Ph$.

In a feature of the fifth aspect, the compound is selected from the group consisting of:

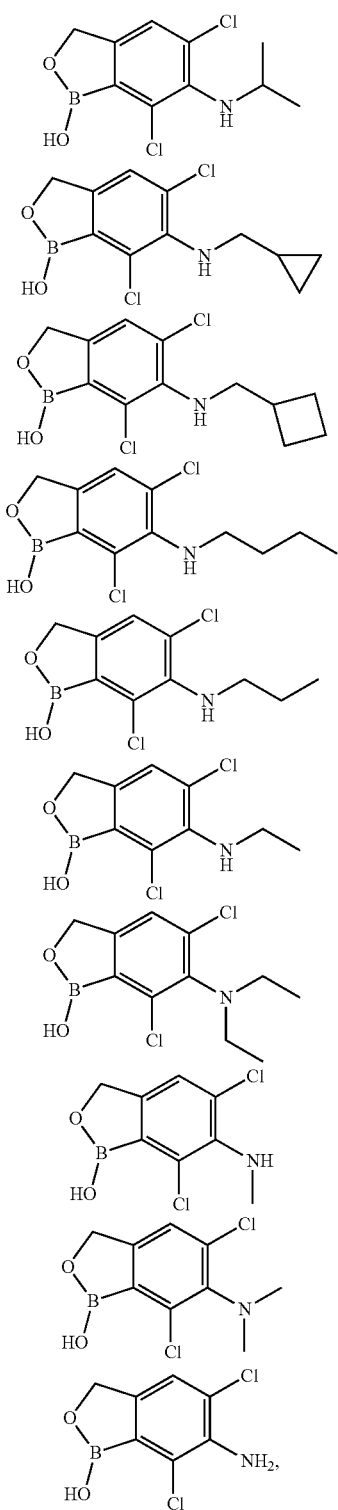

or a salt, stereoisomer, enantiomer, or tautomer thereof.

In an eighth aspect of the invention, an emulsion concentrate formulation composition comprises a benzoxaborole, a non-ionic surfactant, or a non-ionic and ionic surfactant mixture, and a liquid carrier. At least one of the non-ionic surfactant, the non-ionic and ionic surfactant mixture, and the liquid carrier comprise a Lewis base or a N—H or O—H bond.

In a feature of the eighth aspect, the benzoxaborole is:

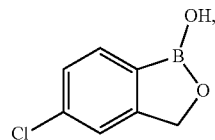 [SMILES: OB1OCc2cc(Cl)ccc21]

or a salt, stereoisomer, enantiomer, or tautomer thereof.

The another feature of the eighth aspect, the liquid carrier comprises a protic solvent. Additionally, the liquid carrier may comprise a mixture of a protic solvent and an aprotic solvent. The aprotic solvent may be a polar aprotic solvent or a non-polar aprotic solvent.

In a ninth aspect of the invention, a method for reducing, preventing, ameliorating, or inhibiting an infestation by a pathogen comprises applying a compound according to any aspect of the invention, wherein the pathogen is selected from a group consisting of: insects, nematodes, bacteria, microbes, fungi, protozoa, viruses, and parasites, or any combinations thereof. With regard to the method, the compound may be applied to an animal, a plant, a plant part, seeds, or plant propagation material.

BRIEF DESCRIPTION OF FIGURES

FIG. 2A-2I is a table that provides chemical characterization data for a number of exemplary benzoxaborole compounds, including some of those for which synthesis is described in the Syntheses Examples Section.

DETAILED DESCRIPTION

Definitions

Figure 1:
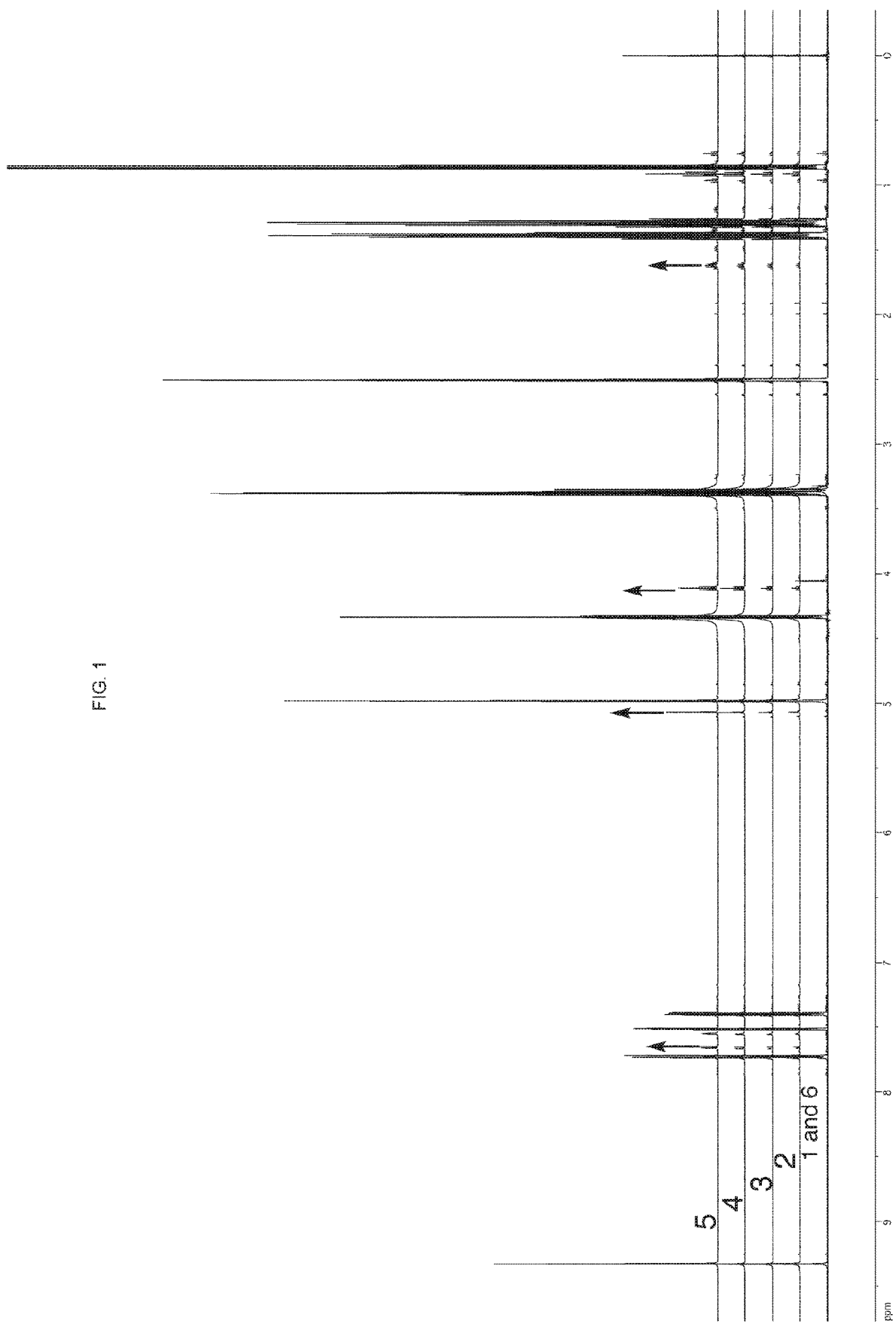
FIG. 1 is an image of the $^1$H-NMR spectra recorded in association with Example 22 of the formulation examples.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

As used herein, the term "hydrocarbyl" is a short hand term for a non-aromatic group that includes straight and branched chain aliphatic as well as alicyclic groups or radicals that contain only carbon and hydrogen. Inasmuch as alicyclic groups are cyclic aliphatic groups, such substituents are deemed to be subsumed within the aliphatic groups. Thus, alkyl, alkenyl, and alkynyl groups are contemplated.

Exemplary hydrocarbyl groups contain a chain of 1 to about 6 carbon atoms, and more preferably 1 to 4 carbon atoms. Examples of hydrocarbyl radicals include methyl, ethyl, n-propyl, isopropyl, n-butyl, isobutyl, sec butyl, tert-butyl, pentyl, iso-amyl, hexyl, and the like. Examples of suitable alkenyl radicals include ethenyl (vinyl), 2 propenyl, 3 propenyl, 1,4-pentadienyl, 1,4 butadienyl, 1-butenyl, 2-butenyl, 3-butenyl, and the like. Examples of alkynyl radicals include ethynyl, 2-propynyl, 3 propynyl, decynyl, 1 butynyl, 2-butynyl, 3-butynyl, and the like.

An alkyl group is a preferred hydrocarbyl group. As a consequence, a generalized, but more preferred substituent can be recited by replacing the descriptor "hydrocarbyl" with "alkyl" in any of the substituent groups enumerated herein. Where a specific aliphatic hydrocarbyl substituent group is intended, that group is recited; i.e., C1-C4 alkyl, methyl, or dodecenyl.

A contemplated cyclohydrocarbyl substituent ring contains 3 to 6 carbon atoms. The term "cycloalkylalkyl" means an alkyl radical as defined above that is substituted by a cycloalkyl radical. Examples of such cycloalkyl radicals include cyclopropyl, cyclobutyl, cyclopentyl, cyclohexyl, and the like.

Usual chemical suffix nomenclature is followed when using the word "hydrocarbyl" except that the usual practice of removing the terminal "yl" and adding an appropriate suffix is not always followed because of the possible similarity of a resulting name to that of one or more substituents. Thus, a hydrocarbyl ether is referred to as a "hydrocarbyloxy" group rather than a "hydrocarboxy" group as may possibly be more proper when following the usual rules of chemical nomenclature. Illustrative hydrocarbyloxy groups include methoxy, ethoxy, and cyclohexenyloxy groups. On the other hand, a hydrocarbyl group containing a C(O)-functionality is referred to as a hydrocarboyl (acyl) and that containing a —C(O)O— is a hydrocarboyloxy group inasmuch as there is no ambiguity. Exemplary hydrocarboyl and hydrocarboyloxy groups include acyl and acyloxy groups, respectively, such as formyl, acetyl, propionyl, butyryl, valeryl, 4 methylvaleryl, and acetoxy, acryloyl, and acryloyloxy.

The term "halogen" or "halo" means fluorine, chlorine, bromine, or iodine. The term "halohydrocarbyl" means a hydrocarbyl radical as defined above wherein one or more hydrogens is replaced with a halogen. A halohydrocarbyl radical (group or substituent) is typically a substituted alkyl substituent. Examples of such haloalkyl radicals include chloromethyl, 1-bromoethyl, fluoromethyl, difluoromethyl, trifluoromethyl, 1,1,1-trifluoroethyl, and the like.

The term "perfluorohydrocarbyl" means an alkyl group wherein each hydrogen has been replaced by a fluorine atom. Examples of such perfluorohydrocarbyl groups, in addition to trifluoromethyl above, are perfluorobutyl, perfluoroisopropyl, and perfluorohexyl.

The abbreviation "Ph" means a phenyl group ($C_6H_5$) group.

The phrase "True Fungi" is used herein for all of the fungal organisms discussed herein except for the Oomycota (such as *Pythium, Phytophthora* and *Plasmopara*). The uncaptialized term "fungi" or "fungus" is used to include all of the fungal organisms discussed herein, including the Oomycota.

In general, "pesticidal" means the ability of a substance to increase mortality, inhibit the growth rate, or eliminate the presence of plant pests. The term is used herein, to describe the property of a substance to exhibit activity against insects, mites, nematodes, fungi, bacteria, viruses, and/or phytopathogens. The term "pests" include insects, mites, nematodes, fungi, bacteria, viruses, and/or phytopathogens.

The term "health of a plant" or "plant health" is defined as a condition of the plant and/or its products. As a result of the improved health, yield, plant vigor, quality and tolerance to abiotic or biotic stress are increased. The health of a plant, when applying the active ingredients described herein, is increased independently of the pesticidal properties of the active ingredients used because the increase in health is not only based upon the reduced pest pressure but also on complex physiological and metabolic reactions that result, for example, in an activation of the plant's own natural defense system. As a result, the health of a plant is increased even in the absence of pest pressure.

"Insecticides" as well as the term "insecticidal" refers to the ability of a substance to increase mortality or inhibit growth rate of insects. As used herein, the term "insects" includes all organisms in the class "Insecta." The term "pre-adult" insects refers to any form of an organism prior to the adult stage, including, for example, eggs, larvae, and nymphs.

"Nematicides" and "nematicidal" refers to the ability of a substance to increase mortality or inhibit the growth rate of nematodes. In general, the term "nematode" comprises eggs, larvae, juvenile, and mature forms of said organism.

"Acaricide" and "acaricidal" refers to the ability of a substance to increase mortality or inhibit growth rate of ectoparasites belonging to the class Arachnida, sub-class Acari.

"Fungicide" and "fungicidal" refers to the ability of a substance to increase mortality, control or inhibit growth rate of Fungi. Fungicidal abilities may be preventative, curative, or a combination thereof.

By "effective" amount of an active ingredient, compound, drug, formulation, or permeant is meant a sufficient amount of an active agent to provide the desired local or systemic effect. A "topically effective" or "therapeutically effective" amount refers to the amount of compound or drug needed to effect the desired therapeutic result.

The term "agriculturally acceptable salt" is meant to include a salt of a compound of the invention which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert carrier. Examples of agriculturally acceptable base addition salts include sodium, potassium, calcium, ammonium, organic amino (such as choline or diethylamine or amino acids such as d-arginine, 1-arginine, d-lysine, or 1-lysine), or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The term "agriculturally acceptable excipient" is conventionally known to mean agriculturally acceptable carriers, agriculturally acceptable diluents and/or agriculturally acceptable vehicles used in formulating compositions effective for the desired use.

The term "agriculturally acceptable carrier" or "agriculturally acceptable vehicle" or "carrier" refers to any medium that provides the appropriate delivery of an effective amount of an active agent(s) as defined herein, does not negatively interfere with the effectiveness of the biological activity of the active agent, and that is sufficiently non-toxic to the host. The term is used herein to denote a natural or synthetic, organic, or inorganic material that constitutes a portion of the diluent medium in which the benzoxaborole is dispersed or dissolved. This carrier is inert and agriculturally acceptable, in particular to the plant being treated. The phrase "agriculturally acceptable" is utilized herein to be analogous to "pharmaceutically acceptable" as used in pharmaceutical products to describe diluent media. A carrier, agriculturally acceptable carrier, or agriculturally acceptable vehicle can be solid (clays, natural or synthetic silicates, silica, resins, waxes, solid fertilizers, and the like) or liquid (water, alcohols, ketones, petroleum fractions, aromatic or paraffinic hydrocarbons, chlorinated hydrocarbons, liquefied gases, and the like). In the presently disclosed formulations, carriers may be solid or liquid, and may comprise a Lewis base, or a N—H or O—H bond. Additional information concerning carriers can be found in Remington: The Science and Practice of Pharmacy, 21st Ed., Lippincott, Williams & Wilkins (2005), which is incorporated herein by reference.

The term "formulation" refers to a mixture that may be solid or liquid comprising a benzoxaborole and at least one of agriculturally acceptable carriers, solvents, adjuvants, wetting agents, surfactants, and the like. The term "formulation" refers both to concentrated formulations and diluted or applied formulations depending on the desired administration/application. Examples of formulations include: wettable powders (WP), water dispersible granules (WG or WDG), soluble concentrates (SL), suspension concentrates (SC), emulsifiable/emulsion-concentrates (EC), concentrated aqueous emulsions (EW), microemulsions (ME), suspoemulsion (SE), oil dispersions (OD), microencapuslted particles (CS), soil applied granule on inters or fertilizer carriers (GR), seed treatments, pre-mixes, tank-mixes, dosage formulations, etc.

The term "surfactant" or "surfactants" generally refers to compounds or substances that lower surface tension between two liquids, a gas and a liquid, or a liquid and a solid. Surfactants generally may act as surface active agents, wetting agents, dispersing agents, other adjuvants, and the like.

The term "Lewis Acid" refers to a compound or ionic species that can accept an electron pair from a donor compound (for example, a Lewis Base). A Lewis Acid is capable of accepting an electron pair from a Lewis Base to form a Lewis adduct.

The term "Lewis Base" refers to a compound or ionic species that can donate an electron pair to an acceptor compound (for example, a Lewis Acid). A Lewis Base is capable of donating an electron pair to a Lewis Acid to form a Lewis adduct.

Compounds

Benzoxaborole compounds and methods of using the benzoxaborole compounds are described herein. As will be discussed in greater detail below, exemplary embodiments of the compound are particularly useful in agricultural or therapeutic applications (e.g., as phytopathogenic and/or infectious agent control, growth enhancement or control).

In one embodiment, a benzoxaborole compound can be represented by formula (I):

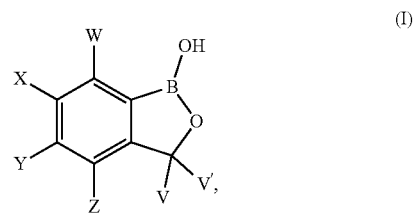

(I)

wherein:
W is selected from the group consisting of: hydrogen, halogen, $CH_3$, $CF_3$, Et, $OCH_3$, $OCF_3$, $OCF_2H$, $CFH_2$, OEt, O-n-propyl, O-n-butyl, O-iso-propyl, O-sec-butyl, O-iso-butyl, O-cyclopropyl, O-cyclbutyl, C(O)H, CN, $CH_2OH$, $SR^1$, and $S(O)R^1$, wherein $R^1$ is selected from C1-C3 hydrocarbyl;
X is selected from the group consisting of: hydrogen, $R^2$, $OR^2$, $OCF_2H$, $NR^2_2$, $NHR^2$, $NH_2$, halogen, $CO_2R^2$, CN, OH, $CH_2OH$, $NO_2$, C(O)H, $SR^2$, and $S(O)R^2$, wherein each $R^2$ is independently selected from C1-C7 hydrocarbyl and C3-C6 cyclohydrocarbyl or each $R^2$ can be taken together to form a ring;
Y is selected from the group consisting of: hydrogen, halogen, $CH_3$, $NO_2$, C(O)H, and $CO_2R^3$, wherein $R^3$ is selected from C1-C4 hydrocarbyl and C3-C4 cyclohydrocarbyl;
Z is selected from the group consisting of: hydrogen, halogen, $R^4$, $NR^4_2$, $NHR^4$, $NH_2$, $NO_2$, $CO_2R^4$, $OR^4$, OH, $OCF_2H$, $SR^4$, and $S(O)R^4$, wherein $R^4$ is selected from C1-C3 hydrocarbyl and C3 cyclohydrocarbyl; and
V and V' are independently selected from the group consisting of hydrogen and $CH_3$,
or a salt, stereoisomer, enantiomer, or tautomer thereof.

Exemplary embodiments of the benzoxaborole compound include the following:

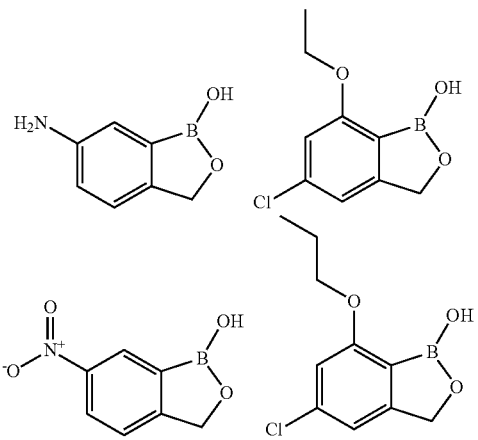

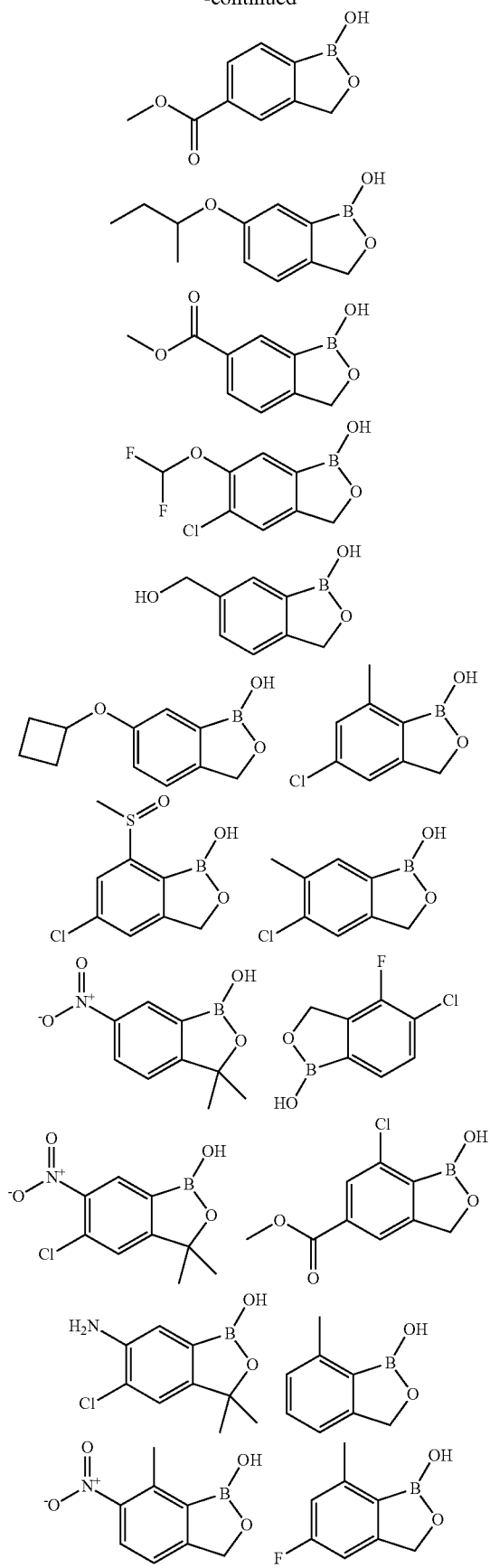
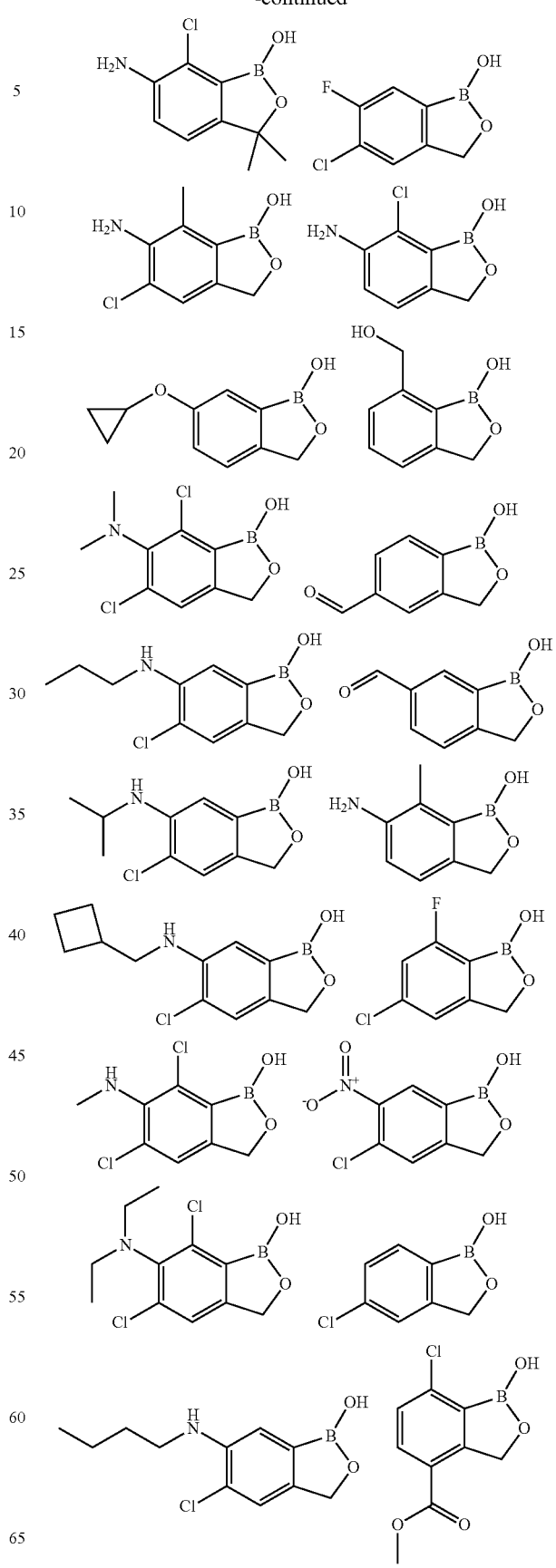

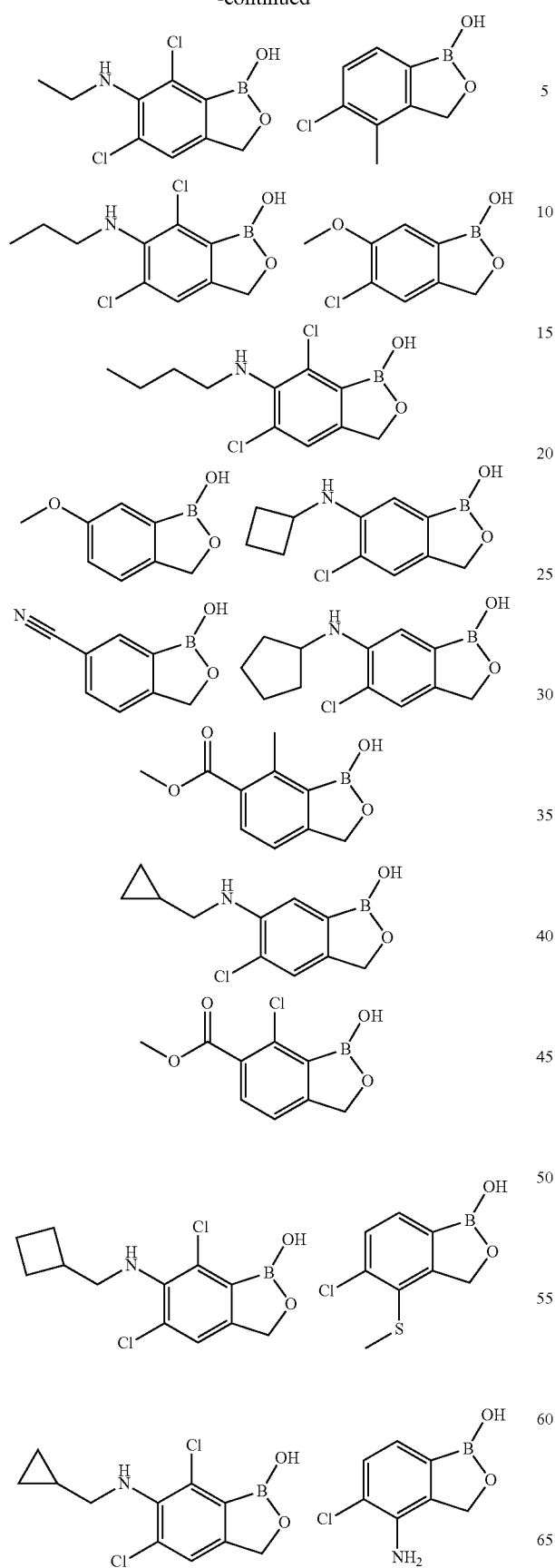
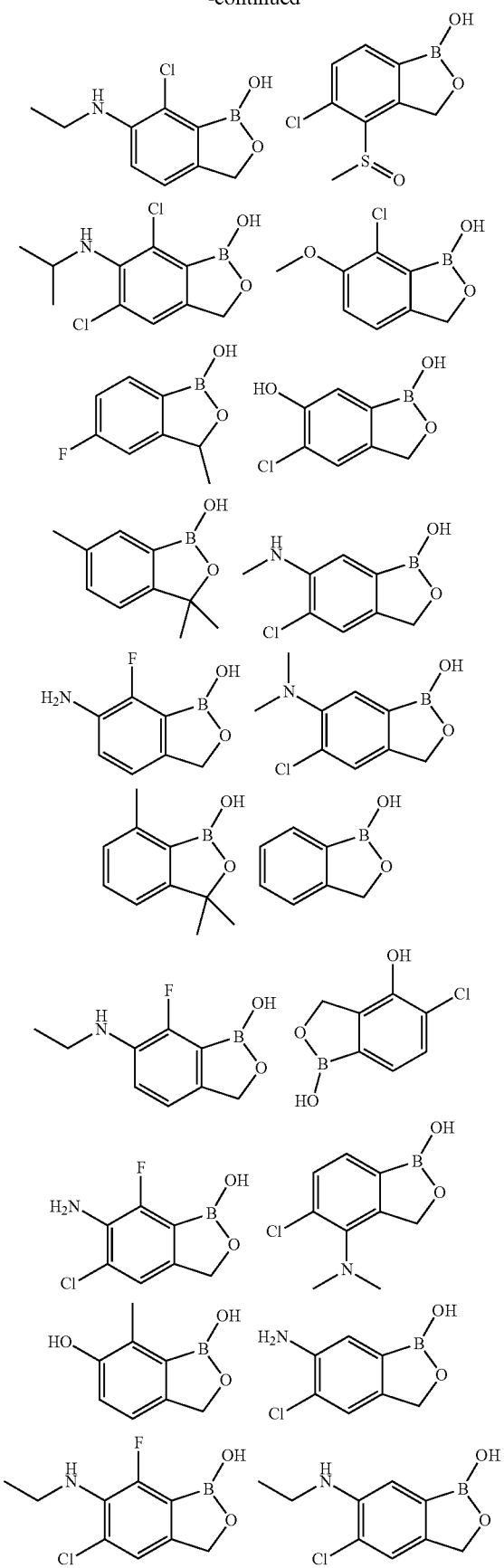

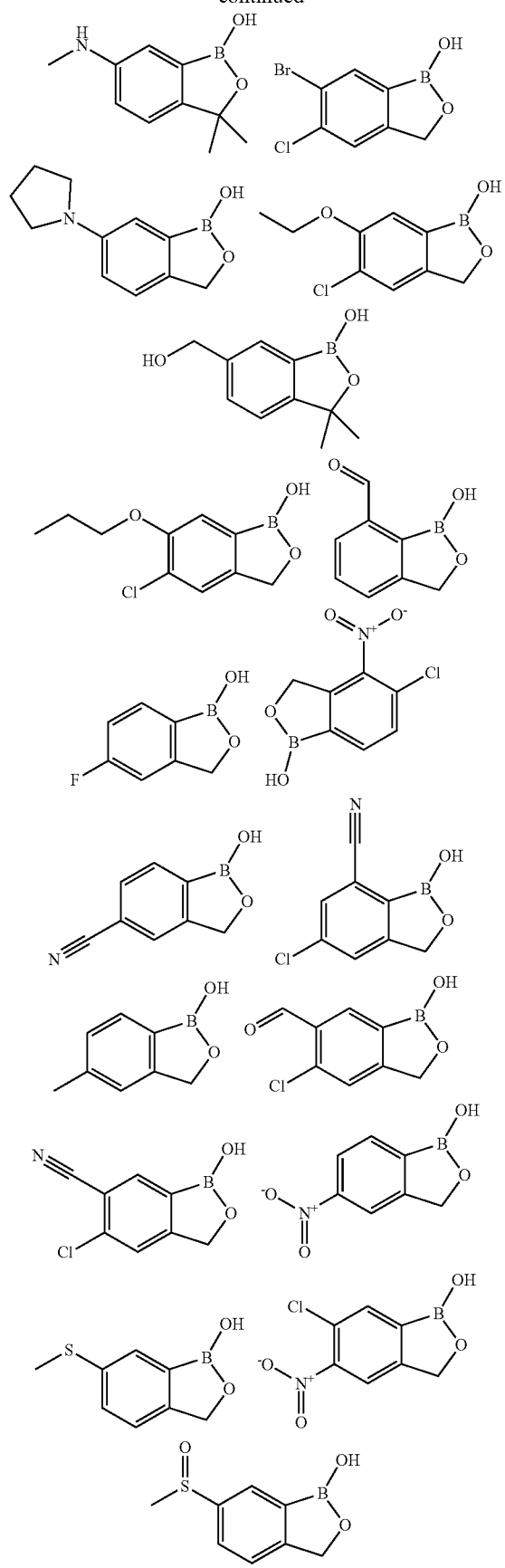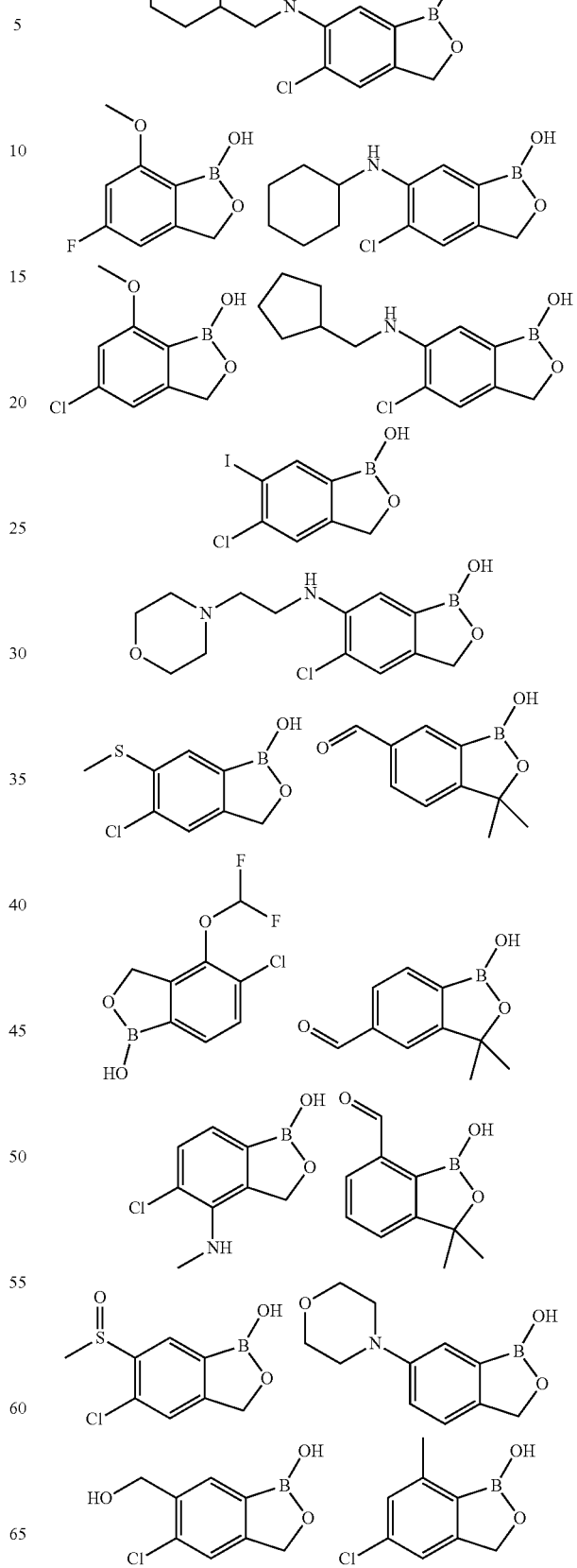

-continued

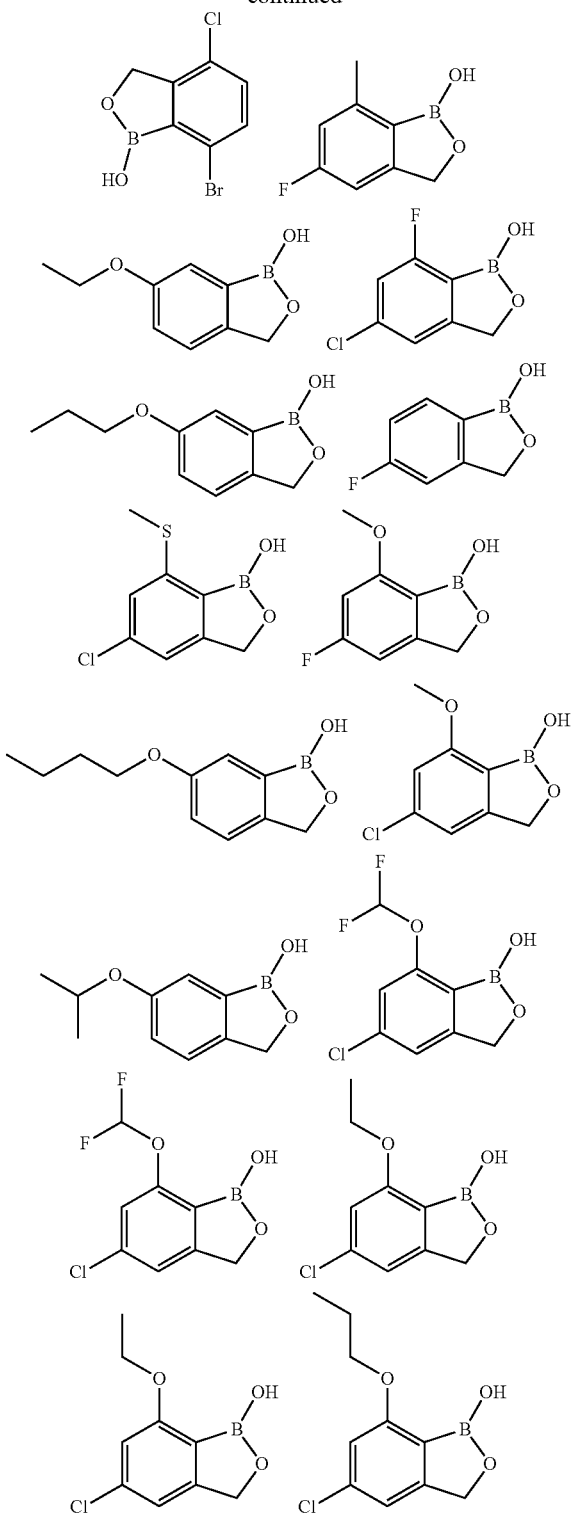

The above exemplary embodiments may also be or a salt, stereoisomer, enantiomer, or tautomer thereof.

In another embodiment, a benzoxaborole compound can be represented by formula (IaI):

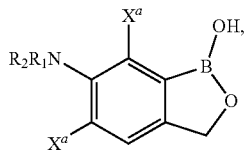

(IaI)

wherein:
R$_1$ is equal to R$_2$, or R$_1$ is not equal to R$_2$, and
R$_1$ and/or R$_2$ are selected from the group consisting of: hydrogen, methyl, ethyl, propyl, butyl, and pentyl, or
R$_1$ and R$_2$ are taken together to form a 3 to 6 membered ring, and
each X$^a$ is independently selected from the group consisting of: fluorine, chlorine, bromine, and iodine,
or a salt, stereoisomer, enantiomer, or tautomer thereof.

In another embodiment, a benzoxaborole compound can be represented by formula (IaII):

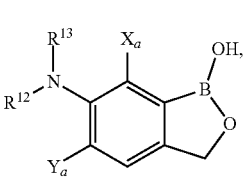

(IaII)

wherein:
each R$^{12}$ or R$^{13}$ is independently selected from the group consisting of hydrogen, methyl, ethyl, propyl, butyl, pentyl, C$_1$-C$_7$ hydrocarbyl, C3-C6 cyclohydrocabyl, —CH$_2$C≡CR$_4{}^a$, CH$_2$C≡CPh, CH$_2$C≡CCH$_2$Ph, and C$_1$-C$_7$ hydrocarbyl having 1-15 R$_4{}^a$ substitutions; or R$^{12}$ and R$^{13}$ may be taken together to form a 3 to 6 membered ring with the nitrogen atom to which they are bonded to;
X$^a$ is selected from the group consisting of: hydrogen, fluorine, chlorine, bromine, and iodine;
Y$_a$ is selected from the group consisting of hydrogen, fluorine, chlorine, bromine, and iodine, and
each R$_4{}^a$ is independently selected from the group consisting of alkyl, substituted alkyl, cyclopropyl and cyclobutyl,
or a salt, stereoisomer, enantiomer, or tautomer thereof.

In another embodiment, a benzoxaborole compound can be represented by formula (IaIII):

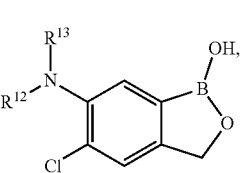

(IaIII)

wherein:
each R$^{12}$ or R$^{13}$ is independently selected from the group consisting of hydrogen, methyl, ethyl, propyl, butyl, pentyl, C1-C7 hydrocarbyl, C3-C6 cyclohydrocabyl, —CH$_2$C≡CR$_4{}^a$, CH$_2$C≡CPh, CH$_2$C≡CCH$_2$Ph, and C1-C7 hydrocarbyl having 1-15 R$_4{}^a$ substitutions; or $R^{12}$ and $R^{13}$ may be taken together to form a 3 to 6 membered ring with the nitrogen atom to which they are bonded to; and each $R_4{}^a$ is independently selected from the group consisting of: alkyl, substituted alkyl, cyclopropyl and cyclobutyl, or a salt, stereoisomer, enantiomer, or tautomer thereof.

In another embodiment, a benzoxaborole compound can be represented by formula (IaIV):

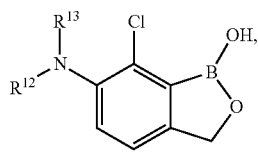

(IaIV)

wherein:

each $R^{12}$ or $R^{13}$ is independently selected from the group consisting of hydrogen, methyl, ethyl, propyl, butyl, pentyl, C1-C7 hydrocarbyl, C3-C6 cyclohydrocarbyl, —CH2C≡$CR_4{}^a$, $CH_2C$≡CPh $CH_2C$≡$CCH_2Ph$, and C1-C7 hydrocarbyl having 1-15 $R_4{}^a$ substitutions; or $R^{12}$ and $R^{13}$ may be taken together to form a 3 to 6 membered ring with the nitrogen atom to which they are bonded to;

each $R_4{}^a$ is independently selected from the group consisting of alkyl, substituted alkyl, cyclopropyl and cyclobutyl, or a salt, stereoisomer, enantiomer, or tautomer thereof.

In another embodiment, the disclosure includes a benzoxaborole formula (IaV):

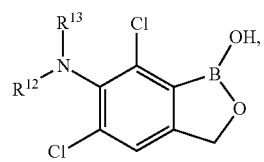

(IaV)

wherein:

each $R^{12}$ or $R^{13}$ is independently selected from the group consisting of hydrogen, methyl, ethyl, propyl, butyl, pentyl, C1-C7 hydrocarbyl, C3-C6 cyclohydrocarbyl, —CH2C≡$CR_4{}^a$, $CH_2C$≡CPh, $CH_2C$≡$CCH_2Ph$ and C1-C7 hydrocarbyl having 1-15 $R_4{}^a$ substitutions; or $R^{12}$ and $R^{13}$ may be taken together to form a 3 to 6 membered ring with the nitrogen atom to which they are bonded to;

each $R_4{}^a$ is independently selected from the group consisting of alkyl, substituted alkyl, cyclopropyl and cyclobutyl, or a salt, stereoisomer, enantiomer, or tautomer thereof.

Exemplary embodiments of the benzoxaborole compound are shown in Table A. Each compound in Table A can be represented by the formula (IaI). In some embodiments, the compound selected from Table A may be a salt, stereoisomer, enantiomer, or tautomer thereof.

TABLE A

Exemplary Embodiments of Benzoxaborole Compounds

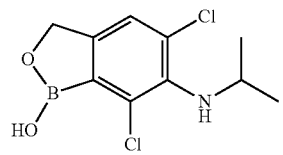 [SMILES: CC(C)Nc1c(Cl)cc2c(c1Cl)B(O)OC2]

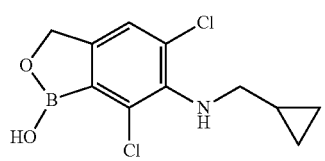 [SMILES: OB1OCc2cc(Cl)c(NCC3CC3)c(Cl)c21]

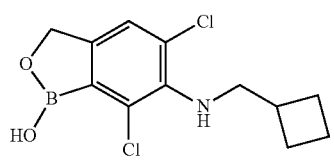

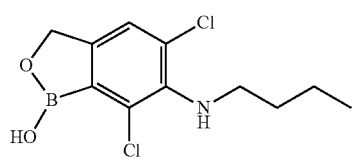 [SMILES: CCCCNc1c(Cl)cc2c(c1Cl)B(O)OC2]

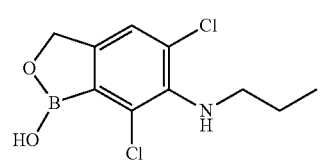 [SMILES: CCCNc1c(Cl)cc2c(c1Cl)B(O)OC2]

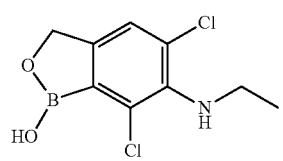

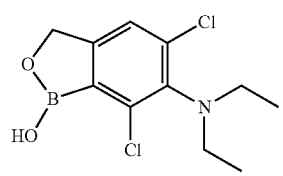 [SMILES: CCN(CC)c1c(Cl)cc2c(c1Cl)B(O)OC2]

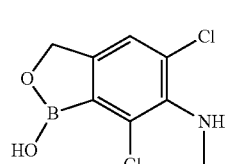

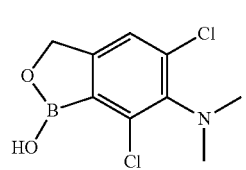

TABLE A-continued

Exemplary Embodiments of Benzoxaborole Compounds

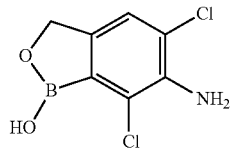

In yet another embodiment, a benzoxaborole compound can be represented by formula (Ib):

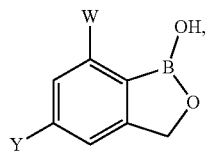

(Ib)

wherein Y is selected from the group consisting of: hydrogen, fluorine, chlorine, bromine, and iodine, and W is selected from the group consisting of: hydrogen, methyl, fluorine, chlorine, bromine, and iodine,
or a salt, stereoisomer, enantiomer, or tautomer thereof.

In another embodiment, of a benzoxaborole compound of formula (Ib) is an embodiment where W is hydrogen and Y is hydrogen or a salt thereof.

In another embodiment, of a benzoxaborole compound of formula (Ib) is an embodiment where W is hydrogen and Y is fluorine or a salt thereof.

An exemplary embodiment of a benzoxaborole compound of formula Ib is an embodiment wherein W is hydrogen and Y is chlorine or a salt thereof. This embodiment has a chemical name (IUPAC name) of 5-chlorobenzo[c][1,2]oxaborol-1(3H)-ol. This exemplary compound may be referred to herein as BAG8:

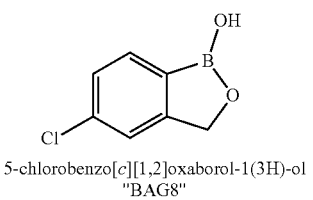

5-chlorobenzo[c][1,2]oxaborol-1(3H)-ol
"BAG8"

In another embodiment, a benzoxaborole compound can be represented by formula (Ic):

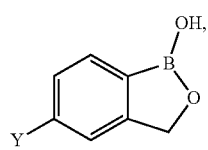

(Ic)

wherein Y is selected from the group consisting of: hydrogen, fluorine, chlorine, bromine, and iodine,
or a salt, stereoisomer, enantiomer, or tautomer thereof.

In another embodiment, a benzoxaborole compound can be represented by formula (Id):

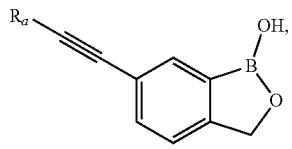

(Id)

wherein $R_a$ is selected from the group consisting of: methyl, ethyl, trimethylsilyl, isopropyl, and n-propyl,
or a salt, stereoisomer, enantiomer, or tautomer thereof.

In yet another embodiment, a benzoxaborole compound can be represented by formula (Ie):

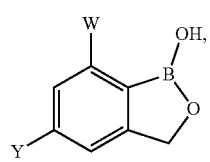

(Ie)

wherein Y is a halogen and W is selected from the group consisting of: OMe, OEt, O-n-Propyl, O-n-Butyl, $OCHF_2$.
or a salt, stereoisomer, enantiomer, or tautomer thereof.

In another embodiment, a benzoxaborole compound can be represented by formula (If):

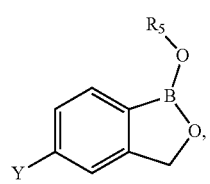

(If)

wherein $R_5$ is selected from the group consisting of: a C1-C15 hydrocarbyl, $CH_2Ph$, methyl, ethyl, isopropyl, n-propyl, n-butyl, iso-butyl, sec-butyl, n-pentyl, iso-pentyl, and n-decyl; and
Y is selected from the group consisting of: hydrogen, fluorine, chlorine, bromine, and iodine,
or a salt, stereoisomer, enantiomer, or tautomer thereof.

In another embodiment, a benzoxaborole compound can be represented by formula (Ig):

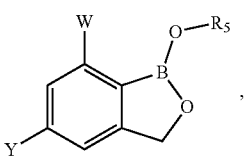

(Ig)

wherein $R_5$ is selected from the group consisting of: a C1-C15 hydrocarbyl, $CH_2Ph$, methyl, ethyl, isopropyl, n-propyl, n-butyl, iso-butyl, sec-butyl, n-pentyl, iso-pentyl, and n-decyl;
Y is selected from the group consisting of: hydrogen, fluorine, chlorine, bromine, and iodine; and
W is selected from the group consisting of: hydrogen, methyl, fluorine, chlorine, bromine, and iodine, or a salt, stereoisomer, enantiomer, or tautomer thereof.

Without being bound by theory, it is believed that when in aqueous media, embodiments of benzoxaborole compounds described herein may be present in a reversible equilibrium with water or other nucleophiles or other Lewis Bases due the Lewis acidic nature of the trigonal planar boron center (e.g. equilibrium between A and B below). This dynamic equilibrium may be important for the biological activity of various species of the benzoxaborole compounds described herein. Exemplary species may include compounds of formula (A) and formula (B) below.

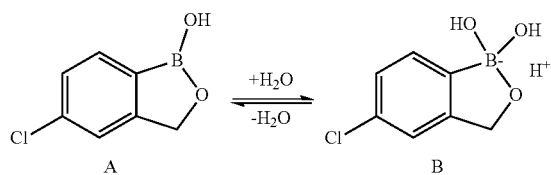

Benzoxaborole compounds may be present in free form, as a hydrate, as a salt, as a stereoisomer, as an enantiomer, or a tautomeric form; e.g., as an agronomically usable or an agrochemically acceptable salt form.

Methods of Use

The benzoxaborole compounds and the formulations comprising benzoxaborole compounds described herein can be useful in providing a method for reducing, preventing, ameliorating, or inhibiting an infestation by a pathogen. The pathogen may include insects, nematodes, bacteria, microbes, fungi, protozoa, viruses, parasites or any combinations thereof.

In another aspect, the benzoxaborole compounds and the formulations comprising them can be used in methods for reducing, preventing, ameliorating, or inhibiting an infestation by a pathogen by applying an effective amount of the compound or formulation, wherein the pathogen is a fungi.

In another aspect, the disclosure includes a method for reducing, preventing, ameliorating, or inhibiting an infestation by pests and/or a pathogen by applying a compound according to any one of the above formulae or a formulation of a compound according to any one of the above formulae, wherein the pathogen is a bacteria.

In another aspect, the disclosure includes a method for reducing, preventing, ameliorating, or inhibiting an infestation by pests and/or a pathogen by applying a compound according to any one of the above formulae or a formulation of a compound according to any one of the above formulae, wherein the pathogen is an insect, nematode, bacteria, microbe, fungi, protozoa, virus, parasite or any combinations thereof.

Benzoxaborole compounds, for example, a compound according to any one of the above formulae, can be used in a method for controlling or preventing an infestation of pests and/or a pathogen by treating a plant, plant part, plant propagation material, or seeds. The pathogen may be a bacteria, microbe, fungi, or any combination thereof. Additionally, formulations of benzoxaborole compounds can be used in the same manner for controlling or preventing an infestation of pests and/or a pathogen by treating a plant, plant part, plant propagation material, or seeds.

In general, bacterial pathogens may be classified as either gram-positive or gram-negative pathogens. Antibiotic compounds with activity against both gram-positive and gram-negative pathogens are generally regarded as having a broad spectrum of activity. The benzoxaborole compounds described herein are regarded as being active against gram-positive and/or gram-negative bacterial pathogens.

Examples of gram-positive and gram-negative aerobic and anaerobic bacteria, include Staphylococci, Enterococci, Streptococci, Bacilli, Listeria, Haemophilus, Moraxella, Mycobacteria, Staphylococci, Pseudomonas, *Agrobacterium tumefaciens*, and *Escherichia*.

Examples of fungi include: one or more members of the phyla of Ascomycota, Oomycota, Basidiomycota, and the subphylum Mucoromycotina.

The target fungi of the division Ascomycota include, for example, subdivision Pezizomycotina and Taphrinomycotina which include Dothideomycetes, Leotiomycetes, Sordariomycetes and Taphrinomycetes classes.

The target fungi of the phylum Ascomycota include, for example, subphylum selected from the group consisting of Dothideomycetes, Leotiomycetes, and Sordariomycetes.

The target fungi of the division Basidiomycota include, for example, subdivisions Agaricomycotina, Pucciniomycotina, and Ustilaginomycotina.

In some embodiments, the one or more target fungi whose growth is to be controlled or prevented is selected from one or more of the group consisting of *Zymoseptoria, Phaeosphaeria, Erysiphe, Blumeria, Sclerotinia, Botrytis, Cercospora, Alternaria, Verticillium, Fusarium, Magnaporthe, Colletotrichum, Phakopsora, Puccinia, Rhizoctonia, Pythium, Plasmopara, Phytophthora, Aspergillus, Bipolaris, Candida, Cochiobolus, Dilophospora, Exserohilum, Mycosphaerella, Sclerophthora, Ustiligo, Melampsora, Oidiopsis, Phymatotrichum, Pyrenophora, Uncinula, Peronospora, Monolinia, Venturia, Phomopsis, Claviceps, Aspergillus, Dibotryon, Pseudoperonospora, Setosphaeria,* and *Podosphaera*.

In some embodiments, the one or more target fungi whose growth is to be controlled or prevented is selected from one or more of the group consisting of *Zymoseptoria, Phaeosphaeria, Erysiphe, Blumeria, Sclerotinia, Botrytis, Cercospora, Alternaria, Verticillium, Fusarium, Magnaporthe, Colletotrichum, Phakopsora, Puccinia, Rhizoctonia, Pythium, Plasmopara, Phytophthora, Aspergillus, Bipolaris, Candida, Cochliobolus, Dilophospora, Exserohilum, Mycosphaeralla, Sclerophthora, Ustiligo, Melampsora, Oidiopsis, Phymatotrichum, Pyrenophora, Uncinula,* and *Peronospora*.

The benzoxaborole compounds demonstrate antipathogenic activity, good plant tolerance, low toxicity to plants, while exhibiting minimal environmental impact. The compounds are suitable for protecting seeds, plants, plant organs, and plant propagation material, for increasing harvest yields, for improving the quality and/or vigor of the harvested material, in protection of stored products and of materials. They can be employed as plant protection agents. Moreover, the benzoxaborole compounds and benzoxaborole formulations are active against normally sensitive and resistant species and against all or some stages of development.

Benzoxaborole Formulations

Formulations comprising a benzoxaborole compound are also described herein. As will be described more fully below, the benzoxaborole formulations have several benefits and advantages.

In a first embodiment, the benzoxaborole formulation comprises a benzoxaborole, a non-ionic surfactant or a non-ionic and ionic surfactant mixture, and a carrier. At least one of the non-ionic surfactant, the non-ionic and ionic surfactant mixture, and the carrier comprise a Lewis base or a N—H or O—H bond. The carrier can be a solid or a liquid.

In another embodiment, a method of using a benzoxaborole formulation comprises administering the formulation to seeds, plants, plant parts, and plant propagation materials in need thereof. The formulation comprises a benzoxaborole compound, a non-ionic surfactant or a non-ionic and ionic surfactant mixture, and a carrier. At least one of the non-ionic surfactant, the non-ionic and ionic surfactant mixture, and the carrier comprise a Lewis base or a N—H or O—H bond. The carrier can be a solid or a liquid.

A benzoxaborole formulation comprises the benzoxaborole compounds described herein; specifically, the benzoxaborole compounds represented by formulae (Ib) and (Ic).

In an exemplary embodiment, the benzoxaborole formulation comprises a benzoxaborole compound of formula (Ic):

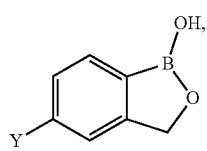

(Ic)

wherein Y is selected from the group consisting of: hydrogen, fluorine, chlorine, bromine, and iodine.

In another exemplary embodiment, the benzoxaborole formulation comprises a benzoxaborole compound of formula (Ic):

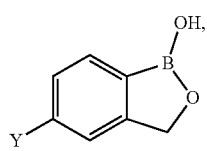

(Ic)

wherein Y is chlorine.

In yet another embodiment, the benzoxaborole formulation comprises a benzoxaborole compound of formula (Ib):

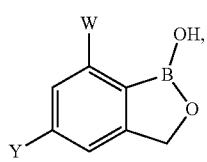

(Ib)

wherein:
Y is selected from the group consisting of: hydrogen, fluorine, chlorine, bromine, and iodine, and
W is selected from the group consisting of: hydrogen, methyl, fluorine, chlorine, bromine, and iodine.

Due to the Lewis Acidic character of the boron in the benzoxaborole compound, the boron can readily form a covalent bond with Lewis bases that may be present in the formulation. The Lewis base may be, for example, a solvent, a surfactant, a carrier, or an adjuvant.

In the benzoxaborole formulation, the boron of the benzoxaborole compound, for example, the boron of the benzoxaborole of formula (Ic) may react with alcohol solvents ($R_5OH$) present in the formulation to produce a benzoxaborole-alcohol adduct (a Lewis adduct). An example reaction to form a benzoxaborole-alcohol adduct is shown in Scheme 2.

Scheme 2.

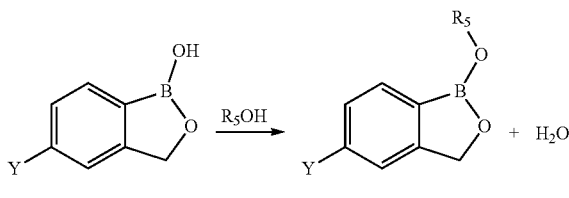

Exemplary alcohol solvents include, but are not limited to: $C_1$-$C_{15}$ branched saturated or unsaturated alcohols, $C_1$-$C_{15}$ linear saturated or unsaturated alcohols, benzyl alcohol, oleyl alcohol, cetyl alcohol, lauryl alcohol, 2-propanol, methanol, n-decanol, 1-propanol, ethanol, 1-hexanol, isobutyl alcohol, n-octanol, 1-butanol, pentanol, cyclohexanol, and mixtures thereof.

In another embodiment, the benzoxaborole formulation comprises a benzoxaborole compound of formula (If):

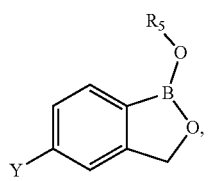

(If)

wherein the substituents are defined as shown above.

In the benzoxaborole formulation, the boron of the benzoxaborole compound, for example, the boron of the benzoxaborole of formula (Ib) may react with alcohol solvents ($R_5OH$) present in the formulation to produce a benzoxaborole-alcohol adduct (a Lewis adduct). An example reaction to form a benzoxaborole-alcohol adduct is shown in Scheme 2A.

Scheme 2A

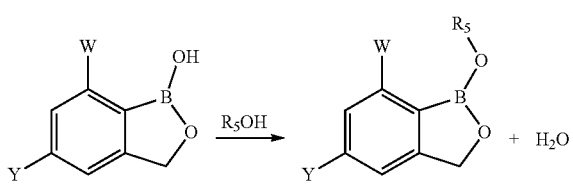

Exemplary alcohol solvents include, but are not limited to: $C_1$-$C_{15}$ branched saturated or unsaturated alcohols, $C_1$-$C_{15}$ linear saturated or unsaturated alcohols, benzyl alcohol, oleyl alcohol, cetyl alcohol, lauryl alcohol, 2-propanol, methanol, n-decanol, 1-propanol, ethanol, 1-hexanol, isobutyl alcohol, n-octanol, 1-butanol, pentanol, cyclohexanol, and mixtures thereof.

In another embodiment, the benzoxaborole formulation comprises a benzoxaborole compound of formula (Ig):

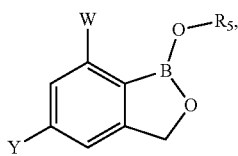

(Ig)

wherein the substituents are defined as shown above.

In another embodiment, the benzoxaborole formulation comprises a mixture of a benzoxaborole compound of formula (Ic) and a benzoxaborole compound of formula (If).

In another embodiment, the benzoxaborole formulation comprises a mixture of a benzoxaborole compound of formula (Ib) and a benzoxaborole compound of formula (Ig).

Exemplary benzoxaborole-alcohol adducts include the reaction products of (Ib) or (Ic) and the alcohol solvents listed herein. Example benzoxaborole compounds of formula (If) are shown below:

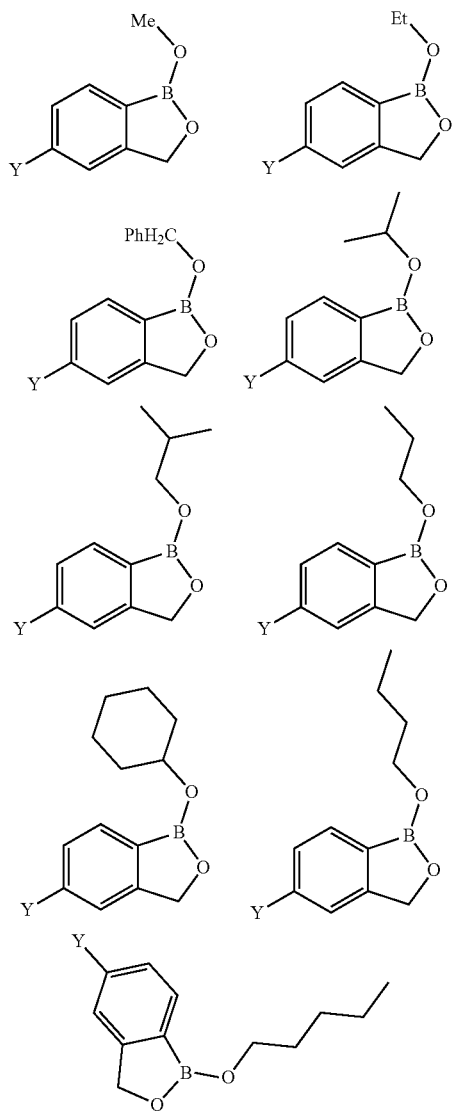

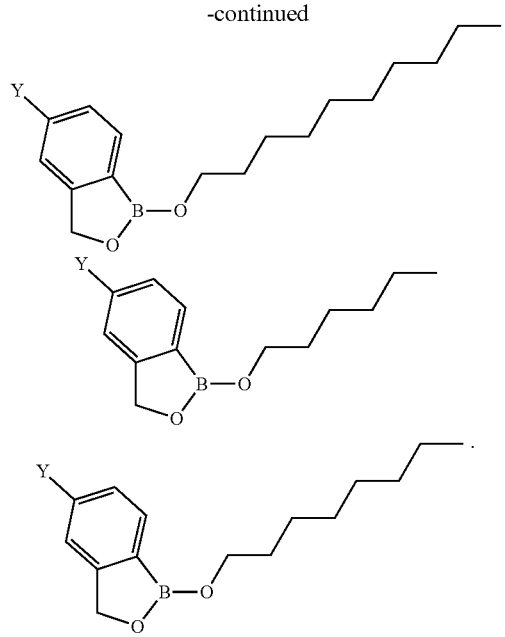

In some embodiments, the benzoxaborole compound of the benzoxaborole formulation may exist as an equilibrium mixture of the benzoxaborole and the benzoxaborole-alcohol adduct. In other embodiments, the benzoxaborole compound of the benzoxaborole formulation may exist as an equilibrium mixture of neutral planar benzoxaborole and ionic tetrahedral benzoxaborole. Exemplary equilibria are shown in Scheme 3. These dynamic equilibrium may be important for the biological activity of the compounds of formula (Ib) and formula (Ic).

Scheme 3.

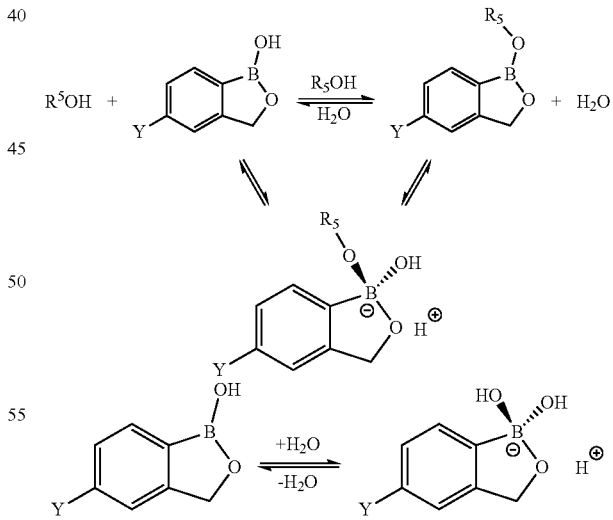

The benzoxaborole formulation may also comprise a second anti-fungal compound. The second anti-fungal compound may be selected from a group of compounds with a preselected biochemical mode of action (MOA) as described by a FRAC Target Site Code. Preferably, the FRAC Target site code is selected from the group consisting of: B, C, D, E, G, H, and M. More preferably, the second anti-fungal compound has a FRAC Target Site Code selected from one or more of a FRAC groups consisting of B1, B3, C3, C4, C6, D1, E1, E2, E3, G1, H5, M4, and M5. The FRAC Target Site Code single number designations are 1, 22, 11, 21, 30, 9, 13, 12, 2, 3, 40, M4, and M5, respectively.

In a preferred embodiment, the second anti-fungal compound comprises one or more of a compound selected from the group consisting of: carbendazim, thiabendazole, thiophanate, thiophanate-methyl, diethofencarb, zoxamide, ethaboxam, pencycuron, flupicolide, flutolanil, fluopyram, fluxapyroxad, penthiopyrad, benodanil, mepronil, isofetamid, fenfuram, carboxin, oxycarboxin, thifluzamide, benzovindiflupyr, bixafen, furametpyr, isopyrazam, penflufen, sedaxane, boscalid, benomyl, fuberidazole, diflumetorim, tolfenpyrad, azoxystrobin, coumoxystrobin, enoxastrobin, flufenoxystrobin, picoxystrobin, pyraoxystrobin, mandestrobin, pyraclostrobin, pyrametostrobin, triclopyricarb, kresoxim-methyl, trifloxystrobin, dimeoxystrobin, fenamistrobin, methominostrobin, orysastrobin, famoxadone, fluoxastrobin, fenamidone, pyribencarb, cyazofamid, amisulbrom, binapacryl, meptyldinocap, dinocap, fluazinam, fentin chloride, fentin acetate, fentin hydroxide, silthiofam, ametoctradin, cyprodinil, mepanipyrim, pyrimethanil, kasugamycin, quinoxyfen, proquinazid, fenpiclonil, fludioxonil, chlozolinate, dimethachlone, iprodione, procymidone, vinclozolin, triforine, pyrifenox, pyrisoxazole, fenarimol, nuarimol, imazalil, oxpoconazole, pefurazoate, prochloraz, triflumizole, azaconazole, bitertanol, bromuconazole, cyproconazole, diniconazole, epoxiconazole, etanconazole, fenbuconazole, fluquinconazole, flusilazole, flutriafol, hexaconazole, imibenconazole, ipconazole, metconazole, myclobutanil, penconazole, propiconazole, simeconazole, tebuconazole, tetraconazole, triadimefon, triadimenol, triticonazole, prothioconazole, aldimorph, dodemorph, fenpropimorph, tridemorph, fenpropidin, piperalin, spiroxamine, fenhexamid, fenpyrazamine, pyributicarb, naftifine, terbinafine, validamycin, polyoxin, dimethomorph, flumorph, pyrimorph, benthiavalicarb, iprovalicarb, valifenalate, mandipropamid, ferbam, macozeb, maneb, metiram, propineb, thiram, zineb, ziram, captan, captafol, folpet, dichlofluanid, tolylfluanid, and chlorothalonil.

The formulations described herein can be used to control many pathogens including fungi, bacteria, insects, and parasites for the benefit of seeds, plants, plant parts, and/or plant propagation material. The formulation or applied formulation may be administered systemically, topically, in the soil, as a seed treatment, or foliarly. In other embodiments, the formulation or applied formulation may be applied in any desired manner, such as in the form of a seed coating, soil drench, and/or directly in-furrow and/or as a foliar spray and applied either pre-emergence, post-emergence or both. In other words, the formulation can be applied to the seed, the plant or to harvested fruits and vegetables or to the soil, wherein the plant is growing or wherein it is desired to grow (i.e., the plant's locus of growth).

In some embodiments, the formulation is applied postharvest by dipping, fogging, drenching, or soil drenching.

In some embodiments, the treatment of plants or plant parts (which includes seeds and plants emerging from the seed) and/or harvested fruits and vegetables with the benzoxaborole formulation according to the invention is carried out directly or by action on their surroundings, habitat or storage space using customary treatment methods, for example dipping, spraying, atomizing, irrigating, evaporating, dusting, fogging, broadcasting, foaming, painting, spreading-on, watering (drenching), drip irrigating.

In a preferred embodiment, the formulation or applied formulation is applied foliarly.

The formulations may be selected from the following types of formulations: emulsifiable concentrates, coatable pastes, dilute emulsions, wettable powders, soluble powders, dusts, granulates, concentrated aqueous emulsions, suspension concentrates, oil dispersions, water dispersible granules, seed treatments, and also encapsulations/microencapsulations e.g. in substances. The formulations described herein may be directly sprayable. The formulations can also be further diluted to produce an applied formulation prior to being applied on plants or plant propagation materials. In some instances, the formulation is mixed with water to obtain the applied formulation. As with the type of the formulations, the methods of application, such as spraying, atomizing, dusting, scattering, coating or pouring, are chosen in accordance with the intended objectives and the prevailing circumstances. A contemplated formulation can also contain further components such as stabilizers, antifoams, viscosity regulators, binders or tackifiers as well as fertilizers, micronutrient donors, or other formulations or active ingredients for obtaining special effects.

Suitable diluent media and adjuvants (auxiliaries) for the formulation can be solid or liquid and are substances useful in formulation technology, e.g., natural or regenerated mineral substances, carriers, solvents, dispersants, wetting agents, tackifiers, thickeners, binders, or fertilizers. Such diluent media are for example described in WO 97/33890, which is hereby incorporated by reference. In the applied formulation, water-based (more than 50 weight percent water) diluent media are presently preferred and are used illustratively herein.

More particularly, the applied formulation can be employed in any conventional form, for example in the form of a powder, an emulsion, a microemulsion, a flowable concentrate, a solution, a suspension, a water dispersible powder, a capsule suspension, a gel, a cream, an emulsion concentrate, a suspension concentrate, a suspo-emulsion (an emulsion containing both solid and liquid benzoxaborole agents in an aqueous medium), a capsule suspension, a water dispersible granule, an emulsifiable granule, a water in oil emulsion, an oil in water emulsion, a micro-emulsion, an oil dispersion, an oil miscible liquid, a soluble concentrate, an ultra-low volume suspension, an ultra-low volume liquid, a technical concentrate, a dispersible concentrate, a wettable powder, or any technically feasible formulation.

The benzoxaborole formulations can be produced by one of skill in the art of boron-chemistry, e.g., by mixing the active ingredients with appropriate formulation inerts such as solid or liquid carriers and optional other formulating ingredients such as surface-active compounds (surfactants), biocides, anti-freeze agents, stickers, thickeners and compounds that provide adjuvancy effects, and the like. Also, conventional slow release formulations can be employed where long-lasting efficacy is intended. Particularly, applied formulations may be applied in spraying forms, such as water dispersible concentrates, wettable powders, emulsifiable concentrates, suspension concentration and granules, can contain surfactants such as wetting and dispersing agents and other compounds that provide adjuvancy effects.

Carriers may be solid or liquid, and may comprise a Lewis base, or a N—H or O—H bond.

Solid, particulate carriers that can be used, for example for dusts and dispersible powders, are kaolinite, lactose, calcite, talc, kaolin, diatomaceous earth, montmorillonite or attapulgite, highly-disperse silica, or absorptive polymers. Illustrative particulate, adsorptive carriers for granules include kaolinite, lactose, pumice, crushed brick, sepiolite or bentonite, montmorillonite-type clay, and exemplary non-sorbent carrier materials are calcite or dolomite. A particulate solid formulation can also be prepared by encapsulation of a suitable mixture of fungicides, pesticides, or insecticides or by a granulation process that utilizes one or more of the above diluents or an organic diluent such as microcrystalline cellulose, rice hulls, wheat middlings, saw dust and the like. Ilustrative granules can be prepared as discussed in U.S. Pat. Nos. 4,936,901, 3,708,573 and 4,672,065.

Suitable liquid carriers include: protic solvents, aprotic solvents, water, substituted aromatic hydrocarbons, in particular the fractions $C_8$-$C_{12}$, such as xylene mixtures or substituted naphthalenes, phthalic esters such as dibutyl or dioctyl phthalate, substituted aliphatic hydrocarbons such as limonene, alcohols and glycols as well as their ethers and esters such as ethylene glycol monomethyl ether, $C_1$-$C_{15}$ branched alcohols, $C_1$-$C_{15}$ linear alcohols, benzyl alcohol, oleyl alcohol, cetyl alcohol, lauryl alcohol, 2-propanol, methanol, n-decanol, 1-propanol, ethanol, 1-hexanol, isobutyl alcohol, n-octanol, 1-butanol, pentanol, cyclohexanol, and mixtures thereof, ketones such as cyclohexanone or isophorone, strongly polar solvents such as N-methyl-2-pyrrolidone, dimethyl sulfoxide or dimethylformamide, and, if appropriate, and epoxidized vegetable oils such as soybean oil. If appropriate, the liquid carrier can be a naturally occurring essential oil, such as oils from citronella, castor, lemon, citrus fruits, and lemon grass. In a preferred embodiment, the liquid carrier comprises a Lewis Base such as a protic solvent. In a preferred embodiment, the liquid carrier comprises a Lewis Base such as an alcohol.

In a preferred embodiment, the liquid carrier is a mixture comprising more than one suitable liquid carrier. In another preferred embodiment, the liquid carrier comprises a protic solvent or at least one alcohol selected from the group consisting of: $C_1$-$C_{15}$ branched alcohols (saturated or unsaturated), $C_1$-$C_{15}$ linear alcohols (saturated or unsaturated), benzyl alcohol, oleyl alcohol, cetyl alcohol, lauryl alcohol, 2-propanol, methanol, n-decanol, 1-propanol, ethanol, 1-hexanol, isobutyl alcohol, n-octanol, 1-butanol, pentanol, cyclohexanol, and mixtures thereof. In another preferred embodiment, the liquid carrier comprises at least one protic solvent and at least one aprotic solvent. Preferably, the aprotic solvent is polar. In another preferred embodiment, the liquid carrier comprises a protic solvent, a polar aprotic solvent, and a non-polar aprotic solvent.

A polar aprotic solvent, as defined herein, has a relatively large dielectric constant and a relatively large dipole moment, but it does not participate in hydrogen bonding (i.e., no O—H or N—H bonds). Exemplary polar aprotic solvents include acetone, N,N-dimethylformamide (DMF), acetonitrile (MeCN), and dimethyl sulfoxide (DMSO), N-methyl-2-pyrrolidone (NMP), cyclohexanone, and isophorone.

A non-polar aprotic solvent, as defined herein, has a relatively small dielectric constant and a relatively small dipole moment. Exemplary non-polar aprotic solvents include aliphatic hydrocarbons, aromatic hydrocarbons, substituted aromatic hydrocarbons, xylene mixtures, substituted naphthalenes, substituted aliphatic hydrocarbons, limonene (single enantiomer or mixtures thereof), or a mixture thereof.

As defined herein, protic solvents are solvents that have a hydrogen atom bonded to an oxygen (i.e. comprises an O—H bond) or a nitrogen (i.e. comprises an N—H bond). Exemplary protic solvent include: $C_1$-$C_{15}$ branched alcohols, $C_1$-$C_{15}$ linear alcohols, benzyl alcohol, oleyl alcohol, cetyl alcohol, lauryl alcohol, 2-propanol, methanol, n-decanol (decyl alcohol), 1-propanol, ethanol, 1-hexanol, isobutyl alcohol, n-octanol, 1-butanol, pentanol, cyclohexanol, and mixtures thereof.

Suitable surface-active compounds (or surfactants) comprise non-ionic or ionic surfactants (cationic and/or anionic), may be a Lewis Base, may comprise an N—H bond, may comprise on O—H bond, and have good emulsifying, dispersing and wetting properties, depending mostly on the nature of the active ingredients. The term "surfactants" is also to be understood as meaning mixtures of at least one surfactant.

The surfactants customarily employed in formulation technology are described, inter alia, in the following publications: *McCutcheon's Detergents and Emulsifiers Annual*, MC Publishing Corp., Glen Rock, N.J., 1988; M. and J. Ash, *Encyclopedia of Surfactants*, Vol. I-III, Chemical Publishing Co., New York, 1980-1981.

At least one surfactant is often present when inert vehicles and/or carriers are not readily soluble in water. In a preferred embodiment, the surfactant is at least one of a(n): amine ethoxylates, alkylaryl sulphonates, alkylbenzene sulphonates, calcium alkylaryl sulphonates, castor oil ethoxylates and polyethylene glycol derivatives of hydrogenated castor oil (for example PEG 40 castor oil hydrogenated), sorbitan fatty acid ester ethoxylates, polyoxyethylene sorbitan monolaurates (for example polysorbate 20), sorbitan fatty acid esters such as sorbitan monolaurate and sorbitan monostearate, polyoxyethylene polyoxypropylene sorbitan monolaurates, sorbitan fatty acid esters, non-ionic ethoxylates, branched and unbranched secondary alcohol ethoxylates, nonylphenol ethoxylates, and octylphenol ethoxylates.

Moreover, preferred non-ionic surfactants include, but are not limited to, fatty alcohol ethoxylates, alkyl phenol ethoxylates, castor oil based ethoxylates (for example PEG 40 castor oil hydrogenated), sorbitan fatty acid ester ethoxylates, polyoxyethylene sorbitan monolaurates (for example polysorbate 20), sorbitan fatty acid esters such as sorbitan monolaurate and sorbitan monostearate, polyoxyethylene polyoxypropylene sorbitan monolaurates, fatty acid ethoxylates, EO-PO block co-polymers, acrylic co-polymers, styrene acrylic polymers, polyalkylene oxide block copolymers, sorbitan(ol) ester ethoxylates, sarcosinates, alkyl polysaccharides, alkyl amine ethoxylates, amine oxides, siliconics, ethoxylated Graft & Comb polymers, and propoxylated and non-ethoxylated Graft & Comb polymers.

Additionally, preferred ionic surfactants include, but are not limited to, calcium alkylaryl sulphonates, alkylaryl sulphonates, alkylbenzene sulfphonates, alkyl ether phosphates, alkyl phenol ether phosphates, alkyl phenol ether sulphates, condensed naphthalene sulfonates and salts, sodium alkyl naphthalene sulphonate blends, sodium naphthalene sulphonate condensate, sodium alkylnaphthalene sulfonate, sodium alkylnapthalene formaldehyde condensates, aromatic hydrocarbon sulfonic acids, aromatic hydrocarbon sulfonic salts, aromatic hydrocarbon sulfonic blends, fatty alcohol sulphates, alkyl ether carboxylic acids, alkyl ether carboxylic salts, alkyl ether sulphates, monosulphosuccinates, polysulphosuccinates, alkyl phosphates, alkyl benzene sulphonic acids, alkyl benzene sulphonic salts, lignosulphonates and salts, and alpha olefin sulphonates.

Additionally, preferred non-ionic surfactants include, but are not limited to castor oil based ethoxylates (for example PEG 40 castor oil hydrogenated), fatty acid ester ethoxylates such as Tween 21, Tween 20, Tween 85, Tween 60, and Tween 22, polyoxyethylene sorbitan monolaurates (such as Tween 20, Tween 21, Tween 22), sorbitan fatty acid ester ethoxylates (such as Tween 20, Tween 21), polyoxyethylene sorbitan monostearates (such as Tween 60), polyoxyethylene sorbitan trioleates (such as Tween 85), and sorbitan fatty acid ester ethoxylates (such as Tween 85), high molecular weight polymeric emulsifiers such as the star polymer ATLOX 4916, and sorbitan monolaurate. Exemplary preferred non-ionic surfactants include, for example, Tween 21, Tween 22, Tween 20, Tween 60, Tween 85, ATLOX 4916, and Span 20.

Preferred ionic surfactants include, but are not limited to calcium alkylaryl sulphonates, for example ATLOX 4838B.

Furthermore, particularly useful adjuvants, which enhance application, are natural or synthetic phospholipids from the series of the cephalins and lecithins, for example phosphatidylethanolamine, phosphatidylserine, phosphatidylglycerine, or lysolecithin.

A contemplated formulation can also include at least one polymer that is a water-soluble or a water-dispersible, film-forming polymer that improves the adherence of the benzoxaborole compound to the treated material (e.g., seeds, plants, plant parts, or plant propagation materials). In one preferred embodiment where the benzoxaborole compound is used to treat plant propagation material, the polymer is a styrene acrylic emulsion polymer.

Some contemplated formulations can include at least one antioxidant. Examples of antioxidants include, but are not limited to: glycine, glycinebetaine, choline salts, in particular choline chloride, 2(3)-tert-butyl-4-hydroxyanisole (BHA), tert-butylhydroxyquinone (TBHQ), dilauryl thiodipropionate (DLTDP), tris(nonylphenyl))phosphite (TNPP), 2,6-dihydroxybenzoic acid (DHBA), acetylsalicylic acid (ASA), salicylic acid (SA), Irganox 1076 (Ciba Geigy), Ethanox 330 (Ethyl Corp.), Tinuvin 144 (Ciba Geigy), Ambiol (2-methyl-4-[dimethylaminomethyl]-5-hydroxybenzimidazole), propyl gallate, trihydroxybutyrophenone (THBP), thiodipropionic acid and dilauryl thiodipropionate, betaines (see, AU-B-27071/95 to Bodapati, and EO 0 493 670 A1 to Lunkenheimer et al.), amines (aromatic amines and hindered amines), methionine, cysteine, proline, mannitol, phosphites, thioesters, lecithin, gum or resin guiac, Vitamin E, polyphenols, Vitamin A, carotenoids (beta-carotene), Vitamin B, Vitamin C, tocopherols, alpha-lipoic acid, coenzyme Q10 CoQ10), grape seed extract, green tea, lutein, N-acetyl Cysteine (NAC), OPCs (pycnogenols), selenium, zinc, 2,6-di-tert-para-benzoquinone, abscisic acid, bioflavonoids, DMAE (N,N-Dimethylethanolamine, precursor of choline), metronidazole, 2-methyl-5-nitroimidazole, glyoxal, polymerized 2,2,4-trimethyl-1,2-dihydroquinoline, 2-mercaptobenzimidazol, 5-tert-butyl-4-hydroxy-2-methylphenyl sulfide (CAS RN 96-69-5), 4-tert-butylphenol (CAS RN 98-54-4), catechol (CAS RN 120-80-9), 2-naphthol (2-hydroxynaphthalene) (CAS RN 135-19-3), octadecyl-3-(3',5'-di-tert-butyl-4-hydroxyphenyl)propionate (CAS RN 2082-79-3), 1,3,5-trimethyl-2,4,6-tris(3,5-di-tert-butyl-4-hydroxybenzyl)benzene (CAS RN 1709-70-2), and tris-(2, 4,-di-tert-butylphenyl)phosphite (CAS RN 31570-04-4).

In some embodiments, hindered phenol antioxidants are preferred. Examples of hindered phenol antioxidants include: 2,6-di-tert-butyl-p-cresol (BHT) (CAS RN 128-37-0), 2(3)-tert-butyl-4-hydroxyanisole (BHA), isobutylenated methylstyrenated phenol (CAS RN 68457-74-9), styrenated phenol (CAS RN 61788-44-1), 2,6-di-tert-butyl-4-(octadecanoxycarbonylethyl)phenol (CAS RN 2082-79-3), 4,4'-thiobis-6-(t-butyl-m-cresol) (CAS RN 96-69-5), 4,4'-butylidenebis(6-t-butyl-m-cresol) (CAS RN 85-60-9), 4,4'-(1-methylethylidene)bis[2-(1,1-dimethylethyl)]phenol (CAS RN 79-96-9), 2,2'-methylenebis(4-methyl-6-nonyl)phenol (CAS RN 7786-17-6), 4-methyl-phenol reaction products with dicyclopentadiene and isobutylene (CAS RN 68610-51-5), tetrakis-(methylene-(3,5-di-tertbutyl-4-hydrocinnamate)methane (CAS RN 6683-19-8), tert-butylhydroxyquinone (TBHQ), Irganox 1076, Ethanox 330, and 1,3,5-tris(3,5-di-tert-butyl-4-hydroxybenzyl-)-1,3,5-triazine-2,4,6 (1H,3H,5H)-trione (CAS RN 27676-62-6).

Typically, a coloring agent, such as a dye or pigment, is included in the formulation so that an observer can immediately determine that the plant has been treated. An antifungal formulation that includes a coloring agent is a preferred embodiment of the invention as it can improve user and consumer safety. The coloring agent is also useful to indicate to the user the degree of uniformity of application. Generally, the coloring agent tends to have a melting point above 30° C., and therefore, is suspended in a contemplated formulation. The coloring agent can also be a soluble compound.

Examples of coloring agents include pigment red 48-2 (CAS-7023-61-2), pigment blue 15 (CAS-147-14-8), pigment green 7 (CAS-1328-53-6), pigment violet 23 (CAS-6358-30-1), pigment red 53-1 (CAS-5160-02-1), pigment red 57-1 (CAS 5281-04-9), pigment red 112 (CAS 6535-46-2) or similar coloring agents. A coloring agent is typically present at about 0.1 to about 10% by mass of the formulation.

In typical use, the benzoxaborole formulation composition is preferably formulated as a concentrate also known as a pre-mix composition (or concentrate, formulated compound, or formulation), and the end user normally employs a diluted formulation or an applied formulation for administration to the plants, plant propagation material, seeds, or plant parts of interest. Such a diluted formulation is often referred to as a tank-mix composition or an applied formulation. A tank-mix composition or applied formulation is generally prepared by diluting a pre-mix or formulation comprising a benzoxaborole compound with a diluent such as water that can optionally also contain further auxiliaries. Generally, an aqueous tank-mix is preferred.

In general, a benzoxaborole formulation, in particular an emulsion concentrate, includes about 0.01 to about 90% by weight benzoxaborole, about 0 to about 20% agriculturally acceptable surfactant and 1 to 99.99% solid or liquid carriers and adjuvant(s). For example, the formulation may include about 0.01 to 60 wt %, about 1.0 to 60 wt %, about 1.0 to 50 wt %, about 1.0 to 30 wt %, about 1.0 to 10 wt %, about 5.0 to 60 wt %, about 10 to 60 wt %, about 20 to 60 wt %, about 5 to 20 wt %, or about 20 to 40 wt % benzoxaborole. The formulation may include up to about 20%, up to about 15%, up to about 10%, or up to about 5% surfactant. The formulation may include about 1 to 99%, about 40 to 99%, about 50 to 99%, about 60 to 95%, about 70 to 95%, or about 80 to 99% solid or liquid carriers and agriculturally acceptable surfactant.

As will be shown in the examples below, in some instances, the formulation components enhance the biological or pesticidal activity of the benzoxaborole compound. For example, the formulation components may enhance the biological activity of the benzoxaborole compound.

Additionally, in exemplary instances, some formulation components aid in formulation stability. Moreover, in exemplary instances, some formulation components aid in applied formulation stability. For example, as shown in the examples below, having a suitable mixture of protic solvent and aprotic solvent as formulation components in an emulsifiable concentrate can be helpful in achieving a stable emulsion. As explained above, a protic solvent is a Lewis Base, for example, an alcohol. A protic solvent is also a solvent that has a hydrogen atom bound to an oxygen or a nitrogen. Moreover, it was also previously explained that a preferred embodiment of the formulation includes a liquid carrier comprising at least one protic solvent and at least one aprotic solvent. Additionally, having a suitable mixture of protic and aprotic solvent can be helpful in achieving an emulsion with a desirable $D_{90}$ particle size.

The ratio of protic solvent to aprotic solvent can vary. In embodiments, the ratio of protic solvent to aprotic solvent can be from about 20 to about 0.1. For example, the ratio can be from about 15 to about 0.25, from about 7 to about 0.25, from about 3 to about 0.25, or from about 1 to about 0.25. In other embodiments, the ratio of protic to aprotic solvent can be about 0.25, about 0.33, about 0.5, about 1, about 3, about 7, or about 15. In preferred embodiments, the ratio of protic to aprotic solvent is from about 1 to about 0.25, in particular, from about 1 to about 0.33.

The desirable $D_{90}$ particle size varies and is dependent on the formulation type. For example, a desired particle size for an emulsion that is derived from an emulsion concentrate that has been diluted into water is less than about 10 µm, less than about 5 µm, less than about 1 µm, or between about 0.1 µm and 1.0 µm. For diluted emulsion concentrates/emulsions derived from emulsion concentrates, it is generally desirable for the $D_{90}$ particle size to remain stable for the period of time within which the formulation would be applied by an end user. For example, it is desirable for the $D_{90}$ to remain stable for time periods up to 24 hours after dilution of the EC formulation into water.

In other exemplary instances, the formulation components aid in solubility.

In other exemplary instances, the formulation components enhance the shelf life or shelf stability of the formulation. For example, it is also desirable for the $D_{90}$ of the emulsion to be about the same when the emulsion concentrate is stored at room temperature (about 20° C.), higher temperature (about 50° C.), or lower temperature (about 0° C.).

Additionally, for some formulations, the biological activity of the benzoxaborole formulation is higher than the biological activity of the same benzoxaborole compound alone. For example, a BAG8 compound may be more biologically active in a formulation than it is alone. While not being bound by theory, it is possible that the formulation components increase the biological activity of the benzoxaborole compound.

Suitable penetrants that may be used in the present context include all those substances which are typically used in order to enhance the penetration of active agrochemical compounds into plants. Penetrants in this context are defined in that, from the (generally aqueous) application liquor and/or from the spray coating, they are able to penetrate the cuticle of the plant and thereby increase the mobility of the active compounds in the cuticle. This property can be determined using the method described in the literature (Baur et al., 1997, Pesticide Science 51, 131-152). Examples include alcohol alkoxylates such as coconut fatty ethoxylate, or isotridecyl ethoxylate, fatty acid esters such as rapeseed or soybean oil methyl esters, fatty amine alkoxylates such as tallowamine ethoxylate, or ammonium and/or phosphonium salts such as ammonium sulphate or diammonium hydrogen phosphate, for example.

The benzoxaborole content of the application forms prepared from the formulations after dilution may vary within wide ranges. The active compound concentration of the application forms may be situated typically between 0.00000001% and 95% by weight of active compound, between about 0.001% and 1% by weight, or preferably between about 0.01% and 0.30% by weight based on the weight of the application form. Application takes place in a customary manner adapted to the application forms.

In another aspect of the present invention, the formulation as described above is used for reducing overall damage of seeds, plants, plant parts and plant propagation material, as well as losses in harvested fruits or vegetables caused by bacteria, fungi, insects, mites, nematodes, viruses, and/or phytopathogens.

Furthermore, in another aspect of the present invention, the formulations as described above increases the overall plant health.

The term "plant health" generally comprises various sorts of improvements of plants that are not connected to the control of pests. For example, advantageous properties that may be mentioned are improved crop characteristics including: emergence, crop yields, protein content, oil content, starch content, more developed root system, improved root growth, improved root size maintenance, improved root effectiveness, improved stress tolerance (e.g. against drought, heat, salt, UV, water, cold), reduced ethylene (reduced production and/or inhibition of reception), tillering increase, increase in plant height, bigger leaf blade, less dead basal leaves, stronger tillers, greener leaf color, pigment content, photosynthetic activity, less input needed (such as fertilizers or water), less seeds needed, more productive tillers, earlier flowering, early grain maturity, less plant verse (lodging), increased shoot growth, enhanced plant vigor, increased plant stand, and early and better germination.

Improved plant health preferably refers to improved plant characteristics including: crop yield, more developed root system (improved root growth), improved root size maintenance, improved root effectiveness, tillering increase, increase in plant height, bigger leaf blade, less dead basal leaves, stronger tillers, greener leaf color, photosynthetic activity, more productive tillers, enhanced plant vigor, and increased plant stand.

The formulations according to the present invention, as it pertains to crop protection, may be applied in any desired manner, such as in the form of a seed coating, soil drench, and/or directly in-furrow and/or as a foliar spray and applied either pre-emergence, post-emergence or both. In other words, the formulations can be applied to the seed, the plant, plant parts, plant propagation material, or to harvested fruits and vegetables or to the soil wherein the plant is growing or wherein it is desired to grow (plant's locus of growth).

Preferably, the formulations according to the present invention are used for treating conventional or transgenic plants or seeds thereof.

If not mentioned otherwise, the treatment of plants or plant parts (which includes seeds and plants emerging from the seed), harvested fruits and vegetables, with the formulations according to the invention, are carried out directly or by action on their surroundings, habitat or storage space using customary treatment methods, for example dipping, spraying, atomizing, irrigating, evaporating, dusting, fogging, broadcasting, foaming, painting, spreading-on, watering (drenching), drip irrigating. It is furthermore possible to apply the formulation as sole-formulation or combined-formulations by the ultra-low volume method, or to inject the formulation according to the present invention as a formulation or as sole-formulations into the soil (in-furrow).

The term "plant to be treated" encompasses every part of a plant including its root system and the material—e.g., soil or nutrition medium—which is in a radius of at least 10 cm, 20 cm, 30 cm around the caulis or bole of a plant to be treated or which is at least 10 cm, 20 cm, 30 cm around the root system of said plant to be treated, respectively.

The application rate of the formulations to be employed or used according to the present invention may vary. The skilled person is able to find the appropriate application rate by way of routine experiments.

Seed Treatment

In another aspect of the present invention a seed treated with the formulations as described above is provided.

The control of insects, mites, nematodes, and/or phytopathogens by treating the seed of plants has been known for a long time and is a subject of continual improvements. Nevertheless, the treatment of seed entails a series of problems which cannot always be solved in a satisfactory manner. Thus, it is desirable to develop methods for protecting the seed and the germinating plant that remove the need for, or at least significantly reduce, the additional delivery of crop protection compositions in the course of storage, after sowing or after the emergence of the plants. It is desirable, furthermore, to optimize the amount of active ingredient employed in such a way as to provide the best-possible protection to the seed and the germinating plant from attack by insects, mites, nematodes and/or phytopathogens, but without causing damage to the plant itself by the active ingredient employed. In particular, methods for treating seed ought also to take into consideration the intrinsic insecticidal and/or nematicidal properties of pest-resistant or pest-tolerant transgenic plants, in order to achieve optimum protection of the seed and of the germinating plant with a minimal use of crop protection compositions.

The invention likewise relates to the use of the formulation of the invention for treating seed for the purpose of protecting the seed and the resultant plant against insects, mites, nematodes and/or phytopathogens.

Furthermore, the invention relates to seed which, following treatment with the formulation of the invention, is subjected to a film-coating process in order to prevent dust abrasion of the seed.

One of the advantages of the present invention is that, owing to the particular systemic properties of the formulations of the invention, the treatment of the seed with these formulations provides protection from insects, mites, nematodes and/or phytopathogens not only to the seed itself but also to the plants originating from the seed, after they have emerged. In this way, it may not be necessary to treat the crop directly at the time of sowing or shortly thereafter.

A further advantage is to be seen in the fact that, through the treatment of the seed with formulation of the invention, germination and emergence of the treated seed may be promoted.

It is likewise considered to be advantageous that the formulation of the invention may also be used, in particular, on transgenic seed.

The invention further relates to seed treatment formulations that comprise a benzoxaborole, and optionally one or more additional fungicides, nematicides, or mixtures thereof.

Exemplary additional fungicides include: carbendazim, thiabendazole, thiophanate, thiophanate-methyl, diethofencarb, zoxamide, ethaboxam, pencycuron, flupicolide, flutolanil, fluopyram, fluxapyroxad, penthiopyrad, benodanil, mepronil, isofetamid, fenfuram, carboxin, oxycarboxin, thifluzamide, benzovindiflupyr, bixafen, furametpyr, isopyrazam, penflufen, sedaxane, boscalid, benomyl, fuberidazole, diflumetorim, tolfenpyrad, azoxystrobin, coumoxystrobin, enoxastrobin, flufenoxystrobin, picoxystrobin, pyraoxystrobin, mandestrobin, pyraclostrobin, pyrametostrobin, triclopyricarb, kresoxim-methyl, trifloxystrobin, dimeoxystrobin, fenamistrobin, methominostrobin, orysastrobin, famoxadone, fluoxastrobin, fenamidone, pyribencarb, cyazofamid, amisulbrom, binapacryl, meptyldinocap, dinocap, fluazinam, fentin chloride, fentin acetate, fentin hydroxide, silthiofam, ametoctradin, cyprodinil, mepanipyrim, pyrimethanil, kasugamycin, quinoxyfen, proquinazid, fenpiclonil, fludioxonil, chlozolinate, dimethachlone, iprodione, procymidone, vinclozolin, triforine, pyrifenox, pyrisoxazole, fenarimol, nuarimol, imazalil, oxpoconazole, pefurazoate, prochloraz, triflumizole, azaconazole, bitertanol, bromuconazole, cyproconazole, diniconazole, epoxiconazole, etanconazole, fenbuconazole, fluquinconazole, flusilazole, flutriafol, hexaconazole, imibenconazole, ipconazole, metconazole, myclobutanil, penconazole, propiconazole, simeconazole, tebuconazole, tetraconazole, triadimefon, triadimenol, triticonazole, prothioconazole, aldimorph, dodemorph, fenpropimorph, tridemorph, fenpropidin, piperalin, spiroxamine, fenhexamid, fenpyrazamine, pyributicarb, naftifine, terbinafine, validamycin, polyoxin, dimethomorph, flumorph, pyrimorph, benthiavalicarb, iprovalicarb, valifenalate, mandipropamid, ferbam, macozeb, maneb, metiram, propineb, thiram, zineb, ziram, captan, captafol, folpet, dichlofluanid, tolylfluanid, and chlorothalonil.

Exemplary nematicides include: of avermectin nematicides, such as abamectin; carbamate nematicides, such as, aldicarb, thiadicarb, carbofuran, carbosulfan, oxamyl, aldoxycarb, ethoprop, methomyl, benomyl, alanycarb; and organophosphorus nematicides, such as, fenamiphos, fensulfothion, terbufos, fosthiazate, dimethoate, phosphocarb, dichlofenthion, isamidofos, fosthietan, isazofos ethoprophos, cadusafos, terbufos, chlorpyrifos, dichlofenthion, heterophos, isamidofos, mecarphon, phorate, thionazin, triazophos, diamidafos, fosthietan, and phosphamidon, as well as dichloropropene.

It is also stated that the formulation of the invention may be used in combination with agents of the phosphate technology, as a result of which, for example, colonization with symbionts is improved, such as rhizobia, mycorrhiza and/or endophytic bacteria, for example, is enhanced, and/or nitrogen fixation is optimized.

The formulations of the invention are suitable for protecting seed of any variety of plant which is used in agriculture, in greenhouses, in forestry or in horticulture. More particularly, the seed in question is that of cereals (e.g., wheat, barley, rye, oats and millet), maize, cotton, soybeans, rice, potatoes, sunflower, coffee, tobacco, canola, oilseed rape, beets (e.g., sugar beet and fodder beet), peanuts, vegetables (e.g., tomato, cucumber, bean, brassicas, onions and lettuce), fruit plants, lawns and ornamentals. Particularly important is the treatment of the seed of cereals (e.g., wheat, barley, rye and oats) maize, soybeans, cotton, canola, oilseed rape and rice.

As already mentioned above, the treatment of transgenic seed with the formulation of the invention is particularly important. The seed in question here is that of plants which generally contain at least one heterologous gene that controls the expression of a polypeptide having, in particular, insecticidal and/or nematicidal properties. These heterologous genes in transgenic seed may come from microorganisms such as *Bacillus, Rhizobium, Pseudomonas, Serratia, Trichoderma, Clavibacter, Glomus,* or *Gliocladium*. The present invention is particularly suitable for the treatment of transgenic seed which contains at least one heterologous gene from *Bacillus* sp. With particular preference, the heterologous gene in question comes from *Bacillus thuringiensis*.

For the purposes of the present invention, the formulations of the invention are applied alone or in a suitable formulation to the seed. The seed is preferably treated in a condition in which its stability is such that no damage occurs in the course of the treatment. Generally speaking, the seed may be treated at any point in time between harvesting and sowing. Typically, seed is used which has been separated from the plant and has had cobs, hulls, stems, husks, hair or pulp removed. Thus, for example, seed may be used that has been harvested, cleaned and dried to a moisture content of less than 15% by weight. Alternatively, seed can also be used that after drying has been treated with water, for example, and then dried again.

When treating seed it is necessary, generally speaking, to ensure that the amount of the formulation of the invention, and/or of other additives, that is applied to the seed is selected such that the germination of the seed is not adversely affected, and/or that the plant which emerges from the seed is not damaged. This is the case in particular with active ingredients which may exhibit phytotoxic effects at certain application rates.

The formulations of the invention can be applied directly, in other words without comprising further components, and without having been diluted. As a general rule, it is preferable to apply the formulations in the form of a suitable formulation to the seed.

The formulations which can be used in accordance with the invention may be converted into the customary seed-dressing formulations, such as solutions, emulsions, suspensions, powders, foams, slurries or other coating compositions for seed, and also ULV formulations.

These formulations are prepared by mixing the benzoxaborole and surfactant with customary adjuvants, such as, for example, customary extenders and also solvents or diluents, colorants, wetters, dispersants, emulsifiers, antifoams, antioxidants, preservatives, secondary thickeners, antifreezes, stickers, gibberellins, and also water.

Colorants which may be present in the seed-dressing formulations which can be used in accordance with the invention include all colorants which are customary for such purposes. In this context, it is possible to use not only pigments, which are of low solubility in water, but also water-soluble dyes. Examples include the colorants known under the designations Rhodamin B, C.I. Pigment Red 112 and C.I. Solvent Red 1.

Wetters, which may be present in the seed-dressing formulations and can be used in accordance with the invention, include all of the substances which promote wetting and which are customary in the formulation of active agrochemical ingredients. Use may be made preferably of alkylnaphthalenesulphonates, such as diisopropyl- or diisobutyl-naphthalenesulphonates.

Dispersants and/or emulsifiers which may be present in the seed-dressing formulations that can be used in accordance with the invention include all of the nonionic, anionic, and cationic dispersants that are customary in the formulation of active agrochemical ingredients. Use may be made preferably of nonionic or anionic dispersants or of mixtures of nonionic or anionic dispersants. Suitable nonionic dispersants are, in particular, ethylene oxide-propylene oxide block polymers, alkylphenol polyglycol ethers, polyalkylene oxide block co-polymers, acrylic co-polymers and also tristryrylphenol polyglycol ethers, and the phosphate or sulphated derivatives of these. Suitable anionic dispersants are, in particular, lignosulphonates, salts of polyacrylic acid, and arylsulphonate-formaldehyde condensates.

Antifoams which may be present in the seed-dressing formulations which can be used in accordance with the invention include all of the foam inhibitors that are customary in the formulation of active agrochemical ingredients. Use may be made preferably of silicone antifoams and magnesium stearate.

Antioxidants which may be present in the seed-dressing formulation are preferably those that have a low level of phytotoxicity. It is also preferred that the antioxidant that is used in the present method and formulations be one that is approved for use in food, feed, or cosmetics. Examples of such approval are approval by a regulatory body, such as the U.S. Food and Drug Administration for use in food or cosmetics, or approval by the U.S. Department of Agriculture for use. Antioxidants that have GRAS (Generally Recognized As Safe) status are examples of preferred antioxidants. In some embodiments of the present invention, it is preferred that the antioxidant is one that is added to the seed, as opposed to an antioxidant that is a natural component of the seed. However, such preferred antioxidants can include natural antioxidants that are added to the seed during the present treatment process.

Examples of materials that can serve as the antioxidant of the present invention include: glycine, glycinebetaine, choline salts, in particular choline chloride, 2(3)-tert-butyl-4-hydroxyanisole (BHA), tert-butylhydroxyquinone (TBHQ), dilauryl thiodipropionate (DLTDP), tris(nonylphenyl))phosphite (TNPP), 2,6-dihydroxybenzoic acid (DHBA), acetylsalicylic acid (ASA), salicylic acid (SA), Irganox 1076 (Ciba Geigy), Ethanox 330 (Ethyl Corp.), Tinuvin 144 (Ciba Geigy), Ambiol (2-methyl-4-[dimethylaminomethyl]-5-hydroxybenzimidazole), propyl gallate, trihydroxybutyrophenone (THBP), thiodipropionic acid and dilauryl thiodipropionate, betaines (see, AU-B-27071/95 to Bodapati, and EO 0 493 670 A1 to Lunkenheimer et al.), amines (aromatic amines and hindered amines), methionine, cysteine, proline, mannitol, phosphites, thioesters, lecithin, gum or resin guiac, Vitamin E, polyphenols, Vitamin A, carotenoids (beta-carotene), Vitamin B, Vitamin C, tocopherols, alpha-lipoic acid, coenzyme Q10 CoQ10), grape seed extract, green tea, lutein, N-acetyl Cysteine (NAC), OPCs (pycnogenols), selenium, zinc, 2,6-di-tert-para-benzoquinone, abscisic acid, bioflavonoids, DMAE (N,N-Dimethylethanolamine, precursor of choline), metronidazole, 2-methyl-5-nitroimidazole, glyoxal, polymerized 2,2,4-trimethyl-1,2-dihydroquinoline, 2-mercaptobenzimidazol, 5-tert-butyl-4-hydroxy-2-methyl-phenyl sulfide (CAS RN 96-69-5), 4-tert-butylphenol (CAS RN 98-54-4), catechol (CAS RN 120-80-9), 2-naphthol (2-hydroxynaphthalene) (CAS RN 135-19-3), octadecyl-3-(3',5'-di-tert-butyl-4-hydroxyphenyl) propionate (CAS RN 2082-79-3), 1,3,5-trimethyl-2,4,6-tris (3,5-di-tert-butyl-4-hydroxybenzyl)benzene (CAS RN 1709-70-2), and tris-(2,4,-di-tert-butylphenyl)phosphite (CAS RN 31570-04-4).

In some embodiments, hindered phenol antioxidants are preferred. Examples of hindered phenol antioxidants include: 2,6-di-tert-butyl-p-cresol (BHT) (CAS RN 128-37-0), 2(3)-tert-butyl-4-hydroxyanisole (BHA), isobutylenated methylstyrenated phenol (CAS RN 68457-74-9), styrenated phenol (CAS RN 61788-44-1), 2,6-di-tert-butyl-4-(octadecanoxycarbonylethyl)phenol (CAS RN 2082-79-3), 4,4'-thiobis-6-(t-butyl-m-cresol) (CAS RN 96-69-5), 4,4'-butylidenebis(6-t-butyl-m-cresol) (CAS RN 85-60-9), 4,4'-(1-methylethylidene)bis[2-(1,1-dimethylethyl)]phenol (CAS RN 79-96-9), 2,2'-methylenebis(4-methyl-6-nonyl)phenol (CAS RN 7786-17-6), 4-methyl-phenol reaction products with dicyclopentadiene and isobutylene (CAS RN 68610-51-5), tetrakis-(methylene-(3,5-di-tertbutyl-4-hydrocinnamate)methane (CAS RN 6683-19-8), tert-butylhydroxyquinone (TBHQ), Irganox 1076, Ethanox 330, and 1,3,5-tris(3,5-di-tert-butyl-4-hydroxybenzyl-)-1,3,5-triazine-2,4,6 (1H,3H,5H)-trione (CAS RN 27676-62-6).

Preservatives which may be present in the seed-dressing formulations which can be used in accordance with the invention include all of the substances which can be employed for such purposes in agrochemical compositions. Examples include dichlorophen and benzyl alcohol hemiformal.

Secondary thickeners which may be present in the seed-dressing formulations which can be used in accordance with the invention include all substances which can be used for such purposes in agrochemical compositions. Those contemplated with preference include cellulose derivatives, acrylic acid derivatives, xanthan, modified clays and highly disperse silica.

Stickers which may be present in the seed-dressing formulations which can be used in accordance with the invention include all customary binders which can be used in seed-dressing products. Preferred mention may be made of polyvinylpyrrolidone, polyvinyl acetate, polyvinyl alcohol, styrene acrylic emulsion polymers, polyethylene wax, and tylose.

Gibberellins which may be present in the seed-dressing formulations which can be used in accordance with the invention include preferably the gibberellins A1, A3 (=gibberellic acid), A4 and A7, with gibberellic acid being used with particular preference. The gibberellins are known (cf. R. Wegler, "Chemie der Pflanzenschutz-und Schädlingsbekämpfungsmittel", Volume 2, Springer Verlag, 1970, pp. 401-412).

The seed-dressing formulations which can be used in accordance with the invention may be used, either directly or after prior dilution with water, to treat seed of any of a wide variety of types. Accordingly, the concentrates or the preparations obtainable from them by dilution with water may be employed to dress the seed of cereals, such as wheat, barley, rye, oats and triticale, and also the seed of maize, rice, oilseed rape, peas, beans, cotton, sunflowers and beets, or else the seed of any of a very wide variety of vegetables. The seed-dressing formulations which can be used in accordance with the invention, or their diluted preparations, may also be used to dress seed of transgenic plants. In that case, additional synergistic effects may occur in interaction with the substances formed through expression.

For the treatment of seed with the seed-dressing formulations which can be used in accordance with the invention, or with the preparations produced from them by addition of water, suitable mixing equipment includes all such equipment which can typically be employed for seed dressing. More particularly, the procedure when carrying out seed dressing is to place the seed in a mixer, to add the particular desired amount of seed-dressing formulations, either as such or following dilution with water beforehand, and to carry out mixing until the distribution of the formulation on the seed is uniform. This may be followed by a drying operation.

The application rate of the seed-dressing formulations which can be used in accordance with the invention may be varied within a relatively wide range. It is guided by the particular amount of the at least one biological control agent and the at least one oxaborole in the formulations, and by the seed. The application rates in the case of the composition are situated generally at between 0.001 and 50 g per kilogram of seed, preferably between 0.01 and 15 g per kilogram of seed.

The invention also relates to a method for controlling unwanted microorganisms, characterized in that the inventive composition is applied to the phytopathogenic fungi, phytopathogenic bacteria, and/or their habitat.

The formulations, according to the invention, can be used to treat all plants, plant propagation material, and plant parts. Plants means all plants and plant populations, such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

The inventive formulations, when it is well tolerated by plants, have favorable toxicity and are well tolerated by the environment, are suitable for protecting plants and plant organs, enhances harvest yields and improves the quality of the harvested material. It can preferably be used as crop protection composition. It is active against normally sensitive and tolerant species and against all or some stages of development.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combinations.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

A number of embodiments of the present disclosure have been described. While this specification contains many specific implementation details, the specific implementation details should not be construed as limitations on the scope of any disclosures or of what may be claimed, but rather as descriptions of features specific to particular embodiments of the present disclosure.

Certain features that are described in this specification in the context of separate embodiments can also be implemented in combination in a single embodiment. Conversely, various features that are described in the context of a single embodiment can also be implemented in combination in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In certain implementations, multitasking and parallel processing may be advantageous. Nevertheless, it will be understood that various modifications may be made without departing from the spirit and scope of the claimed disclosure.

EXAMPLES

Throughout the examples, 5-chlorobenzo[c][1,2]oxaborol-1(3H)-ol may be referred to as "BAG8". The structure for 5-chlorobenzo[c][1,2]oxaborol-1(3H)-ol (BAG8) is:

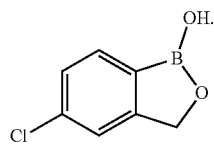 [SMILES: OB1OCc2cc(Cl)ccc21]

Section I: Exemplary Benzoxaborole Formulations

Example 1: Emulsion Concentrate Formulation and Applied Formulation Stability A sample emulsion concentrate was prepared by preparing a mixture containing 9.0 mg of octylphenol polyethylene glycol ether (Triton X-45, surfactant), 9.0 mg of sodium dodecylbenzenesulfonate, 12 mg of polyethylene glycol 40 castor oil hydrogenated, 90 mg of cyclohexanone, 150 mg of xylenes, and 30 mg of 5-chlorobenzo[c][1,2]oxaborol-1(3H)-ol to obtain the emulsion concentrate. The emulsion concentrate was then added to 20 g of water and gently shaken (to produce a sample applied formulation). The applied formulation was visually monitored for stability over the course of 20 minutes, and during this time the initial white emulsion quickly formed a white precipitate and clear solution. Given the instability of the diluted (applied) formulation, the mixture was not subjected to particle size analysis.

Example 2: Emulsion Concentrate Formulation and Applied Formulation Stability A sample emulsion concentrate was prepared by first preparing a mixture containing 9.0 mg of octylphenol polyethylene glycol ether (Triton X-45), 18.0 mg of sodium dodecylbenzenesulfonate, 12 mg of polyethylene glycol 40 castor oil hydrogenated, 90 mg of cyclohexanone, 150 mg of xylenes, and 30 mg of 5-chlorobenzo[c][1,2]oxaborol-1(3H)-ol. The emulsion concentrate was then added to 20 g of water and gently shaken (to produce a sample applied formulation). The applied formulation was visually monitored for stability over the course of 20 minutes, and during this time the initial white emulsion quickly formed a white precipitate and clear solution. When sieved, large chunks of material were trapped on each sieve, indicating a particle size greater than 297 m.

Example 3: Emulsion Concentrate Formulation and Applied Formulation Stability A sample emulsion concentrate was prepared by mixing 0.4 g of benzyl alcohol, 0.2 g of isophorone, 0.2 g of xylenes, 80 mg of Tween 20, and 30 mg of 5-chlorobenzo[c][1,2] oxaborol-1(3H)-ol. This emulsion concentrate was then added to 20 g of water and gently shaken (to produce a sample applied formulation suitable for biological testing). The applied formulation was visually monitored for stability over the course of 20 minutes, and then sieved successively through #50, #100, and #325 sieves to determine particle size. The applied formulation remained a milky white emulsion over the course of 20 minutes and passed through each sieve, indicating a stable formulation with a particle size of less than 44 m.

Example 4: Emulsion Concentrate Formulation and Applied Formulation Stability A sample emulsion concentrate was prepared by mixing 0.4 g of isophorone, 0.4 g of xylenes, 80 mg of Tween 20, and 30 mg of 5-chlorobenzo[c][1,2]oxaborol-1(3H)-ol. This emulsion concentrate was then added to 20 g of water and gently shaken (to produce a sample applied formulation suitable for biological testing). The applied formulation was visually monitored for stability over the course of 20 minutes, and then sieved successively through #50, #100, and #325 sieves to determine particle size. The applied formulation remained a milky white emulsion over the course of 20 minutes. When sieved, material was trapped on each sieve, indicating a particle size greater than 297 m. Compared to Example 3, this emulsion had much larger particle size, indicating that incorporation of the protic solvent (benzyl alcohol) resulted in a smaller particle size for the emulsion.

Example 5: Emulsion Concentrate Formulation and Applied Formulation Stability A sample emulsion concentrate was prepared by mixing 0.4 g of isophorone, 80 mg of Tween 20, and 30 mg of 5-chlorobenzo[c][1,2]oxaborol-1(3H)-ol. This emulsion concentrate was then added to 20 g of water and gently shaken (to produce a sample applied formulation suitable for biological testing). The applied formulation was visually monitored for stability over the course of 30 minutes, and then analyzed with a Malvern 3000E to determine particle size. The applied formulation remained a milky white emulsion over the course of 30 minutes. When analyzed, the emulsion showed a $D_{50}$ of 111 µm and a $D_{90}$ of 146 µm.

Example 6: Emulsion Concentrate Formulation and Applied Formulation Stability A sample emulsion concentrate was prepared by mixing 1.6 g of n-butanol, 0.8 g chlorobenzene, 0.32 g of Tween 20, 0.16 g of Span 20, 0.14 g of ATLOX 4838, and 0.12 g of 5-chlorobenzo[c][1,2]oxaborol-1(3H)-ol. This emulsion concentrate was then added to 80 g of water and gently shaken (to produce a sample applied formulation suitable for biological testing). The applied formulation was visually monitored for stability over the course of 30 minutes, and then analyzed with a Malvern 3000E to determine particle size. The applied formulation remained a milky white emulsion over the course of 30 minutes. When analyzed, the emulsion showed a $D_{50}$ of 1.31 µm and a $D_{90}$ of 4.36 µm.

Example 7: Emulsion Concentrate Formulation and Applied Formulation Stability A sample emulsion concentrate was prepared by mixing 0.8 g of benzyl alcohol, 0.4 g isophorone, 0.4 g of xylenes, 0.16 g of polyethylene glycol 40 castor oil hydrogenated, 0.12 g of Span 20, 68 mg of ATLOX 4838, and 60 mg of 5-chlorobenzo[c][1,2]oxaborol-1(3H)-ol. This emulsion concentrate was then added to 40 g of water and gently shaken (to produce a sample applied formulation suitable for biological testing). The applied formulation was visually monitored for stability over the course of 30 minutes, and then analyzed with a Malvern 3000E to determine particle size. The applied formulation remained a milky white emulsion over the course of 30 minutes. When analyzed, the emulsion showed a $D_{50}$ of 0.578 μm and a $D_{90}$ of 3.78 μm.

Example 8: Suspension Concentrate Formulation and Applied Formulation Stability A sample suspension concentrate was prepared by mixing 0.4 g of Atlas G-5002L, 0.4 g ATLOX 4913, 5 g of glycerin, 50 mg of anti-foam compound, 40 mg of xanthan gum, 20 mg of anti-microbial, 74.09 g of water, and 20 g of 5-chlorobenzo[c][1,2]oxaborol-1(3H)-ol. 150 mg of this suspension concentrate was then added to 20 g of water and gently shaken (to produce a sample applied formulation suitable for biological testing). The applied formulation was visually monitored for stability over the course of 30 minutes, and then analyzed with a Malvern 3000E to determine particle size. The applied formulation remained a white suspension over the course of 30 minutes. When analyzed, the solution showed a $D_{50}$ of 10.70 μm and a $D_{90}$ of 25.50 μm.

Example 9: Suspension Concentrate Formulation and Formulation Stability

A sample suspension concentrate was prepared by mixing 0.4 g of Atlas G-5002L, 0.4 g ATLOX 4913, 5 g of glycerin, 50 mg of anti-foam compound, 40 mg of xanthan gum, 20 mg of anti-microbial, 74.09 g of water, and 20 g of 5-chlorobenzo[c][1,2]oxaborol-1(3H)-ol. The formulation was visually monitored for stability over the course of 10 days at; 5° C., 20° C., and 50° C., and then analyzed with a Malvern 3000E to determine particle size. Visually, the 50° C. sample demonstrated hard sedimentation and settling of active ingredient but there was little to no change at the other temperature conditions. When analyzed, the applied formulation showed particle sizes illustrated by the table below.

| Temperature | Day 1 | | | Day 5 | | | Day 10 | | |
|---|---|---|---|---|---|---|---|---|---|
| | $D_{10}$ | $D_{50}$ | $D_{90}$ | $D_{10}$ | $D_{50}$ | $D_{90}$ | $D_{10}$ | $D_{50}$ | $D_{90}$ |
| 5° C. | 3.29 | 9.57 | 24.8 | 3.27 | 9.42 | 23.4 | 3.10 | 9.02 | 22.9 |
| 20° C. | 3.74 | 10.7 | 25.5 | 3.06 | 8.95 | 22.7 | 3.40 | 9.74 | 23.9 |
| 50° C. | 3.18 | 9.02 | 22.5 | 3.42 | 9.66 | 32.6 | 2.89 | 8.28 | 21.0 |

Example 10: Suspension Concentrate Formulation and Applied Formulation Stability A sample suspension concentrate was prepared by mixing 0.4 g of Atlas G-5002L, 0.4 g ATLOX 4913, 5 g of glycerin, 50 mg of anti-foam compound, 0.24 g of xanthan gum, 0.12 g of anti-microbial, 73.79 g of water, and 20 g of 5-chlorobenzo[c][1,2]oxaborol-1(3H)-ol. 150 mg of this suspension concentrate was then added to 20 g of water and gently shaken (to produce a sample applied formulation suitable for biological testing). The applied formulation was visually monitored for stability over the course of 30 minutes, and then analyzed with a Malvern 3000E to determine particle size. The applied formulation remained a white suspension over the course of 30 minutes. When analyzed, the suspension showed a $D_{50}$ of 6.10 μm and a $D_{90}$ of 15.50 μm.

Example 11: Suspension Concentrate Formulation and Formulation Stability

A sample suspension concentrate was prepared by mixing 0.4 g of Atlas G-5002L, 0.4 g ATLOX 4913, 5 g of glycerin, 50 mg of anti-foam compound, 40 mg of xanthan gum, 20 mg of anti-microbial, 73.79 g of water, and 20 g of 5-chlorobenzo[c][1,2]oxaborol-1(3H)-ol. The formulation was visually monitored for stability over the course of 10 days at; 5° C., 20° C., and 50° C., and then analyzed with a Malvern 3000E to determine particle size. Visually, the sample displayed little to no change over the 10 days at the three temperature conditions. When analyzed, the diluted formulation showed particle sizes illustrated by Table 1 below.

TABLE 1

| Temperature | Day 1 | | | Day 5 | | | Day 10 | | |
|---|---|---|---|---|---|---|---|---|---|
| | $D_{10}$ | $D_{50}$ | $D_{90}$ | $D_{10}$ | $D_{50}$ | $D_{90}$ | $D_{10}$ | $D_{50}$ | $D_{90}$ |
| 5° C. | 2.06 | 5.89 | 14.3 | 1.95 | 5.65 | 14.0 | 2.02 | 5.81 | 14.3 |
| 20° C. | 2.11 | 6.10 | 15.5 | 1.79 | 5.60 | 13.7 | 1.67 | 5.41 | 13.1 |
| 50° C. | 1.84 | 5.89 | 20.5 | 2.34 | 7.11 | 26.9 | 2.24 | 7.14 | 28.4 |

Example 12: Suspension Concentrate Formulation and Applied Formulation Stability A sample suspension concentrate was prepared by mixing 0.8 g of Atlas G-5002L, 0.8 g ATLOX 4913, 5 g of glycerin, 50 mg of anti-foam compound, 0.178 g of xanthan gum, 89 mg of anti-microbial, 53.08 g of water, and 40 g of 5-chlorobenzo[c][1,2]oxaborol-1(3H)-ol. 150 mg of this suspension concentrate was then added to 20 g of water and gently shaken (to produce a sample applied formulation suitable for biological testing). The applied formulation was visually monitored for stability over the course of 30 minutes, and then analyzed with a Malvern 3000E to determine particle size. The applied formulation remained a white suspension over the course of 30 minutes. When analyzed, the solution showed a $D_{50}$ of 4.57 μm and a $D_{90}$ of 16.1 μm.

Example 13: Suspension Concentrate Formulation and Formulation Stability

A sample suspension concentrate was prepared by mixing 0.8 g of Atlas G-5002L, 0.8 g ATLOX 4913, 5 g of glycerin, 50 mg of anti-foam compound, 0.178 g of xanthan gum, 89 mg of anti-microbial, 53.08 g of water, and 40 g of 5-chlorobenzo[c][1,2]oxaborol-1(3H)-ol. The formulation was visually monitored for stability over the course of 10 days at; 5° C., 20° C., and 50° C., and then analyzed with a Malvern 3000E to determine particle size. Visually, the sample displayed little to no change over the 10 days at the three temperature conditions. When analyzed, the applied formulation showed particle sizes illustrated by Table 2 below.

TABLE 2

| Temperature | Day 1 | | | Day 5 | | | Day 10 | | |
|---|---|---|---|---|---|---|---|---|---|
| | $D_{10}$ | $D_{50}$ | $D_{90}$ | $D_{10}$ | $D_{50}$ | $D_{90}$ | $D_{10}$ | $D_{50}$ | $D_{90}$ |
| 5° C. | 2.03 | 5.45 | 20.5 | 1.64 | 4.67 | 16.7 | 1.66 | 4.64 | 16.3 |
| 20° C. | 1.62 | 4.57 | 16.1 | 1.85 | 5.06 | 18.0 | 1.63 | 4.61 | 17.0 |
| 50° C. | 1.90 | 5.57 | 15.1 | 2.20 | 6.44 | 21.9 | 2.23 | 6.81 | 24.8 |

Example 14: Suspension Concentrate for Seed Treatment Formulation and Applied Germination A sample suspension concentrate for seed treatment was prepared by mixing 0.8 g of Atlas G-5002L, 0.8 g ATLOX 4913, 5 g of glycerin, 50 mg of anti-foam compound, 0.178 g of xanthan gum, 89 mg of anti-microbial, 53.08 g of water, and 40 g of 5-chlorobenzo[c][1,2]oxaborol-1(3H)-ol. 23 mg of this suspension concentrate was then added to 0.26 g of water, 78 mg of Florite 1706, 36 mg of colorant, and gently shaken (to produce a sample applied formulation suitable for treating seeds). The formulation was added to 100 g of soybean seeds in a tumbler seed treater. The treated seeds were planted in small pots of soil to test germination. Germination results were recorded after 7 days; as illustrated below, the treated seeds germinated at a rate of 90%, comparable to the control which had a germination rate of 98%.

TABLE 3

| | Amount of Benzoxaborole Suspension Concentrate 23 mg |
|---|---|
| Soil germination | 18/20 |
| Germination % | 90% |

Example 15: Suspension Concentrate for Seed Treatment Formulation and Applied Germination A sample suspension concentrate for seed treatment was prepared by mixing 0.8 g of Atlas G-5002L, 0.8 g ATLOX 4913, 5 g of glycerin, 50 mg of anti-foam compound, 0.178 g of xanthan gum, 89 mg of anti-microbial, 53.08 g of water, and 40 g of 5-chlorobenzo[c][1,2]oxaborol-1(3H)-ol. 46 mg of this suspension concentrate was then added to 0.26 g of water, 78 mg of Florite 1706, 36 mg of colorant, and gently shaken (to produce a sample applied formulation suitable for treating seeds). The formulation was added to 100 g of soybean seeds in a tumbler seed treater. The treated seeds were planted in small pots of soil to test germination. Germination results were recorded after 7 days; as illustrated below, the treated seeds germinated at a rate of 95%, similar to the control, which had a germination rate of 98%.

TABLE 4

| | Amount of Benzoxaborole Suspension Concentrate 46 mg |
|---|---|
| Soil germination | 19/20 |
| Germination % | 95% |

Example 16: Suspension Concentrate for Seed Treatment Formulation and Applied Germination A sample suspension concentrate for seed treatment was prepared by mixing 0.8 g of Atlas G-5002L, 0.8 g ATLOX 4913, 5 g of glycerin, 50 mg of anti-foam compound, 0.178 g of xanthan gum, 89 mg of anti-microbial, 53.08 g of water, and 40 g of 5-chlorobenzo[c][1,2]oxaborol-1(3H)-ol. 70 mg of this suspension concentrate was then added to 0.26 g of water, 78 mg of Florite 1706, 36 mg of colorant, and gently shaken (to produce a sample applied formulation suitable for treating seeds). The formulation was added to 100 g of soybean seeds in a tumbler seed treater. The treated seeds were planted in small pots of soil to test germination. Germination results were recorded after 7 days; as illustrated below, the treated seeds germinated at a rate of 95%, which is similar to the germination rate of the control (98%).

TABLE 5

| | Amount of Benzoxaborole Suspension Concentrate 70 mg |
|---|---|
| Soil germination | 19/20 |
| Germination % | 95% |

Example 17: Suspension Concentrate for Seed Treatment Formulation and Applied Germination A sample suspension concentrate for seed treatment was prepared by mixing 0.8 g of Atlas G-5002L, 0.8 g ATLOX 4913, 5 g of glycerin, 50 mg of anti-foam compound, 0.178 g of xanthan gum, 89 mg of anti-microbial, 53.08 g of water, and 40 g of 5-chlorobenzo[c][1,2]oxaborol-1(3H)-ol. 0.14 g of this suspension concentrate was then added to 0.26 g of water, 78 mg of Florite 1706, 36 mg of colorant, and gently shaken (to produce a sample applied formulation suitable for treating seeds). The formulation was added to 100 g of soybean seeds in a tumbler seed treater. The treated seeds were planted in small pots of soil to test germination. Germination results were recorded after 7 days; as illustrated below, the treated seeds germinated at a rate of 95% which was similar to the germination rate of the control (98%).

TABLE 6

| | Amount of Benzoxaborole Suspension Concentrate 0.14 g |
|---|---|
| Soil germination | 19/20 |
| Germination % | 95% |

Example 18: Wettable Power Formulation and Applied Formulation Stability

A sample wettable powder was prepared by jet milling 5-chlorobenzo[c][1,2]oxaborol-1(3H)-ol (30%), Kaolin (60%), Morwet D-425 (8%), and Morwet EFW (2%). 0.50 g of the wettable powder formulation was added to 50 mL of water in a graduated cylinder and the resulting suspension was visually monitored over the course of 5 days. While the applied formulation slowly settled over the course of 24 hours, the particulate the bottom of the graduated cylinder easily resuspended upon mixing. When analyzed, the applied formulation showed a $D_{50}$ of 2.93 μm and a $D_{90}$ of 6.97 μm.

Example 19: Emulsion Concentrate Formulation and Applied Formulation Stability

A sample emulsion concentrate was prepared by mixing 0.8 g of benzyl alcohol, 0.4 g isophorone, 0.4 g of xylenes, 0.16 g of polyethylene glycol 40 castor oil hydrogenated, 28 mg of ATLOX 4838, and 42 mg of 5-chlorobenzo[c][1,2]oxaborol-1(3H)-ol. This emulsion concentrate was then added to 40 g of water and gently shaken (to produce a sample applied formulation suitable for biological testing). The applied formulation was visually monitored for stability over the course of 30 minutes, and then analyzed with a Malvern 3000E to determine particle size. The applied formulation remained a milky white emulsion over the course of 30 minutes. When analyzed, the emulsion showed a $D_{50}$ of 6.70 μm and a $D_{90}$ of 15.4 μm.

Example 20: BAG8 Emulsion Concentrate (EC) Formulations

In addition to the examples above, further BAG8 emulsion concentrates were prepared. The formulations were prepared by mixing the components shown in Table 7. All components in the table are provided as % w/w (percent by weight—the percentage weight of each substance of the total EC weight).

The testing results for the emulsion concentrates disclosed in Table 7 are given in Table 8. Emulsion stability was tested for each EC by aliquoting 0.628 g of emulsion concentrate into 40 mL of water, the mixture was shaken rapidly to form an emulsion, and the emulsion was allowed to sit at room temperature undisturbed for 30 minutes. Visual appearance notes were taken and then particle size was measured using a Malvern Mastersizer 3000E.

To achieve a stable emulsion with a favorable $D_{90}$ particle size, a suitable combination of protic and aprotic solvents is needed. The results in Table 8 show that when using only protic solvents or aprotic solvents (i.e., using only one type of solvent rather than both types) a stable emulsion did not form, and large amounts of sedimentation were observed after a short period of time.

Moreover, the testing results indicate that surfactant selection is also important, and should be carefully considered after selecting a solvent blend. A blend of high HLB, low HLB, and anionic surfactants usually yielded the most stable emulsions with the lowest $D_{90}$ particle sizes. Additionally, when the protic alcohol was removed from the top performing emulsion concentrates, the emulsions made thereafter were unstable and showed rapid sedimentation. Accordingly, it seemed that the presence of the protic component contributed to the overall stability and performance of the emulsion.

It can also be seen from the tables that the EC formulations had ratios of 15:1 through 1:4 (ratio of protic:aprotic solvents) (i.e. 15 through 0.25). Formulations with a ratio of 1:3 had on average the lower $D_{90}$ particle size. As shown in other examples, disease control was best achieved with EC formulations when the ratio was a 1:1 or 1:3 (i.e 1 or 0.33).

TABLE 7

EC Formulations of BAG8

| Ex. | Solvent 1 (aprotic solvent) | % w/w | Solvent 2 | % w/w | Solvent 3 (protic Solvent) | % w/w | Non-ionic Surfactant 1 | % w/w | Non-ionic Surfactant 2 | % w/w | Anionic Surfactant | % w/w | BAG8 % w/w |
|---|---|---|---|---|---|---|---|---|---|---|---|---|---|
| 1-1 | Isophorone | 21.6 | Xylenes | 21.6 | Benzyl Alcohol | 43.2 | PEG-40 Hydrogenated Castor Oil | 8.69 | — | — | Atlox 4838B | 1.51 | 3.67 |
| 1-2 | Isophorone | 21.9 | Xylenes | 21.9 | Benzyl Alcohol | 43.7 | PEG-40 Hydrogenated Castor Oil | 8.80 | — | — | Atlox 4838B | 1.53 | 2.21 |
| 2-1 | Cyelohexanone | 55.6 | Xylenes | 27.8 | — | — | Tween 21 | 8.33 | — | — | — | — | 8.33 |
| 3-1 | Isophorone | 62.1 | — | — | Benzyl Alcohol | 15.5 | PEG-40 Hydrogenated Castor Oil | 12.4 | — | — | Atlox 4838B | 5.28 | 4.66 |
| 4-1 | Isophorone | 57.3 | — | — | Decyl Alcohol | 19.1 | Tween 22 | 7.96 | Atlox 4916 | 1.59 | Atlox 4838B | 4.46 | 9.55 |
| 4-2 | Isophorone | 70.9 | — | — | — | — | Tween 22 | 9.84 | Atlox 4916 | 1.97 | Atlox 4838B | 5.51 | 11.8 |
| 5-1 | Isophorone | 57.3 | — | — | Decyl Alcohol | 19.1 | Tween 22 | 7.96 | Span 20 | 1.59 | Atlox 4838B | 4.46 | 9.55 |
| 5-2 | Isophorone | 70.9 | — | — | — | — | Tween 22 | 9.84 | Span 20 | 1.97 | Atlox 4838B | 5.51 | 11.8 |
| 6-1 | Isophorone | 19.1 | — | — | Decyl Alcohol | 57.3 | Tween 20 | 7.96 | Atlox 4916 | 1.59 | Atlox 4838B | 4.46 | 9.55 |
| 6-2 | Isophorone | 76.4 | — | — | — | — | Tween 20 | 7.96 | Atlox 4916 | 1.59 | Atlox 4838B | 4.46 | 9.55 |
| 7-1 | Isophorone | 38.2 | Xylenes | 19.1 | Decyl Alcohol | 19.1 | Tween 60 | 9.55 | — | — | Atlox 4838B | 4.46 | 9.55 |
| 7-2 | Isophorone | 47.2 | Xylenes | 23.6 | — | — | Tween 60 | 11.8 | — | — | Atlox 4838B | 5.51 | 11.8 |
| 8-1 | Isophorone | 9.55 | — | — | Decyl Alcohol | 66.9 | Tween 20 | 9.55 | — | — | Atlox 4838B | 4.46 | 9.55 |
| 8-2 | Isophorone | 76.4 | — | — | — | — | Tween 20 | 9.55 | — | — | Atlox 4838B | 4.46 | 9.55 |
| 9-1 | Isophorone | 38.2 | Limonene | 19.1 | Decyl Alcohol | 19.1 | Tween 22 | 9.55 | — | — | Atlox 4838B | 4.46 | 9.55 |
| 9-2 | Isophorone | 38.2 | Limonene | 19.1 | Decyl Alcohol | 19.1 | Tween 22 | 4.77 | Span 20 | 4.77 | Atlox 4838B | 4.46 | 9.55 |
| 10-1 | Isophorone | 4.77 | — | — | Decyl Alcohol | 71.7 | Tween 60 | 9.55 | — | — | Atlox 4838B | 4.46 | 9.55 |

TABLE 7-continued EC Formulations of BAG8

| Ex. | Solvent 1 (aprotic solvent) | % w/w | Solvent 2 | % w/w | Solvent 3 (protic Solvent) | % w/w | Non-ionic Surfactant 1 | % w/w | Non-ionic Surfactant 2 | % w/w | Anionic Surfactant | % w/w | BAG8 % w/w |
|---|---|---|---|---|---|---|---|---|---|---|---|---|---|
| 10-2 | Isophorone | 4.77 | — | — | Decyl Alcohol | 71.7 | Tween 20 | 6.37 | Span 20 | 3.18 | Atlox 4838B | 4.46 | 9.55 |
| 11-1 | Isophorone | 19.1 | Limonene | 19.1 | Decyl Alcohol | 38.2 | Tween 85 | 9.55 | — | — | Atlox 4838B | 4.46 | 9.55 |
| 11-2 | Isophorone | 19.1 | Limonene | 19.1 | Decyl Alcohol | 38.2 | Tween 60 | 7.96 | Span 20 | 1.59 | Atlox 4838B | 4.46 | 9.55 |
| 11-3 | Isophorone | 19.1 | Limonene | 19.1 | Decyl Alcohol | 38.2 | Tween 85 | 4.77 | Atlox 4916 | 4.77 | Atlox 4838B | 4.46 | 9.55 |
| 11-4 | Isophorone | 19.1 | Limonene | 19.1 | Decyl Alcohol | 38.2 | Tween 85 | 4.77 | Span 20 | 4.77 | Atlox 4838B | 4.46 | 9.55 |
| 12-1 | Isophorone | 19.1 | Xylenes | 19.1 | Decyl Alcohol | 38.2 | Tween 60 | 9.55 | — | — | Atlox 4838B | 4.46 | 9.55 |
| 12-2 | Isophorone | 19.1 | Xylenes | 19.1 | Decyl Alcohol | 38.2 | Tween 20 | 7.96 | Span 20 | 1.59 | Atlox 4838B | 4.46 | 9.55 |
| 12-3 | Isophorone | 19.1 | Xylenes | 19.1 | Decyl Alcohol | 38.2 | Tween 20 | 7.96 | Atlox 4916 | 1.59 | Atlox 4838B | 4.46 | 9.55 |
| 12-4 | Isophorone | 19.1 | Xylenes | 19.1 | Decyl Alcohol | 38.2 | Tween 20 | 4.77 | Span 20 | 4.77 | Atlox 4838B | 4.46 | 9.55 |
| 13-1 | Isophorone | 38.2 | — | — | Isobutyl Alcohol | 38.2 | Tween 20 | 9.55 | — | — | Atlox 4838B | 4.46 | 9.55 |
| 14-1 | NMP | 51.0 | — | — | Decyl Alcohol | 25.5 | Tween 20 | 9.55 | — | — | Atlox 4838B | 4.49 | 9.55 |
| 15-1 | NMP | 40 | — | — | Decyl Alcohol | 40 | Tween 22 | 10 | — | — | — | — | 10 |
| 16-1 | Isophorone | 20 | — | — | Decyl Alcohol | 60 | Tween 22 | 10 | — | — | — | — | 10 |
| 17-1 | Isophorone | 40 | — | — | Decyl Alcohol | 40 | Tween 20 | 10 | — | — | — | — | 10 |
| 18-1 | — | — | — | — | Decyl Alcohol | 80 | Tween 20 | 10 | — | — | — | — | 10 |
| 19-1 | Isophorone | 80 | — | — | — | — | PEG-40 Hydrogenated Castor Oil | 10 | — | — | — | — | 10 |
| 20-1 | NMP | 80 | — | — | — | — | Tween 20 | 10 | — | — | — | — | 10 |
| 21-1 | Cyclohexanone | 80 | — | — | — | — | PEG-40 Hydrogenated Castor Oil | 10 | — | — | — | — | 10 |
| 22-1 | — | — | — | — | Isobutyl Alcohol | 80 | Tween 20 | 10 | — | — | — | — | 10 |

(Note:
NMP stands for N-methyl-2-pyrrolidone)

TABLE 8

Emulsion Stability of BAG8 Emulsion Concentrates Disclosed in Table 7

| Ex. | Appearance t = 0 min | Appearance t = 30 min | Particle Size $D_{90}$ (μm) at 30 mins |
|---|---|---|---|
| 1-1 | Milky White Emulsion | Milky White Emulsion | 17.0 |
| 1-2 | Milky White Emulsion | Milky White Emulsion | 15.4 |
| 2-1 | Pale White Emulsion | Pale White Emulsions With Crystallization | 48.3 |
| 3-1 | Milky White Emulsion | Milky White Emulsion | 29.2 |
| 4-1 | Milky White Emulsion | Milky White Emulsion | 8.44 |
| 4-2 | Pale White Emulsion | Milky White Emulsion With Large Crystals | Did not test due to instability at 30 mins |
| 5-1 | Milky White Emulsion | Milky White Emulsion | 9.70 |
| 5-2 | Pale White Emulsion | Milky White Emulsion With Large Crystals | Did not test due to instability at 30 mins |
| 6-1 | Milky White Emulsion | Milky White Emulsion | 12.0 |
| 6-2 | Pale White Emulsion | Milky White Emulsion With Large Crystals | Did not test due to instability at 30 mins |
| 7-1 | Milky White Emulsion | Milky White Emulsion | 10.1 |
| 7-2 | Pale White Emulsion | Milky White Emulsion With Large Crystals | Did not test due to instability at 30 mins |
| 8-1 | Milky White Emulsion | Milky White Emulsion | 10.8 |
| 8-2 | Milky White Emulsion | Milky White Emulsion With Large Crystals | Did not test due to instability at 30 mins |
| 9-1 | Milky White Emulsion | Milky White Emulsion | 14.4 |
| 9-2 | Milky White Emulsion | Milky White Emulsion | 26.5 |

TABLE 8-continued

Emulsion Stability of BAG8 Emulsion Concentrates Disclosed in Table 7

| Ex. | Appearance t = 0 min | t = 30 min | Particle Size $D_{90}$ (μm) at 30 mins |
|---|---|---|---|
| 10-1 | Milky White Emulsion | Milky White Emulsion | 15.0 |
| 10-2 | Milky White Emulsion | Milky White Emulsion | 28.9 |
| 11-1 | Milky White Emulsion | Milky White Emulsion | 15.6 |
| 11-2 | Milky White Emulsion | Milky White Emulsion | 10.7 |
| 11-3 | Milky White Emulsion | Milky White Emulsion With Crystals | Did not test due to instability at 30 mins |
| 11-4 | Milky White Emulsion | Milky White Emulsion | 30.8 |
| 12-1 | Milky White Emulsion | Milky White Emulsion | 15.0 |
| 12-2 | Milky White Emulsion | Milky White Emulsion | 13.7 |
| 12-3 | Milky White Emulsion | Milky White Emulsion | 22.5 |
| 12-4 | Milky White Emulsion | Milky White Emulsion | 17.4 |
| 13-1 | Pale White Emulsion | Pale White Emulsion With Large Crystals | Did not test due to instability at 30 mins |
| 14-1 | Milky White Emulsion | Milky White Emulsion | 35.2 |
| 15-1 | Milky White Emulsion | Milky White Emulsion | 31.4 |
| 16-1 | Milky White Emulsion | Milky White Emulsion | 39.4 |
| 17-1 | Milky White Emulsion | Milky White Emulsion | 29.6 |
| 18-1 | Biphasic | Biphasic With Crystals | Did not test due to instability at 30 mins |
| 19-1 | Bright Milky White Emulsions | Bright Milky White Emulsion with Large Crystals | Did not test due to instability at 30 mins |
| 20-1 | Pale White Emulsion | Biphasic With Large Crystals | Did not test due to instability at 30 mins |
| 21-1 | Pale White Emulsion | Pale White Emulsion With Large Crystals | Did not test due to instability at 30 mins |
| 22-1 | Pale White Emulsion | Pale White Emulsion With Large Crystals | Did not test due to instability at 30 mins |

Example 21: SC and EC Formulation Stability

BAG8 formulation samples were stored at 5° C., 20° C., or 50° C., and the stability of the samples was determined by visual appearance at time points of 0 days and 10 days. The particle size was also determined for each sample following dilution into water at each time point using a particle size analyzer (Malvern 3000E). $D_{90}$ particle size values were recorded for each sample and each time point. The pH of each sample was also recorded for each temperature at day zero and day 10.

It is desirable for the pH of the diluted/applied formulation to remain the same or to change minimally when the formulation is stored at various temperatures. It is also desirable for the $D_{90}$ of the diluted/applied formulation to remain the same or to change minimally when the formulation is stored at various temperatures As can be seen below, the pH remained the same or similar for many exemplary formulations at day 0 and at day 14 (compared to the 20° C. sample at day zero). Generally, the pH of the applied/diluted formulation may influence whether the benzoxaborole (BAG8) is in its neutral, planar form, or its ionic, tetrahedral form.

TABLE 9

| EC | Temp | pH Day 0 | pH Day 14 | Particle Size $D_{90}$ (μm) Day 0 | Particle Size $D_{90}$ (μm) Day 14 |
|---|---|---|---|---|---|
| 1-1 | 0° C. | — | 6.61 | — | 14.9 |
|  | 20° C. | 6.27 | 6.60 | 17.0 | 13.5 |
|  | 50° C. | — | 6.54 | — | 9.70 |
| 4-1 | 0° C. | — | 6.41 | — | 10.7 |
|  | 20° C. | 6.25 | 6.32 | 8.44 | 11.9 |
|  | 50° C. | — | 6.22 | — | 12.2 |
| 11-2 | 0° C. | — | 6.25 | — | 13.3 |
|  | 20° C. | 6.26 | 6.33 | 10.7 | 9.81 |
|  | 50° C. | — | 6.22 | — | 6.91 |
| 8-1 | 0° C. | — | 6.30 | — | 10.8 |
|  | 20° C. | 6.24 | 6.31 | 10.8 | 24.4 |
|  | 50° C. | — | 6.29 | — | 16.7 |

TABLE 10

| SC | Temp | pH Day 0 | pH Day 10 | Particle Size $D_{90}$ (μm) Day 0 | Particle Size $D_{90}$ (μm) Day 10 |
|---|---|---|---|---|---|
| Example 8 | 5° C. | — | 4.64 | — | 22.9 |
|  | 20° C. | 4.62 | 4.64 | 25.5 | 23.9 |
|  | 50° C. | — | 4.45 | — | 21.0 |
| Example 10 | 5° C. | — | 6.15 | — | 14.3 |
|  | 20° C. | 6.17 | 6.09 | 15.5 | 13.1 |
|  | 50° C. | — | 6.12 | — | 28.4 |
| Example 12 | 5° C. | — | 6.00 | — | 16.3 |
|  | 20° C. | 6.02 | 5.98 | 16.1 | 17.0 |
|  | 50° C. | — | 5.97 | — | 24.8 |

Example 22: BAG8-Alcohol Adduct Studies

A stock solution of 5-chlorobenzo[c][1,2]oxaborol-1(3H)-ol was prepared in DMSO-$d_6$ and the resulting solution was aliquoted into 5 NMR tubes (Samples 1-5 in Table 11 below). For purposes of the formulation example section, 5-chlorobenzo[c][1,2]oxaborol-1(3H)-ol will be referred to as BAG8. The amount of n-butanol indicated in Table 11 was then added to samples 1-5. An additional sample of n-butanol in DMSO-$d_6$ was also prepared for reference purposes (Sample No. 6).

$^1$H-NMR spectra were then recorded for each sample. Peaks corresponding to a BAG8 and n-butanol adduct were noted between δ 7.5-7.7 ppm and at δ 5.07 ppm with increasing intensity as the relative concentration of n-butanol increased, indicating the presence of a BAG8 and n-butanol adduct and BAG8 mixture (see Scheme 4 below). The ratio of the BAG8 and n-butanol adduct to BAG8 was determined by integration for each sample. The results are shown below in Table 11. An overlay of the $^1$H-NMR spectra are shown in FIG. 1. The numbers displayed on the spectra in FIG. 1 correspond to the Sample No. in Table 11.

TABLE 11

| Sample No. | Molar equivalents of BAG8 | Molar equivalents of n-butanol | BAG8 + n-Butanol Adduct:BAG8 Ratio |
|---|---|---|---|
| 1 | 1 | 0 | n/a |
| 2 | 1 | 0.5 | 1:25 |
| 3 | 1 | 1 | 1:14 |

TABLE 11-continued

| Sample No. | Molar equivalents of BAG8 | Molar equivalents of n-butanol | BAG8 + n-Butanol Adduct:BAG8 Ratio |
|---|---|---|---|
| 4 | 1 | 2.5 | 1:8 |
| 5 | 1 | 5 | 1:5 |
| 6 | n/a | n/a | n/a |

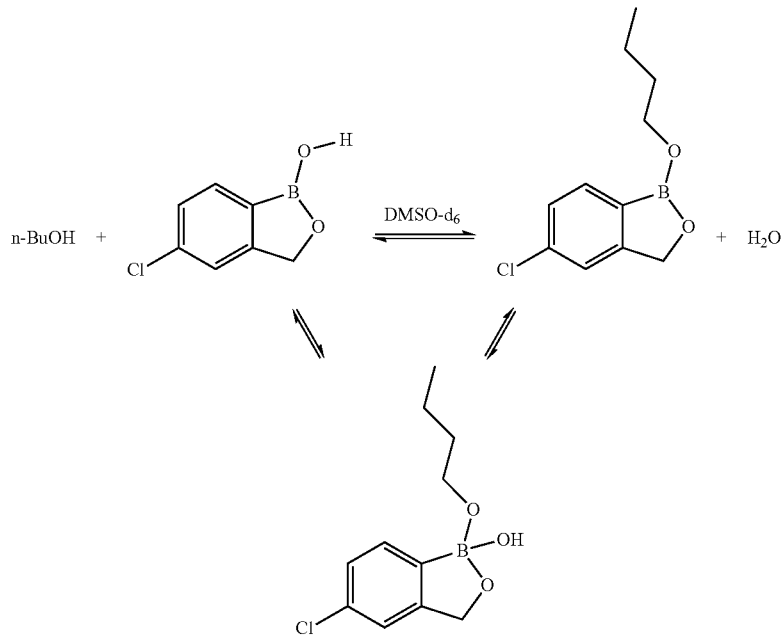

Scheme 4.

Example 23: BAG8 Suspension Concentrate (SC)-Adjuvant Compatibility Studies

The 20% BAG8 SC and 40% BAG8 SC described in Example 10 and Example 12, respectively, were tested for compatibility with various tank-mix adjuvants.

The amount of SC used for all tests was calculated such that there was 30 mg of BAG8 in each test. The adjuvants were tank-mixed with BAG8 SC at the label rate, using the mixing instructions indicated on the label. Each test used 20 mL of water.

The visual appearance of each of the tank-mixes was noted at zero minutes, 30 minutes, and 24 hours. Particle size analysis was done 30 minutes and 24 hours after initial mixing for tank-mixes that were visually stable for 30 minutes (Malvern 3000E).

For the Silwet Stik 2 tests, the BAG8 SC was added to water, then the Silwet Stik 2 was added to the resulting BAG8 mixture. Using the opposite order of addition (Silwet Stik 2 to water, followed by BAG8 SC) resulted in the formation of a white sediment that was not suitable for further analysis or use.

The results of the tests are shown in Table 12. The mixtures deemed compatible did not form sediments or oil slicks, and had similar particle size values at 30 minutes and 24 hours. The results show that the BAG8 SC formulations tested are compatible with a wide array of tank mix adjuvants.

TABLE 12

| Test | SC (wt % BAG8, g) | Adjuvant (amount) | Visual Appearance @ 0 min | Visual Appearance @ 30 min | Particle Size at 30 min (μm) | | | Visual Stability at 24 h | Particle size at 24 h (μm) | | |
|---|---|---|---|---|---|---|---|---|---|---|---|
| | | | | | $D_{10}$ | $D_{50}$ | $D_{90}$ | | $D_{10}$ | $D_{50}$ | $D_{90}$ |
| | 20%, 0.15 g | No adjuvant | Milky white | Milky white | 1.66 | 5.08 | 17.7 | Milky white | 1.27 | 4.69 | 17.7 |
| 1 | 20%, 0.15 g | Kinetic (18 mg) | Milky white | Milky white | 2.33 | 7.34 | 21.5 | Milky white | 3.14 | 15.2 | 59.9 |
| 2 | 20%, 0.15 g | Nu-Film (31 mg) | Milky white sedimentation | Milky white crashed out | — | — | — | Milky white, sedimentation | — | — | — |
| 3 | 20%, 0.15 g | Activator 90 (1 mL) | Milky white | Milky white | 3.63 | 7.19 | 15.5 | Milky white, no settling | 5.22 | 10.4 | 20.1 |
| 4 | 20%, 0.15 g | Activator 90 (0.2 mL) | Milky white | Milky white | 1.54 | 7.36 | 20.4 | Milky white | — | — | — |
| 5 | 20%, 0.15 g | Dyn-amic (75 uL) | Milky white | Milky white | .987 | 4.51 | 15.2 | Milky white | 1.08 | 4.98 | 26.8 |

TABLE 12-continued

| Test | SC (wt %) BAG8, g) | Adjuvant (amount) | Appearance @ 0 min | Visual Appearance @ 30 min | Particle Size at 30 min (μm) | | | Visual Stability at 24 h | Particle size at 24 h (μm) | | |
|---|---|---|---|---|---|---|---|---|---|---|---|
| | | | | | $D_{10}$ | $D_{50}$ | $D_{90}$ | | $D_{10}$ | $D_{50}$ | $D_{90}$ |
| 6 | 20%, 0.15 g | Air Cover (18 mg) | Milky white | Milky white | 1.97 | 5.76 | 14.1 | Milky white | 2.09 | 6.40 | 17.3 |
| 7 | 20%, 0.15 g | Silwet Stik 2 (40 mg) | Milky white | Milky white | 1.79 | 5.83 | 15.1 | Milky white | 2.34 | 7.22 | 21.2 |
| | 40%, 0.075 g | No Adjuvant | Milky white | Milky white | 1.05 | 3.09 | 12.2 | Milky White | 2.03 | 4.46 | 15.7 |
| 8 | 40%, 0.075 g | Kinetic (18 mg) | Milky white | Milky white | 1.93 | 8.29 | 26.4 | Milky white | 1.93 | 9.29 | 75.8 |
| 9 | 40%, 0.075 g | Nu-Film (31 mg) | Milky white, sedimentation | Milky white, sedimentation | — | — | — | Milky white, sedimentation | — | — | — |
| 10 | 40%, 0.075 g | Activator 90 (1 mL) | Milky white | Milky white, oily slick | — | — | — | Milky white oily slick. | — | — | — |
| 11 | 40%, 0.075 g | Activator 90 (0.2 mL) | Milky white | Milky white, oily slick | — | — | — | Milky white, oily slick | — | — | — |
| 12 | 40%, 0.075 g | Dyn-amic (75 uL) | Milky white | Milky white | .969 | 6.14 | 23.9 | Milky white | 1.21 | 4.42 | 61.2 |
| 13 | 40%, 0.075 g | Air Cover (18 mg) | Milky white | Milky white | 1.07 | 3.39 | 11.8 | Milky white | 1.22 | 3.89 | 10.7 |
| 14 | 40%, 0.075 g | Silwet Stik 2 (40 mg) | Milky white | Milky white | 1.15 | 3.81 | 12.4 | Milky white | 1.43 | 5.04 | 15.0 |

Example 24: BAG8 SC Biological Efficacy Studies

The BAG8 SC formulations described in Example 10 (BAG8 20% SC) and Example 12 (BAG8 40% SC) and selected BAG8 SC-tank mix formulations described in Example 23 were tested under greenhouse conditions. Data was obtained for soybean/white mold (*Sclerotinia sclerotiorum*), wheat/SNB (*Parastangaspora nodorum*), and cucubit/downy mildew. For each experiment, the BAG8 was applied at a rate of 0.25 lb/acre and at a spray rate of 20 gal/acre.

For this Example, the BAG8 EC used was: 3.4% BAG8, 43.2% benzyl alcohol, 21.6% isophorone, 21.6% xylenes, 8.6% PEG 40, 1.5% ATLOX 4838B (percentages are by weight).

The results show that all tested SC formulations of BAG8 had significantly lower disease severity compared to the untreated control. Specifically, the BAG8 20% SC tank mixed with Silwet Stik 2 and BAG8 40% SC tank-mixed with Aircover provided significantly better disease control compared to the untreated and most other formulations for all three pathosystems.

TABLE 13

Biological Efficacy of BAG8 SC Formulations on Wheat SNB

| Treatment | Mean Disease Severity (0-10 Scale)* | |
|---|---|---|
| Untreated Control | 6.800 | a |
| BAG8 20% SC | 5.636 | bc |
| BAG8 40% SC | 5.000 | cd |
| BAG8 EC | 3.727 | ef |
| BAG8 20% SC + Aircover | 4.455 | de |
| BAG8 20% SC + Silwet Stik 2 | 3.909 | ef |
| BAG8 40% SC + Aircover | 3.091 | f |
| BAG8 40% SC + Silwet Stik 2 | 6.091 | ab |

*Means followed by the same letter are not significantly different from each other ($\alpha = 0.05$).

TABLE 14

Biological Efficacy of BAG8 SC Formulations on Soybean White Mold

| Treatment | Mean Disease Severity (0-10)* | |
|---|---|---|
| Untreated Control | 6.182 | a |
| BAG8 20% SC | 1.800 | cde |
| BAG8 40% SC | 2.933 | bcd |
| BAG8 EC | 1.529 | cde |
| BAG8 20% SC + Activator 90 | 4.350 | b |
| BAG8 20% SC + Aircover | 1.333 | de |
| BAG8 20% SC + Silwet Stik 2 | 2.684 | cd |
| BAG8 40% SC + Aircover | 0.938 | e |
| BAG8 40% SC + Silwet Stik 2 | 3.125 | bc |

*Means followed by the same letter are not significantly different from each other ($\alpha = 0.05$).

TABLE 15

Biological Efficacy of BAG8 SC Formulations on Cucurbit/Downy Mildew.

| Treatment | Mean Disease Severity (0-10 Scale)* | |
|---|---|---|
| Untreated Control | 5.300 | a |
| BAG8 20% SC | 2.556 | cd |
| BAG8 40% SC | 2.000 | cd |
| 2$^{nd}$ Gen EC | 1.625 | d |
| BAG8 20% SC + Aircover | 2.778 | bcd |
| BAG8 20% SC + Silwet Stik 2 | 1.778 | d |
| BAG8 40% SC + Aircover | 3.333 | bc |
| BAG8 40% SC + Silwet Stik 2 | 3.909 | b |

*Means followed by the same letter are not significantly different from each other ($\alpha = 0.05$).

Example 25: SC, WP, and EC Biological Efficacy Studies

Various BAG8 EC formulations, the BAG8 WP formulation described in Example 18, and selected BAG8 SC-tank mix formulations described in Example 23 were tested under greenhouse conditions. Data was obtained for soybean/white mold (*Sclerotinia sclerotiorum*), wheat/SNB (*Parastangaspora nodorum*), and cucurbit/downy mildew. For each experiment, the BAG8 was applied at a rate of 0.25 lb/acre at a spray rate of 20 gal/acre (40 mL of spray solution prepared). All inoculum was applied 24 hours post BAG8 spray.

Unformulated BAG8 was applied to the plants by dissolving BAG8 in a 30% acetone-70% water solution.

The percentages shown for BAG8 EC are in weight percent.

The results for this study are found in Examples 26-29.

The treatments used, crop, disease and results are shown below in Tables 16-20 (for Examples 26-29). Means followed by the same letter are not significantly different from each other ($\alpha$=0.05).

The results show that, in many instances, the plants treated with unformulated BAG8 did not have lower disease severity than an untreated control. Thus, the results indicate that formulated BAG8 is more effective than unformulated BAG8. In fact, the level of efficacy for unformulated BAG8 falls below the industry standard for commercial formulation development.

Contrastingly, the results show that plants treated with a BAG8 SC, BAG8 EC, or BAG8 WP are more healthy than untreated plants in all cases and in most instances the plants are also more healthy than those treated with unformulated BAG8.

Example 26

The BAG8 EC formulations used for this example are shown below Table 16. The protocol described in Example 25 was used for this assay.

TABLE 16

Biological Efficacy of BAG8 Formulations on Wheat SNB

| Treatment | Mean Disease Severity | |
|---|---|---|
| Untreated Control | 6.750 | a |
| Unformulated BAG8 | 5.750 | a |
| BAG8 20% SC + Silwet Stik 2 | 3.250 | bc |
| BAG8 WP | 6.000 | a |
| BAG8 EC 1 | 6.250 | bc |
| BAG8 EC 2 | 2.000 | c |
| BAG8 EC 3 | 3.750 | b |
| BAG8 EC 4 | 3.500 | b |

BAG8 EC 1: 3.4% BAG8, 43.2% benzyl alcohol, 21.6% isophorone, 21.6% xylenes, 8.6% PEG 40, 1.5% ATLOX 4838B
BAG8 EC 2: 19.1% decyl alcohol, 57.3% isophorone, 4.5% ATLOX 4838B, 8.0% Tween 22, 1.6% ATLOX 4916, 9.6% BAG8
BAG8 EC 3: 19.1% decyl alcohol, 57.3% isophorone, 4.5% ATLOX 4838B, 8.0% Tween 22, 1.6% Span 20, 9.6% BAG8
BAG8 EC 4: 57.3% decyl alcohol, 19.1% isophorone, 4.5% ATLOX 4838B, 8.0% Tween 20, 1.6% ATLOX 4916, 9.6% BAG8

Example 27

The BAG8 EC formulations used for this example are shown below Table 17. The protocol described in Example 25 was used for this assay.

TABLE 17

Biological Efficacy of BAG8 Formulations on Curcurbit/Downy Mildew.

| Treatment | Mean Disease Severity | |
|---|---|---|
| Untreated Control | 8.364 | a |
| Unformulated BAG8 | 2.000 | e |
| BAG8 20% SC + Silwet Stik 2 | 3.900 | b |
| BAG8 WP | 0.750 | f |
| BAG8 EC 1 | 2.250 | de |
| BAG8 EC 2 | 3.167 | bc |
| BAG8 EC 3 | 3.583 | bc |
| BAG8 EC 4 | 3.500 | bc |
| BAG8 EC 5 | 3.000 | cd |
| BAG8 EC 6 | 3.750 | bc |
| BAG8 EC 7 | 1.833 | e |
| BAG8 EC 8 | 3.667 | bc |

BAG8 EC 1: 3.4% BAG8, 43.2% benzyl alcohol, 21.6% isophorone, 21.6% xylenes, 8.6% PEG 40, 1.5% ATLOX 4838B
BAG8 EC 2: 38.2% isophorone, 19.1% decyl alcohol, 19.1% xylenes, 4.5% ATLOX 4838B, 9.6% BAG8, 9.6% Tween 60
BAG8 EC 3: 9.5% isophorone, 66.7% decyl alcohol, 4.4% ATLOX 4838B, 9.8% BAG8, 9.5% Tween 20.
BAG8 EC 4: 57.3% decyl alcohol, 19.1% isophorone, 4.5% ATLOX 4838B, 8.0% Tween 20, 1.6% ATLOX 4916, 9.6% BAG8
BAG8 EC 5: 38.2% isophorone, 19.1% decyl alcohol, 19.1% limonene, 4.5% ATLOX 4838B, 9.6% Tween 22, 9.6% BAG8
BAG8 EC 6: 4.8% isophorone, 71.7% decyl alcohol, 4.5% ATLOX 4838B, 9.6% Tween 60, 9.6% BAG8
BAG8 EC 7: 19.1% isophorone, 38.2% decyl alcohol, 19.1% limonene, 4.5% ATLOX 4838B, 9.6% Tween 85, 9.6% BAG8
BAG8 EC 8: 19.1% isophorone, 38.2% decyl alcohol, 19.1% xylenes, 4.5% ATLOX 4838B, 9.6% Tween 60, 9.6% BAG8

Example 28

The BAG8 EC formulations used for this example are shown below Table 18. The protocol described in Example 25 was used for this assay.

TABLE 18

Biological Efficacy of BAG8 Formulations on Curcurbit/Downy Mildew.

| Treatment | Mean Disease Severity | |
|---|---|---|
| Untreated Control | 6.667 | a |
| Unformulated BAG8 | 5.833 | b |
| BAG8 20% SC + Silwet Stik 2 | 4.583 | c |
| BAG8 WP | 3.417 | d |
| BAG8 EC 1 | 2.917 | d |
| BAG8 EC 2 | 1.250 | ef |
| BAG8 EC 3 | 0.636 | f |
| BAG8 EC 4 | 1.667 | e |

BAG8 EC 1: 3.4% BAG8, 43.2% benzyl alcohol, 21.6% isophorone, 21.6% xylenes, 8.6% PEG 40, 1.5% ATLOX 4838B
BAG8 EC 2: 19.1% decyl alcohol, 57.3% isophorone, 4.5% ATLOX 4838B, 8.0% Tween 22, 1.6% ATLOX 4916, 9.6% BAG8
BAG8 EC 3: 19.1% decyl alcohol, 57.3% isophorone, 4.5% ATLOX 4838B, 8.0% Tween 22, 1.6% Span 20, 9.6% BAG8
BAG8 EC 4: 57.3% decyl alcohol, 19.1% isophorone, 4.5% ATLOX 4838B, 8.0% Tween 20, 1.6% ATLOX 4916, 9.6% BAG8

Example 29

The BAG8 EC formulations used for this example are shown below Table 19. The protocol described in Example 25 was used for this assay.

TABLE 19

Biological Efficacy of BAG8 Formulations on Soybean/White Mold.

| Treatment | Mean Disease Severity | |
|---|---|---|
| Untreated Control | 7.333 | a |
| Unformulated BAG8 | 5.333 | abc |
| BAG8 20% SC + Silwet Stik 2 | 6.500 | abc |
| BAG8 WP | 7.000 | ab |
| BAG8 EC 1 | 3.167 | d |
| BAG8 EC 2 | 5.000 | bcd |
| BAG8 EC 3 | 4.667 | cd |
| BAG8 EC 4 | 5.333 | abc |

TABLE 20

Biological Efficacy of BAG8 Formulations on Cucumber/Downy Mildew.

| Treatment | Mean Disease Severity | |
|---|---|---|
| Untreated Control | 7.417 | a |
| Unformulated BAG8 | 5.833 | b |
| BAG8 20% SC + Silwet Stik 2 | 2.917 | c |
| BAG8 WP | 2.833 | c |
| BAG8 EC 1 | 0.917 | d |
| BAG8 EC 2 | 0.750 | d |
| BAG8 EC 3 | 2.000 | c |
| BAG8 EC 4 | 0.667 | d |

BAG8 EC 1: 3.4% BAG8, 43.2% benzyl alcohol, 21.6% isophorone, 21.6% xylenes, 8.6% PEG 40, 1.5% ATLOX 4838B
BAG8 EC 2: 38.2% isophorone, 19.1% decyl alcohol, 19.1% xylenes, 4.5% ATLOX 4838B, 9.6% Tween 60, 9.6% BAG8
BAG8 EC 3: 9.6% isophorone, 66.9% decyl alcohol, 4.5% ATLOX 4838B, 9.6% Tween 20, 9.6% BAG8
BAG8 EC 4: 57.3% decyl alcohol, 19.1% isophorone, 4.5% ATLOX 4838B, 8.0% Tween 20, 1.6% ATLOX 4916, 9.6% BAG8

Section II: Experimental Procedures for Syntheses of Exemplary Benzoxaborole Compounds FIG. 2 contains a table that provides chemical characterization data for a number of exemplary benzoxaborole compounds, including some of those for which synthesis is described in the examples below. FIG. 2 contains chemical structure, formula, IUPAC chemical name, MS, and HPLC purity data for each compound.

Example 1: 5,7-dichloro-1-hydroxy-N,N-dimethyl-3H-2,1-benzoxaborol-6-amine

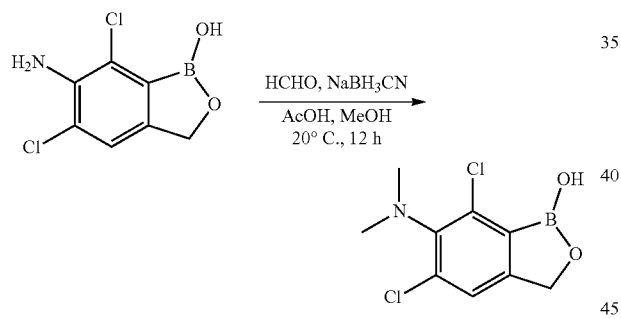

To a mixture of 5,7-dichloro-1-hydroxy-3H-2,1-benzoxaborol-6-amine (0.2 g, 918.08 umol, 1 eq) in MeOH (5 mL) was added acetic acid (82.70 mg, 1.38 mmol, 78.76 uL, 1.5 eq) and formaldehyde solution (74.51 mg, 918.08 umol, 37% W/W, 1 eq) at 20° C. The mixture was stirred at 20° C. for 1 h, then $NaBH_3CN$ (86.54 mg, 1.38 mmol, 1.5 eq) was added to the mixture at 0° C., and the resulting mixture was stirred at 20° C. for 11 h. The reaction mixture was quenched by addition of saturated aqueous $NH_4Cl$ solution (10 mL), and extracted with EtOAc (10 mL×3). The combined organic layers were washed with brine (10 mL×3), dried over $Na_2SO_4$, filtered and concentrated under reduced pressure. The resulting residue was purified by prep-HPLC (column: Nano-micro Kromasil C18 100*30 mm 5 um; mobile phase: [water (0.1% TFA)-ACN]; B %: 35%-65%, 10 min) to give 5,7-dichloro-1-hydroxy-N,N-dimethyl-3H-2,1-benzoxaborol-6-amine (40 mg, 162.67 umol, 17.72% yield) as a white solid. $^1$H NMR (DMSO-$d_6$, 400 MHz) δ 9.24 (s, 1H), 7.48 (s, 1H), 4.92 (s, 2H), 2.82 (s, 6H). MS (ESI): mass calcd. For $C_9H_{11}BCl_3NO_2$ 280.00, m/z found 246.0 [M+H]$^+$. Purity by HPLC: 86.26% (220 nm), 94.3% (254 nm).

Example 2: 5,7-dichloro-N,N-diethyl-1-hydroxy-3H-2,1-benzoxaborol-6-amine

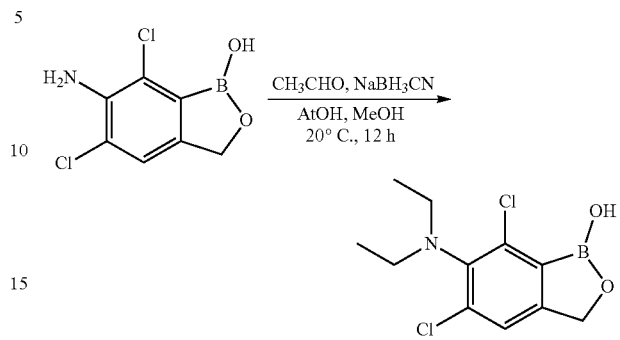

To a mixture of 5,7-dichloro-1-hydroxy-3H-2,1-benzoxaborol-6-amine (250 mg, 1.15 mmol, 1 eq) in MeOH (5 mL) was added dropwise acetaldehyde (126.39 mg, 1.15 mmol, 161.00 uL, 40% purity, 1 eq) and $CH_3COOH$ (103.37 mg, 1.72 mmol, 98.45 uL, 1.5 eq) at 20° C. The mixture was stirred at 20° C. for 1 h, and then $NaBH_3CN$ (108.18 mg, 1.72 mmol, 1.5 eq) was added. The resulting mixture was stirred at 20° C. for 11 h, then quenched by addition of saturated aqueous $NH_4Cl$ solution (10 mL), and extracted with EtOAc (10 mL×3). The combined organic layers were washed with brine (10 mL×3), dried over $Na_2SO_4$, filtered and concentrated under reduced pressure. The residue was purified by prep-HPLC (column: Nano-micro Kromasil C18 100*30 mm 5 um; mobile phase: [water (0.1% TFA)-ACN]; B %: 45%-70%, 10 min) to give 5,7-dichloro-N,N-diethyl-1-hydroxy-3H-2,1-benzoxaborol-6-amine (40 mg, 146.01 umol, 12.72% yield) as a yellow solid. $^1$H NMR (DMSO-$d_6$, 400 MHz) δ 7.50 (s, 1H), 4.94 (s, 2H), 3.19-3.13 (m, 4H), 0.93 (t, J=7.2 Hz, 6H). MS (ESI): mass calcd. For $C_{11}H_{14}BCl_2NO_2$ 273.05, m/z found 274.0 [M+H]$^+$. Purity by HPLC: 100.00% (220 nm), 100.00% (254 nm).

Example 3: 5,7-dichloro-1-hydroxy-N-methyl-3H-2,1-benzoxaborol-6-amine

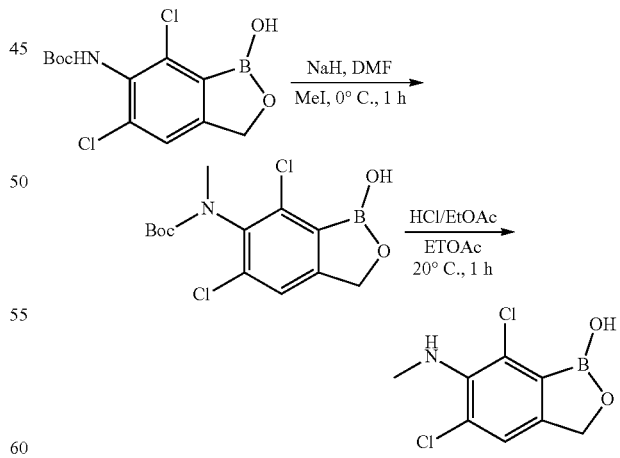

tert-butyl N-(5,7-dichloro-1-hydroxy-3H-2,1-benzoxaborol-6-yl)-N-methyl-carbamate To a mixture of tert-butyl N-(5,7-dichloro-1-hydroxy-3H-2,1-benzoxaborol-6-yl)carbamate (0.2 g, 629.01 umol, 1 eq)

in DMF (2 mL) was added NaH (75.47 mg, 1.89 mmol, 60% purity, 3 eq) in portions at 0° C. The mixture was stirred at 0° C. for 0.5 h, and then MeI (89.28 mg, 629.01 umol, 39.16 uL, 1 eq) was added to the mixture at 0° C., and the resulting mixture was stirred at 0° C. for 0.5 h. The reaction mixture was quenched by addition saturated aqueous NH$_4$Cl solution (10 mL), and extracted with EtOAc (10 mL×3). The combined organic layers were washed with brine (10 mL×3), dried over anhydrous Na$_2$SO$_4$, filtered and concentrated under reduced pressure. The resulting residue was purified by prep-HPLC (column: Nano-micro Kromasil C18 100*30 mm 5 um; mobile phase: [water (0.1% TFA)-ACN]; B %: 35%-65%, 10 min) to give tert-butyl N-(5,7-dichloro-1-hydroxy-3H-2,1-benzoxaborol-6-yl)-N-methyl-carbamate (130 mg, 391.58 umol, 62.25% yield) as a white solid. $^1$H NMR (DMSO-d$_6$, 400 MHz) δ 9.36 (m, 1H), 7.64 (s, 1H), 5.05-4.94 (m, 2H), 3.04-3.00 (m, 3H), 1.47-1.26 (m, 9H). MS (ESI): mass calcd. For C$_{13}$H$_{16}$BCl$_2$NO$_4$ 331.05, m/z found 276.0 [M-56+H]$^+$. Purity by HPLC: 99.18% (220 nm), 100.00% (254 nm).

To a mixture of tert-butyl N-(5,7-dichloro-1-hydroxy-3H-2,1-benzoxaborol-6-yl)-N-methyl-carbamate (0.1 g, 301.22 umol, 1 eq) in EtOAc (5 mL) was added a solution of HCl/EtOAc (4 M, 753.04 uL, 10 eq) at 20° C. The mixture was stirred at 20° C. for 1 h, then concentrated under reduced pressure to give 5,7-dichloro-1-hydroxy-N-methyl-3H-2,1-benzoxaborol-6-amine (71 mg, 264.60 umol, 87.84% yield, HCl) as a yellow solid. $^1$H NMR (DMSO-d$_6$, 400 MHz) δ 7.41 (s, 1H), 4.88 (s, 2H), 2.88 (s, 3H). MS (ESI): mass calcd. For C$_8$H$_9$BCl$_3$NO$_2$ 266.98, m/z found 231.9 [M+H]$^+$. Purity by HPLC: 100.00% (220 nm), 100.00% (254 nm).

Example 4: 5,7-dichloro-N-ethyl-1-hydroxy-3H-2,1-benzoxaborol-6-amine

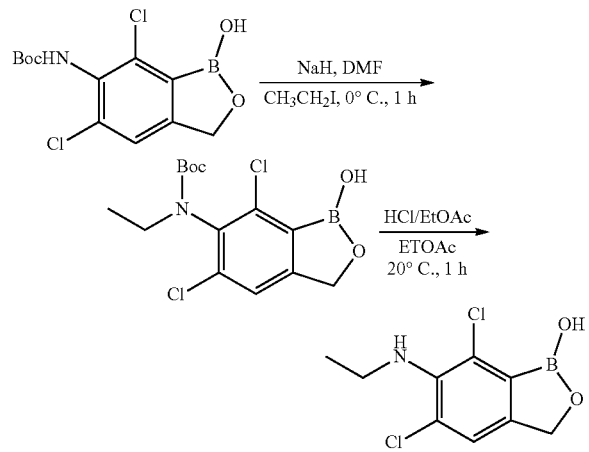

tert-butyl N-(5,7-dichloro-1-hydroxy-3H-2,1-benzoxaborol-6-yl)-N-ethyl-carbamate To a mixture of tert-butyl N-(5,7-dichloro-1-hydroxy-3H-2,1-benzoxaborol-6-yl)carbamate (0.2 g, 629.01 umol, 1 eq) in DMF (3 mL) was added NaH (75.47 mg, 1.89 mmol, 60% purity, 3 eq) in portions at 0° C. The mixture was stirred at 0° C. for 0.5 h, then CH$_3$CH$_2$I (117.72 mg, 754.81 umol, 60.37 uL, 1.2 eq) was added. The mixture was stirred at 0° C. for 0.5 h, then quenched by addition of saturated aqueous NH$_4$Cl solution (10 mL), and extracted with EtOAc (10 mL×3). The combined organic layers were washed with brine (10 mL×3), dried over Na$_2$SO$_4$, filtered and concentrated under reduced pressure. The resulting residue was purified by prep-HPLC (column: Xtimate C18 150*25 mm*5 um; mobile phase: [water (0.04% NH$_3$H$_2$O+10 mM NH$_4$HCO$_3$)-ACN]; B %: 22%-52%, 10.5 min) to give tert-butyl N-(5,7-dichloro-1-hydroxy-3H-2,1-benzoxaborol-6-yl)-N-ethyl-carbamate (100 mg, 289.01 umol, 45.95% yield) as a white solid. $^1$H NMR (DMSO-d$_6$, 400 MHz) δ 9.30 (s, 1H), 7.63 (s, 1H), 5.04-4.94 (m, 2H), 3.58-3.46 (m, 2H), 1.46-1.26 (m, 9H), 1.11-1.01 (m, 3H). MS (ESI): mass calcd. For C$_{14}$H$_{18}$BCl$_2$NO$_4$ 345.07, m/z found 290.0 [M-56+H]$^+$. Purity by HPLC: 99.83% (220 nm), 100.00% (254 nm).

To a mixture of tert-butyl N-(5,7-dichloro-1-hydroxy-3H-2,1-benzoxaborol-6-yl)-N-ethyl-carbamate (100 mg, 289.01 umol, 1 eq) in EtOAc (5 mL) was added a solution of HCl/EtOAc (4 M, 1.45 mL, 20 eq) at 20° C. The mixture was stirred at 20° C. for 1 h, and then concentrated under reduced pressure to give 5,7-dichloro-N-ethyl-1-hydroxy-3H-2,1-benzoxaborol-6-amine (65 mg, crude, HCl) as a yellow solid. $^1$H NMR (DMSO-d$_6$, 400 MHz) δ 7.43 (s, 1H), 4.89 (s, 2H), 3.25 (q, J=7.2 Hz, 2H), 1.07 (t, J=7.2 Hz, 3H). MS (ESI): mass calcd. For C$_9$H$_{11}$BCl$_3$NO$_2$ 280.99, m/z found 246.0 [M+H]$^+$. Purity by HPLC: 98.92% (220 nm), 99.32% (254 nm).

Example 5: 5,7-dichloro-1-hydroxy-N-propyl-3H-2,1-benzoxaborol-6-amine

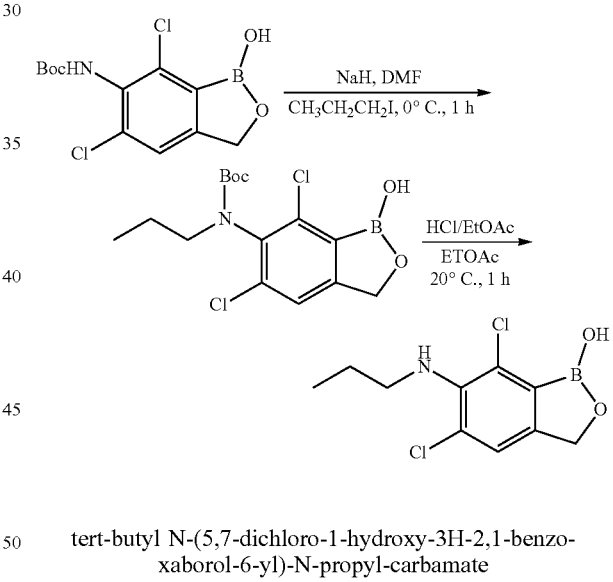

tert-butyl N-(5,7-dichloro-1-hydroxy-3H-2,1-benzoxaborol-6-yl)-N-propyl-carbamate To a mixture of tert-butyl N-(5,7-dichloro-1-hydroxy-3H-2,1-benzoxaborol-6-yl)carbamate (200 mg, 629.01 umol, 1 eq) in DMF (4 mL) was added NaH (75.48 mg, 1.89 mmol, 60% purity, 3 eq) in portions at 0° C. The mixture was stirred at 0° C. for 0.5 h, and then 1-iodopropane (160.39 mg, 943.51 umol, 92.18 uL, 1.5 eq) was added at 0° C. The resulting mixture was stirred at 0° C. for 0.5 h, then quenched by addition of saturated aqueous NH$_4$Cl solution (10 mL), and extracted with EtOAc (10 mL×3). The combined organic layers were washed with brine (10 mL×3), dried over Na$_2$SO$_4$, filtered and concentrated under reduced pressure. The residue was purified by prep-HPLC (column: Nano-micro Kromasil C18 100*30 mm 5 um; mobile phase: [water (0.1% TFA)-ACN]; B %: 50%-75%, 10 min). Compound tert-butyl N-(5,7-dichloro-1-hydroxy-3H-2,1-benzoxaborol-6-yl)-N-propyl-carbamate (110 mg, 305.52 umol, 48.57% yield) was obtained as a white solid. $^1$H NMR (DMSO-$d_6$, 400 MHz) δ 9.33 (s, 1H), 7.63 (s, 1H), 5.05-4.95 (m, 2H), 3.45-3.36 (m, 2H), 1.53-1.26 (m, 11H), 0.87-0.81 (m, 3H). MS (ESI): mass calcd. For $C_{15}H_{20}BCl_2NO_4$ 359.09, m/z found 304.0 [M-56+H]$^+$. Purity by HPLC: 97.9% (220 nm), 100.00% (254 nm).

To a mixture of tert-butyl N-(5,7-dichloro-1-hydroxy-3H-2,1-benzoxaborol-6-yl)-N-propyl-carbamate (80 mg, 222.20 umol, 1 eq) in EtOAc (5 mL) was added HCl/EtOAc (4 M, 1.11 mL, 20 eq) at 20° C. The mixture was stirred at 20° C. for 1 h. The reaction mixture concentrated under reduced pressure to give 5,7-dichloro-1-hydroxy-N-propyl-3H-2,1-benzoxaborol-6-amine (51 mg, 172.07 umol, 77.44% yield, HCl) as a yellow solid. $^1$H NMR (DMSO-$d_6$, 400 MHz) δ 7.42 (s, 1H), 4.89 (s, 2H), 3.24-3.18 (m, 2H), 1.53-1.44 (m, 2H), 0.87 (t, J=7.2 Hz, 3H). MS (ESI): mass calcd. For $C_{10}H_{13}BCl_3NO_2$ 295.01, m/z found 260.0 [M+H]$^+$. Purity by HPLC: 97.45% (220 nm), 95.61% (254 nm).

Example 6: N-butyl-5,7-dichloro-1-hydroxy-3H-2,1-benzoxaborol-6-amine

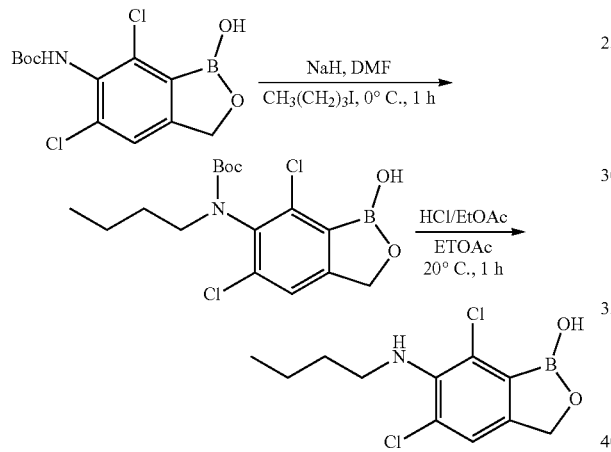

tert-butyl N-butyl-N-(5,7-dichloro-1-hydroxy-3H-2,1-benzoxaborol-6-yl)carbamate

To a mixture of tert-butyl N-(5,7-dichloro-1-hydroxy-3H-2,1-benzoxaborol-6-yl)carbamate (200 mg, 629.01 umol, 1 eq) in DMF (4 mL) was added NaH (75.48 mg, 1.89 mmol, 60% purity, 3 eq) in portions at 0° C. The mixture was stirred at 0° C. for 0.5 h, then 1-iodobutane (173.63 mg, 943.51 umol, 107.18 uL, 1.5 eq) was added at 0° C. The mixture was stirred at 0° C. for 0.5 h, then quenched by addition of saturated aqueous NH$_4$Cl solution (10 mL), extracted with EtOAc (10 mL×3). The combined organic layers were washed with brine (10 mL×3), dried over Na$_2$SO$_4$, filtered and concentrated under reduced pressure. The residue was purified by prep-HPLC (column: Nano-micro Kromasil C18 100*30 mm 5 um; mobile phase: [water (0.1% TFA)-ACN]; B %: 55%-80%, 10 min) to give tert-butyl N-butyl-N-(5,7-dichloro-1-hydroxy-3H-2,1-benzoxaborol-6-yl)carbamate (120 mg, 320.80 umol, 51.00% yield) as a yellow solid. $^1$H NMR (DMSO-$d_6$, 400 MHz) δ 9.32 (s, 1H), 7.62 (s, 1H), 5.04-4.94 (m, 2H), 3.48-3.41 (m, 2H), 1.49-1.22 (m, 13H), 0.87-0.81 (m, 3H). MS (ESI): mass calcd. For $C_{16}H_{22}BCl_2NO_4$ 373.10, m/z found 318.0 [M-56+H]$^+$. Purity by HPLC: 98.83% (220 nm), 100.00% (254 nm).

To a mixture of tert-butyl N-butyl-N-(5,7-dichloro-1-hydroxy-3H-2,1-benzoxaborol-6-yl)carbamate (90 mg, 240.60 umol, 1 eq) in EtOAc (5 mL) was added HCl/EtOAc (4 M, 1.20 mL, 20 eq) at 20° C. The mixture was stirred at 20° C. for 1 h. The reaction mixture concentrated under reduced pressure to give N-butyl-5,7-dichloro-1-hydroxy-3H-2,1-benzoxaborol-6-amine (57 mg, crude, HCl) as a yellow solid. $^1$H NMR (DMSO-$d_6$, 400 MHz) δ 7.42 (s, 1H), 4.88 (s, 2H), 3.23 (t, J=7.2 Hz, 2H), 1.49-1.41 (m, 2H), 1.34-1.28 (m, 2H), 0.86 (t, J=7.2 Hz, 3H). MS (ESI): mass calcd. For $C_{11}H_{15}BCl_3NO_2$ 309.03, m/z found 274.0 [M+H]$^+$. Purity by HPLC: 97.25% (220 nm), 94.9% (254 nm).

Example 7: 5,7-dichloro-N-(cyclobutylmethyl)-1-hydroxy-3H-2,1-benzoxaborol-6-amine

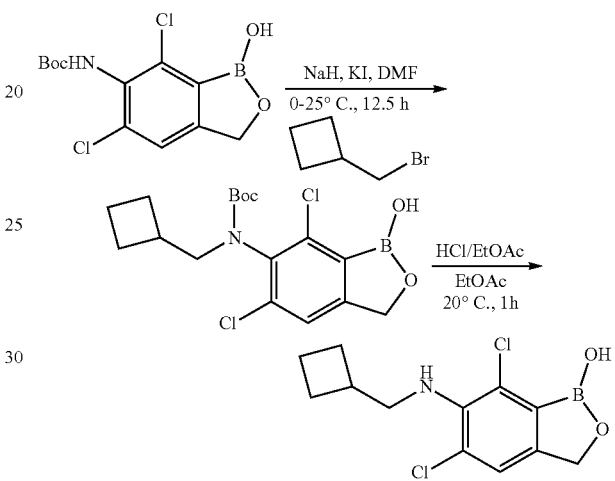

tert-butyl N-(cyclobutylmethyl)-N-(5,7-dichloro-1-hydroxy-3H-2,1-benzoxaborol-6-yl)carbamate To a mixture of tert-butyl N-(5,7-dichloro-1-hydroxy-3H-2,1-benzoxaborol-6-yl)carbamate (200 mg, 629.01 umol, 1 eq) in DMF (3 mL) was added NaH (75.47 mg, 1.89 mmol, 60% purity, 3 eq) in portions at 0° C. The mixture was stirred at 0° C. for 0.5 h, then KI (10.44 mg, 62.90 umol, 0.1 eq) and bromomethylcyclobutane (140.61 mg, 943.51 umol, 105.72 uL, 1.5 eq) were added at 0° C. The mixture was stirred at 20° C. for 12 h. After completion, the reaction mixture was quenched by addition of saturated aqueous NH$_4$Cl solution (10 mL), extracted with EtOAc (10 mL×3). The combined organic layers were washed with brine (10 mL×3), dried over anhydrous Na$_2$SO$_4$, filtered and concentrated under reduced pressure. The residue was purified by prep-HPLC (column: Nano-micro Kromasil C18 100*30 mm 5 um; mobile phase: [water (0.1% TFA)-ACN]; B %: 55%-85%, 10 min) to give tert-butyl N-(cyclobutylmethyl)-N-(5,7-dichloro-1-hydroxy-3H-2,1-benzoxaborol-6-yl)carbamate (34 mg, 88.07 umol, 14.00% yield) as a white solid. $^1$H NMR (DMSO-$d_6$, 400 MHz) δ 9.35 (s, 1H), 7.61 (s, 1H), 5.04-4.94 (m, 2H), 3.60-3.52 (m, 2H), 2.51-2.40 (m, 1H), 1.89-1.87 (m, 2H), 1.74-1.73 (m, 2H), 1.57-1.54 (m, 2H), 1.46-1.25 (m, 9H). MS (ESI): mass calcd. For $C_{17}H_{22}BCl_2NO_4$ 385.10, m/z found 330.0 [M-56+H]$^+$. Purity by HPLC: 99.48% (220 nm), 97.18% (254 nm).

To a mixture of tert-butyl N-(cyclobutylmethyl)-N-(5,7-dichloro-1-hydroxy-3H-2,1-benzoxaborol-6-yl)carbamate (0.18 g, 466.23 umol, 1 eq) in EtOAc (5 mL) was added HCl/EtOAc (4 M, 2.33 mL, 20 eq) at 20° C. The mixture was stirred at 20° C. for 1 h. The reaction mixture concentrated under reduced pressure to give 5,7-dichloro-N-(cyclobutyl-methyl)-1-hydroxy-3H-2,1-benzoxaborol-6-amine (142 mg, HCl) as a yellow solid. $^1$H NMR (DMSO-$d_6$, 400 MHz) δ 7.41 (s, 1H), 4.88 (s, 2H), 3.26 (d, J=7.2 Hz, 2H), 2.50-2.39 (m, 1H), 1.96-1.94 (m, 2H), 1.82-1.78 (m, 2H), 1.68-1.63 (m, 2H). MS (ESI): mass calcd. For $C_{12}H_{14}BCl_2NO_2$ 285.05, m/z found 286.0 [M+H]$^+$. Purity by HPLC: 98.38% (220 nm), 97.97% (254 nm).

Example 8: 5,7-dichloro-1-hydroxy-N-isopropyl-3H-2,1-benzoxaborol-6-amine

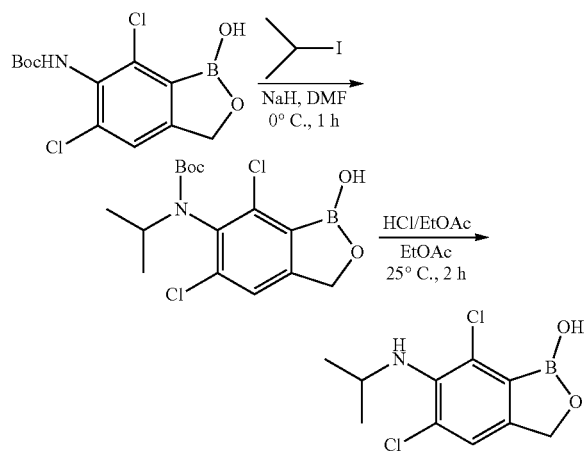

tert-butyl N-(5,7-dichloro-1-hydroxy-3H-2,1-benzoxaborol-6-yl)-N-isopropyl-carbamate To a solution of tert-butyl N-(5,7-dichloro-1-hydroxy-3H-2,1-benzoxaborol-6-yl)carbamate (0.3 g, 943.51 umol, 1 eq) in DMF (6 mL) was added NaH (67.93 mg, 1.70 mmol, 60% purity, 1.8 eq) at 0° C. After addition, the mixture was stirred at this temperature for 30 min, then 2-iodopropane (240.58 mg, 1.42 mmol, 141.52 uL, 1.5 eq) was added at 0° C. The resulting mixture was stirred at 0° C. for 30 min. The reaction mixture was poured into saturated aqueous NH$_4$Cl solution (20 mL) at 0° C., and stirred for 3 min. The aqueous phase was extracted with EtOAc (15 mL×3). The combined organic phase was washed with brine (10 mL×1), dried with anhydrous Na$_2$SO$_4$, filtered and concentrated in vacuum. The residue was purified by prep-HPLC (column: x-charge 150*25 mm*5 um; mobile phase: [water (0.1% TFA)-ACN]; B %: 45%-70%, 10 min) to give tert-butyl N-(5,7-dichloro-1-hydroxy-3H-2,1-benzoxaborol-6-yl)-N-isopropyl-carbamate (0.125 g, 347.18 umol, 36.80% yield) as a white solid. $^1$H NMR (DMSO-$d_6$, 400 MHz) δ 9.34 (s, 1H), 7.62 (s, 1H), 5.07-4.93 (m, 2H), 4.09-3.97 (m, 1H), 1.49-1.24 (m, 9H), 1.18-1.16 (m, 6H).

To a solution of tert-butyl N-(5,7-dichloro-1-hydroxy-3H-2,1-benzoxaborol-6-yl)-N-isopropyl-carbamate (0.12 g, 333.30 umol, 1 eq) in EtOAc (10 mL) was added HCl/EtOAc (4 M, 12.40 mL, 148.82 eq). The mixture was stirred at 25° C. for 2 h, and then concentrated under reduced pressure. The residue was purified by prep-HPLC (column: x-charge 150*25 mm*5 um; mobile phase: [water (0.1% TFA)-ACN]; B %: 35%-55%, 10 min) to give 5,7-dichloro-1-hydroxy-N-isopropyl-3H-2,1-benzoxaborol-6-amine (0.072 g, 277.00 umol, 83.11% yield, 100% purity) as a white solid. $^1$H NMR (DMSO-$d_6$, 400 MHz) δ 7.44 (s, 1H), 4.90 (s, 2H), 3.80-3.72 (m, 1H), 1.11 (d, J=6.4 Hz, 6H). MS (ESI): mass calcd. For $C_{10}H_{12}BCl_2NO_2$ 259.03, m/z found 260.1 [M+H]$^+$. Purity by HPLC: 100% (220 nm), 100% (254 nm).

Example 9: 5,7-dichloro-N-(cyclopropylmethyl)-1-hydroxy-3H-2,1-benzoxaborol-6-amine

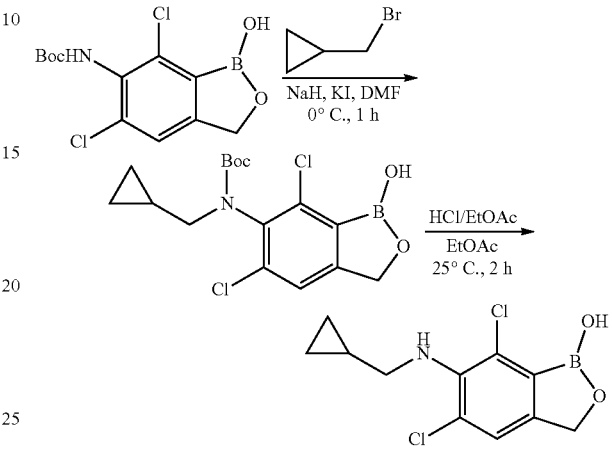

tert-butyl N-(cyclopropylmethyl)-N-(5,7-dichloro-1-hydroxy-3H-2,1-benzoxaborol-6-yl)carbamate To a solution of tert-butyl N-(5,7-dichloro-1-hydroxy-3H-2,1-benzoxaborol-6-yl)carbamate (0.3 g, 943.51 umol, 1 eq) in DMF (6 mL) was added NaH (71.70 mg, 1.79 mmol, 60% purity, 1.9 eq) at 0° C., and kept stirring for 30 min, then KI (15.66 mg, 94.35 umol, 0.1 eq) and bromomethylcyclopropane (191.06 mg, 1.42 mmol, 135.51 uL, 1.5 eq) were added to the reaction mixture at 0° C. The resulting mixture was stirred at 0° C. for 30 min, and then poured into saturated aqueous NH$_4$Cl solution (20 mL) at 0° C., and stirred for 3 min. The aqueous phase was extracted with EtOAc (15 mL×3). The combined organic phase was washed with brine (10 mL×1), dried over anhydrous Na$_2$SO$_4$, filtered and concentrated in vacuum. The residue was purified by prep-HPLC (column: x-charge 150*25 mm*5 um; mobile phase: [water (0.1% TFA)-ACN]; B %: 50%-65%, 10 min) to give tert-butyl N-(cyclopropylmethyl)-N-(5,7-dichloro-1-hydroxy-3H-2,1-benzoxaborol-6-yl)carbamate (0.095 g, 255.34 umol, 27.06% yield) as a white solid. $^1$H NMR (DMSO-$d_6$, 400 MHz) δ 9.34 (s, 1H), 7.62 (s, 1H), 5.05-4.96 (m, 2H), 3.47-3.28 (m, 2H), 1.47 (s, 3H), 1.27 (s, 6H), 0.96-0.89 (m, 1H), 0.36-0.30 (m, 2H), 0.02-0.06 (m, 2H).

To a solution of tert-butyl N-(cyclopropylmethyl)-N-(5,7-dichloro-1-hydroxy-3H-2,1-benzoxaborol-6-yl)carbamate (0.095 g, 255.34 umol, 1 eq) in EtOAc (10 mL) was added HCl/EtOAc (4 M, 9.50 mL, 148.82 eq). The mixture was stirred at 25° C. for 2 h. The reaction mixture was concentrated under reduced pressure, giving a residue that was purified by prep-HPLC (column: x-charge 150*25 mm*5 um; mobile phase: [water (0.1% TFA)-ACN]; B %: 35%-53%, 10 min) to give 5,7-dichloro-N-(cyclopropylmethyl)-1-hydroxy-3H-2,1-benzoxaborol-6-amine (0.053 g, 194.90 umol, 76.33% yield, 100% purity) as a yellow solid. $^1$H NMR (DMSO-$d_6$, 400 MHz) δ 7.42 (s, 1H), 4.89 (s, 2H), 3.08 (d, J=7.2 Hz, 2H), 0.96-0.93 (m, 1H), 0.41-0.37 (m, 2H), 0.17-0.14 (m, 2H). MS (ESI): mass calcd. For $C_{11}H_{12}BCl_2NO_2$ 271.03 m/z found 272.1 [M+H]$^+$. Purity by HPLC: 100% (220 nm), 100% (254 nm).

Example 10: 6-amino-5,7-dichlorobenzo[c][1,2]oxaborol-1(3H)-ol

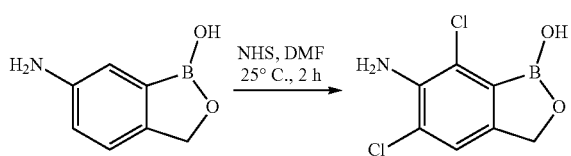 [SMILES: Nc1ccc2c(c1)B(O)OC2 ; Nc1c(Cl)cc2c(c1Cl)B(O)OC2]

A solution of compound 6-aminobenzo[c][1,2]oxaborol-1(3H)-ol (1 g, 6.7 mmol) in DMF (10 mL) were added NCS (2 g, 13 mmol) at 0° C. in portions, the mixture was stirred at 25° C. for 2 h, LCMS indicated the reaction was completed, the reaction was quenched by ice-water (20 mL), and extracted with EtOAc (10 mL×5), the organic layers were washed with brine (20 mL×3), dried over anhydrous $Na_2SO_4$, concentrated in vacuo. The residue was purified by prep-HPLC (0.1% FA in MeCN and $H_2O$) to give 6-amino-5,7-dichlorobenzo[c][1,2]oxaborol-1(3H)-ol (55 mg, 4%) as a white powder. $^1$H NMR (400 MHz, DMSO-$d_6$): δ 9.09 (s, 1H), 7.32 (s, 1H), 5.37 (s, 2H), 4.85 (s, 2H) ppm. HPLC purity: 99.97% at 210 nm and 99.89% at 254 nm. MS (ESI): mass calcd. For $C_7H_6BCl_2NO_2$ 217.0 m/z found 218.0 $[M+H]^+$.

Example 11: 5-Chloro-4-(difluoromethoxy)benzo[c][1,2]oxaborol-1(3H)-ol

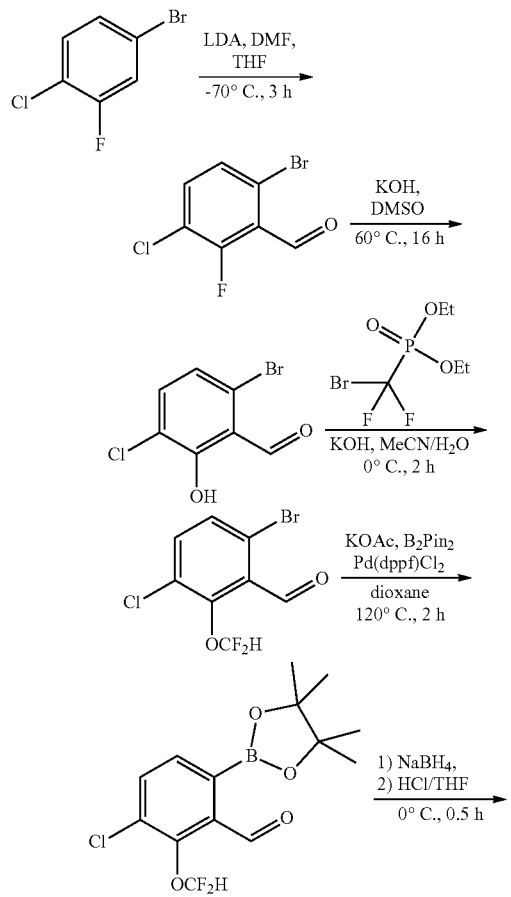

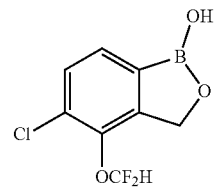

To a solution of 4-bromo-1-chloro-2-fluorobenzene (23 g, 109.81 mmol, 1 eq) in THF (200 mL) was added LDA (2 M, 65.89 mL, 1.2 eq) at −70° C. The mixture was stirred at −70° C. for 2 h, and to it was added DMF (12.04 g, 164.72 mmol, 12.67 mL, 1.5 eq). The mixture was stirred at −70° C. for 1 h. Water (100 mL) and aqueous $NH_4Cl$ (100 mL) were added to the reaction mixture at 0° C. The aqueous phase was extracted with ethyl acetate (100 mL×3). The combined organic phase was washed with brine (150 mL), dried with anhydrous $Na_2SO_4$, filtered and concentrated in vacuum. The residue was purified by Combi Flash (1000 mesh silica gel, petroleum ether/ethyl acetate=80/1 to 50/1) to afford 6-bromo-3-chloro-2-fluoro benzaldehyde (21 g, 88.44 mmol, 80.53% yield) as a yellow solid. $^1$H NMR (CDCl$_3$, 400 MHz): δ 10.32 (s, 1H), 7.51-7.44 (m, 2H) ppm. To a solution of 6-bromo-3-chloro-2-fluorobenzaldehyde (19 g, 80.02 mmol, 1 eq) in DMSO (200 mL) was added a solution of KOH (4.49 g, 80.02 mmol, 1 eq) in $H_2O$ (5 mL) at 25° C. The mixture was stirred at 60° C. for 15 h. Then more KOH (4.49 g, 80.02 mmol, 1 eq) in water (5 mL) was added to the mixture at 25° C. The mixture was stirred at 60° C. for one more hour. The residue was poured into ice-water (w/w=1/1, 150 mL) and was adjusted to pH 5 by 2N HCl acid. The aqueous phase was extracted with ethyl acetate (150 mL×3). The combined organic phase was washed with water (100 mL) and brine (100 mL), dried with anhydrous $Na_2SO_4$, filtered and concentrated in vacuum. The residue was purified by combi flash (1000 mesh silica gel, petroleum ether/ethyl acetate=5/1 to 2/1) to afford 6-bromo-3-chloro-2-hydroxybenzaldehyde (10 g, 42.47 mmol, 53.1% yield) as a yellow solid. $^1$H NMR (CDCl$_3$, 400 MHz): δ 12.53 (s, 1H), 10.31 (s, 1H), 7.45 (d, J=8.4 Hz, 1H), 7.16 (d, J=8.4 Hz, 1H) ppm. To a mixture of 6-bromo-3-chloro-2-hydroxybenzaldehyde (9 g, 38.22 mmol, 1 eq) and 1-[[bromo(difluoro)methyl]-ethoxy-phosphoryl]oxyethane (15.31 g, 57.33 mmol, 1.5 eq) in $H_2O$ (100 mL) and MeCN (100 mL) was added a solution of KOH (21.45 g, 382.23 mmol, 10 eq) in $H_2O$ (20 mL) at 0° C. The mixture was stirred at 0° C. for 2 h. The residue was poured into ice-water (100 mL). The aqueous phase was extracted with ethyl acetate (100 mL×3). The combined organic phase was washed with brine (100 mL), dried with anhydrous $Na_2SO_4$, filtered and concentrated in vacuum. The residue was purified by combi flash (1000 mesh silica gel, petroleum ether/ethyl acetate=3/1, 1/1) to afford 6-bromo-3-chloro-2-(difluoromethoxy)benzaldehyde (4.7 g, 16.46 mmol, 43.1% yield) as a yellow solid. $^1$H NMR (CDCl$_3$, 400 MHz): δ 10.28 (s, 1H), 7.58 (d, J=8.8 Hz, 1H), 7.53 (d, J=8.8 Hz, 1H), 6.69 (t, J=74.0 Hz, 1H) ppm. To a mixture of 6-bromo-3-chloro-2-(difluoromethoxy)benzaldehyde (1 g, 3.50 mmol, 1 eq) and Pin$_2$B$_2$ (4.45 g, 17.51 mmol, 5 eq) in 1,4-dioxane (20 mL) was added KOAc (515.68 mg, 5.25 mmol, 1.5 eq) and Pd(dppf)Cl$_2$ (128.16 mg, 175.15 umol, 0.05 eq) in one portion at 25° C. The mixture was stirred at 120° C. for 2 h under N$_2$. The reaction mixture was filtered, and the filtrate was concentrated. The residue was purified by Combi Flash (1000 mesh silica gel, petroleum ether/ethyl acetate=10/1, 3/1) to afford 3-chloro-2-(difluoro methoxy)-6-(4,4,5,5-tetramethyl-1,3,2-dioxaborolan-2-yl)benzaldehyde (0.5 g, 1.50 mmol, 42.9% yield) as yellow oil. $^1$H NMR (CDCl$_3$, 400 MHz): δ 10.35 (s, 1H), 7.67 (d, J=8.0 Hz, 1H), 7.41 (d, J=8.0 Hz, 1H), 6.64

(t, J=74.0 Hz, 1H), 1.43 (s, 12H) ppm. To a mixture of 3-chloro-2-(difluoromethoxy)-6-(4,4,5,5-tetramethyl-1,3,2-dioxaborolan-2-yl) benzaldehyde (0.33 g, 992.38 umol, 1 eq) in THF (10 mL) was added NaBH$_4$ (168.95 mg, 4.47 mmol, 4.5 eq) at 0° C. The mixture was stirred at 0° C. for 0.5 h. The residue was poured into ice-water (w/w=1/1, 10 mL) and adjusted to pH=5. The aqueous phase was extracted with ethyl acetate (10 mL×3). The combined organic phase was washed with brine (10 mL), dried with anhydrous Na$_2$SO$_4$, filtered and concentrated in vacuum. The residue was purified by prep-HPLC (column: Nano-micro Kromasil C18 100*30 mm 5 um; mobile phase: [water (0.1% TFA)-ACN]; B %: 35%-45%, 10 min) to afford 5-chloro-4-(difluoromethoxy)benzo[c][1,2]oxaborol-1(3H)-ol (0.143 g, 605.70 umol, 61.0% yield, 99.28% purity) as a white solid. $^1$H NMR (DMSO-d$_6$, 400 MHz): δ 9.52 (s, 1H), 7.68 (d, J=8.0 Hz, 1H), 7.61 (d, J=8.0 Hz, 1H), 7.16 (t, J=73.2 Hz, 1H), 5.07 (s, 2H) ppm. MS (ESI): m/z=233.0 [M−H]$^-$. HPLC: 99.28% (220 nm), 100% (254 nm).

Example 12: 7-Bromo-4-chlorobenzo[c][1,2]oxaborol-1(3H)-ol

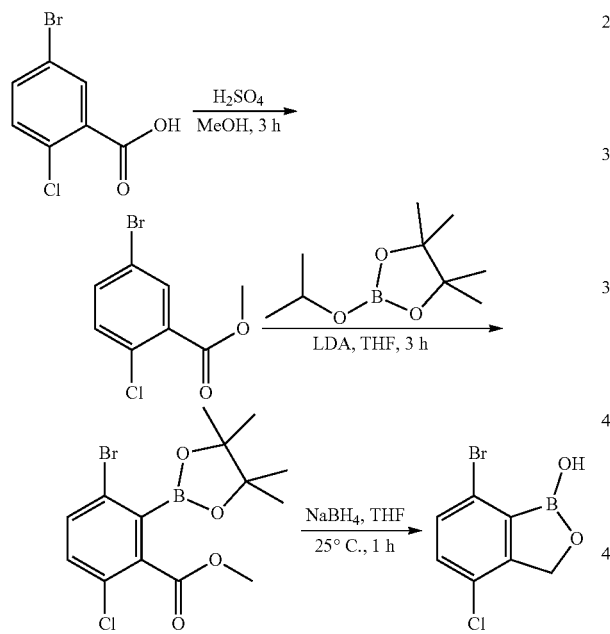

To a solution of 5-bromo-2-chlorobenzoic acid (24.8 g, 105.32 mmol, 1 eq) in MeOH (100 mL) was added H$_2$SO$_4$ (10.33 g, 105.32 mmol, 5.61 mL, 1 eq), and the mixture was refluxed for 3 h. It was concentrated under reduced pressure to remove most of methanol. The residue was added to cold water (300 mL) and stirred for 10 min. The mixture was filtered, and the white cake was washed with cold water (100 mL), and then dried to give methyl 5-bromo-2-chlorobenzoate (24.9 g, 99.80 mmol, 94.8% yield) as white solid. $^1$H NMR (CDCl$_3$, 400 MHz): δ 7.96 (d, J=2.8 Hz, 1H), 7.78 (dd, J=8.8, 2.8 Hz, 1H), 7.54 (d, J=8.8 Hz, 1H), 3.86 (s, 3H) ppm. To a mixture of methyl 5-bromo-2-chlorobenzoate (5 g, 20.04 mmol, 1 eq) and 2-isopropoxy-4,4,5,5-tetramethyl-1,3,2-dioxaborolane (7.46 g, 40.08 mmol, 8.18 mL, 2 eq) in THF (100 mL) was added LDA (2 M, 30.06 mL, 3 eq) in one portion at −60° C. under N$_2$. The mixture was stirred at −60° C. for 3 h under N$_2$. After completion, the reaction mixture was quenched by addition of aqueous NH$_4$Cl solution (20 mL) and extracted with EtOAc (30 mL×3). The combined organic layers were washed with brine (30 mL×3), dried over anhydrous Na$_2$SO$_4$, filtered and concentrated under reduced pressure. The residue was purified by column chromatography (SiO$_2$, petroleum ether/ethyl acetate=I/O to 50:1). Compound methyl 3-bromo-6-chloro-2-(4,4,5,5-tetramethyl-1,3,2-dioxaborolan-2-yl)benzoate (3 g, 7.99 mmol, 39.9% yield) was obtained as a yellow solid. $^1$H NMR (DMSO-d$_6$, 400 MHz): δ 7.75 (d, J=8.8 Hz, 1H), 7.55 (d, J=8.8 Hz, 1H), 3.86 (s, 3H), 1.31 (s, 12H) ppm. MS (ESI): m/z=276.9 [M−99]$^+$. To a mixture of methyl 3-bromo-6-chloro-2-(4,4,5,5-tetramethyl-1,3,2-dioxaborolan-2-yl) benzoate (0.3 g, 799.04 umol, 1 eq) in THF (10 mL) and MeOH (2 mL) was added NaBH$_4$ (60.46 mg, 1.60 mmol, 2 eq) in one portion at 0° C. The mixture was stirred at 25° C. for 1 h. The reaction mixture was quenched with HCl (2N, 3 mL), and extracted with EtOAc (10 mL×3). The combined organic layers were washed with brine (10 mL×3), dried over anhydrous Na$_2$SO$_4$, filtered and concentrated under reduced pressure to give a residue. The residue was purified by prep-HPLC (column: Nano-micro Kromasil C18 100*30 mm 5 um; mobile phase: [water (0.1% TFA)-ACN]; B %: 35%-60%, 10 min). Compound 7-bromo-4-chlorobenzo[c][1,2]oxaborol-1(3H)-ol (64.4 mg, 260.43 umol, 32.6% yield) was obtained as a white solid. $^1$H NMR (DMSO-d$_6$, 400 MHz): δ 9.36 (s, 1H), 7.55 (d, J=8.0 Hz, 1H), 7.46 (d, J=8.0 Hz, 1H), 4.98 (s, 2H) ppm. MS (ESI): m/z=244.8 & 246.8 [M−H]$^-$. HPLC: 99.64% (220 nm), 100.00% (254 nm).

Example 13: 5-Chloro-7-(difluoromethoxy)benzo[c][1,2]oxaborol-1(3H)-ol

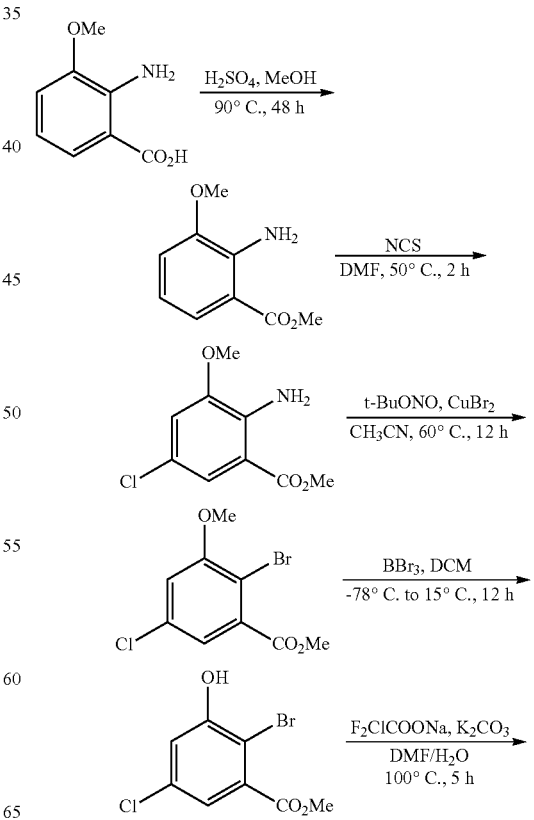

-continued

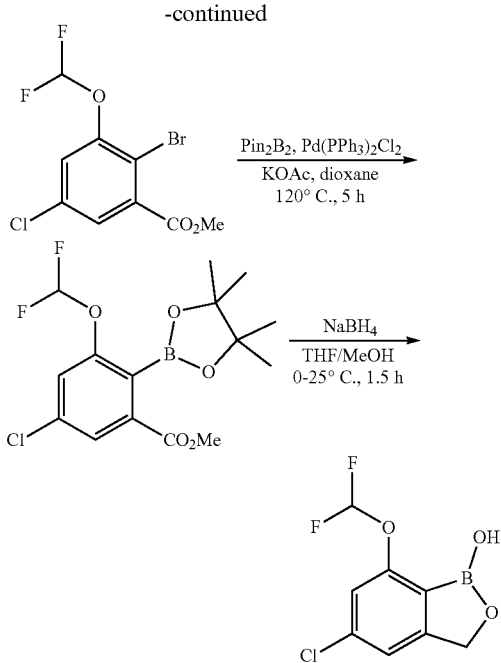

To a solution of 2-amino-3-methoxybenzoic acid (20 g, 119.64 mmol, 1 eq) in MeOH (250 mL) was added H$_2$SO$_4$ (55.20 g, 551.56 mmol, 30 mL, 98% purity, 4.61 eq). The mixture was stirred at 90° C. for 48 h. The reaction mixture was concentrated under reduced pressure to remove MeOH. The residue was diluted with H$_2$O (100 mL) and was added saturated aqueous NaHCO$_3$ until pH=8. The aqueous solution was extracted with EtOAc (50 mL×3). The combined organic layers were washed with brine (75 mL×2), dried over Na$_2$SO$_4$, filtered and concentrated under reduced pressure to give methyl 2-amino-3-methoxybenzoate (17 g, 93.83 mmol, 78.4% yield) as brown oil. $^1$H NMR (CDCl$_3$, 400 MHz): δ 7.48 (d, J=7.2 Hz, 1H), 6.86 (d, J=6.8 Hz, 1H), 6.58 (t, J=8.0 Hz, 1H), 6.01 (br s, 2H), 3.88 (s, 6H) ppm. To a solution of methyl 2-amino-3-methoxybenzoate (16.5 g, 91.07 mmol, 1 eq) in DMF (200 mL) was added NCS (12.53 g, 93.80 mmol, 1.03 eq) at 25° C. The resulting mixture was stirred and heated at 50° C. for 2 h. The reaction mixture was quenched by addition ice-water (500 mL) at 0° C., and then extracted with EtOAc (100 mL×3). The combined organic layers were washed with brine (300 mL×3), dried over Na$_2$SO$_4$, filtered and concentrated under reduced pressure to give methyl 2-amino-5-chloro-3-methoxybenzoate (19 g, 88.11 mmol, 96.8% yield) as brown oil, which was used into the next step without further purification. $^1$H NMR (CDCl$_3$, 400 MHz): δ 7.46 (d, J=2.0 Hz, 1H), 6.79 (d, J=2.4 Hz, 1H), 6.01 (br s, 2H), 3.87 (s, 6H) ppm. To a solution of methyl 2-amino-5-chloro-3-methoxybenzoate (19 g, 88.11 mmol, 1 eq) in CH$_3$CN (300 mL) was added CuBr$_2$ (40 g, 179.09 mmol, 8.39 mL, 2.03 eq) resulting in a dark color. The mixture was stirred for 20 min at 25° C., and t-BuONO (16.36 g, 158.60 mmol, 18.86 mL, 1.8 eq) was added dropwise over 10 min. The reaction mixture was stirred for additional 30 min, and then heated at 60° C. for 12 h. The reaction mixture was concentrated in vacuo, and water (300 mL) and EtOAc (100 mL) were added. The resulting mixture was stirred at 25° C. for 30 min. The organic phase became brown, and the aqueous was green with insoluble materials. The whole mixture was filtered through Celite and washed with EtOAc (100 mL×3). The organic layer was separated, washed with brine (100 mL×3), dried over Na$_2$SO$_4$ and filtered and concentrated under reduced pressure to give a residue. The residue was purified by column chromatography (SiO$_2$, petroleum ether/ethyl acetate=10/1 to 3/1) to give methyl 2-bromo-5-chloro-3-methoxybenzoate (16 g, 57.24 mmol, 65.0% yield) as a white solid. $^1$H NMR (CDCl$_3$, 400 MHz): δ 7.28 (d, J=2.4 Hz, 1H), 6.98 (d, J=2.4 Hz, 1H), 3.94 (s, 3H), 3.93 (s, 3H) ppm. To a solution of methyl 2-bromo-5-chloro-3-methoxybenzoate (10 g, 35.78 mmol, 1 eq) in DCM (300 mL) was slowly added BBr$_3$ (26.89 g, 107.33 mmol, 10.34 mL, 3 eq) at −78° C. under N$_2$. To the reaction mixture was slowly added MeOH (100 mL), and the resulting mixture was stirred at 20° C. for 30 min. It was mixed with ice-water 500 mL at 0° C., and the organic phase was separated. The aqueous was extracted with DCM (100 mL×3). The combined organic layers were washed with brine (200 mL×2), dried over Na$_2$SO$_4$, filtered and concentrated under reduced pressure to give a residue. The residue was purified by column chromatography (SiO$_2$, petroleum ether/ethyl acetate=10/1 to 0/1) to give methyl 2-bromo-5-chloro-3-hydroxy-benzoate (4 g, 15.07 mmol, 42.1% yield) as a yellow solid. $^1$H NMR (CDCl$_3$, 400 MHz): δ 7.43 (d, J=2.4 Hz, 1H), 7.20 (d, J=2.4 Hz, 1H), 6.09 (s, 1H), 3.95 (s, 3H) ppm. To a solution of methyl 2-bromo-5-chloro-3-hydroxybenzoate (0.9 g, 3.39 mmol, 1 eq) in DMF (15 mL) and H$_2$O (1.5 mL) were added sodium 2-chloro-2,2-difluoro-acetate (1.81 g, 11.86 mmol, 3.5 eq) and K$_2$CO$_3$ (937.03 mg, 6.78 mmol, 2 eq) at 20° C. The reaction was stirred under argon at 100° C. for 5 h. The reaction mixture was quenched by addition H$_2$O (30 mL) at 20° C., and then the aqueous was extracted with EtOAc (15 mL×3). The combined organic layers were washed with brine (20 mL×3), dried over Na$_2$SO$_4$, filtered and concentrated under reduced pressure to give methyl 2-bromo-5-chloro-3-(difluoro methoxy)benzoate (750 mg, 2.38 mmol, 70.1% yield) as a yellow solid. $^1$H NMR (CDCl$_3$, 400 MHz): δ 7.60 (d, J=2.4 Hz, 1H), 7.37 (d, J=2.4 Hz, 1H), 6.56 (t, J=72.8 Hz, 1H), 3.96 (s, 3H) ppm. A mixture of methyl 2-bromo-5-chloro-3-(difluoromethoxy)benzoate (0.7 g, 2.22 mmol, 1 eq), Pin$_2$B$_2$ (2.82 g, 11.09 mmol, 5 eq), KOAc (544.37 mg, 5.55 mmol, 2.5 eq), and Pd(PPh$_3$)$_2$Cl$_2$ (155.73 mg, 221.87 umol, 0.1 eq) in 1,4-dioxane (20 mL) was degassed and purged with N$_2$ for 3 times, and then the mixture was stirred at 120° C. for 5 h under N$_2$ atmosphere. The reaction was cooled and filtered. The filtrate was concentrated under reduced pressure to give a residue. The residue was purified by column chromatography (SiO$_2$, petroleum ether/ethyl acetate=30/1 to 5/1) to give methyl 5-chloro-3-(difluoromethoxy)-2-(4,4,5,5-tetramethyl-1,3,2-dioxaborolan-2-yl)benzoate (280 mg, 772.28 umol, 34.81% yield) as a white solid. $^1$H NMR (CDCl$_3$, 400 MHz): δ 7.83 (d, J=1.6 Hz, 1H), 7.29 (s, 1H), 6.59 (t, J=74.4 Hz, 1H), 3.91 (s, 3H), 1.43 (s, 12H) ppm. To a solution of methyl 5-chloro-3-(difluoromethoxy)-2-(4,4,5,5-tetramethyl-1,3,2-dioxaborolan-2-yl)benzoate (280 mg, 772.28 umol, 1 eq) and NaBH$_4$ (87.65 mg, 2.32 mmol, 3 eq) in THF (5 mL) was added MeOH (0.5 mL) at 0° C. It was stirred at 25° C. for 1 h. Then the mixture was adjusted to pH=2-3 with HCl (2 M) and stirred for 30 min. The resulting reaction mixture was added water (20 mL) at 0° C., and then extracted with EtOAc (10 mL×3). The combined organic layers were washed with brine (15 mL×2), dried over Na$_2$SO$_4$, filtered and concentrated under reduced pressure to give a residue. The residue was purified by prep-HPLC (column: Phenomenex luna C18 250*50 mm*10 um; mobile phase: [water (0.1% TFA)-ACN]; B %: 25%-55%, 20 min) to give 5-chloro-7-(difluoromethoxy)benzo[c][1,2]oxaborol-1(3H)-ol (110 mg, 469.30 umol, 60.8% yield, 100% purity) as a white solid. $^1$H NMR (DMSO-d$_6$, 400 MHz): δ 9.36 (s, 1H), 7.41 (d, J=1.2 Hz, 1H), 7.39 (t, J=74.0 Hz, 1H), 7.17 (s, 1H), 4.99 (s, 2H) ppm. MS (ESI): m/z=233.1 [M-H]$^-$. HPLC: 100% (220 nm), 100% (254 nm).

Example 14: 5-Chloro-6-(difluoromethoxy)benzo[c][1,2]oxaborol-1(3H)-ol

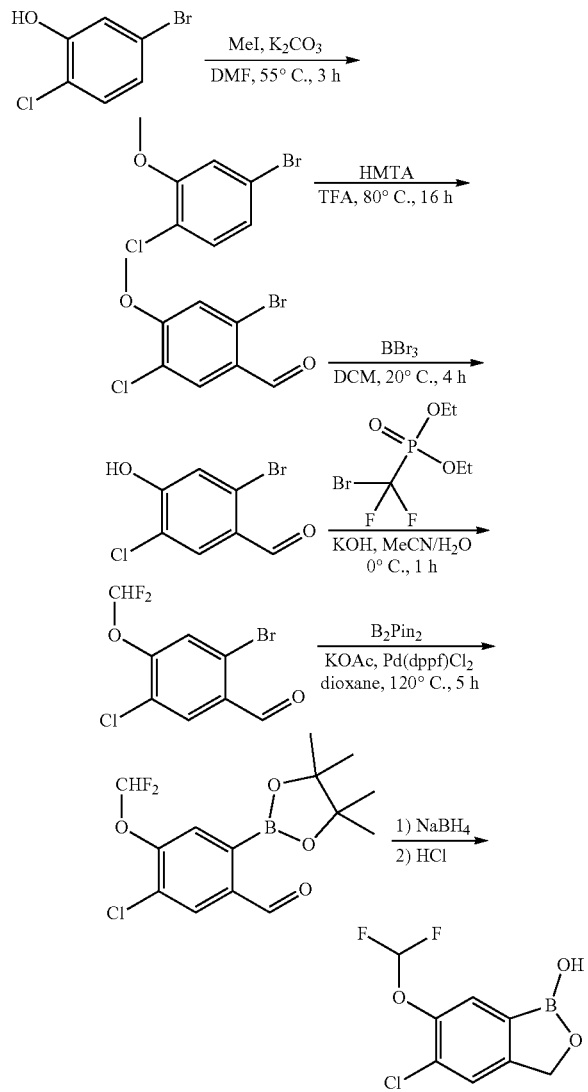

To a solution of 5-bromo-2-chlorophenol (20 g, 96.41 mmol, 1 eq) in DMF (150 mL) was added K$_2$CO$_3$ (26.65 g, 192.82 mmol, 2 eq) and MeI (16.42 g, 115.69 mmol, 7.20 mL, 1.2 eq). The mixture was stirred at 55° C. for 3 h. Water (1000 mL) was added and the mixture was extracted with petroleum ether (300 mL×3). The combined organics were washed with brine (200 mL×2), dried over Na$_2$SO$_4$, filtered and concentrated in vacuo. Compound 4-bromo-1-chloro-2-methoxybenzene (20 g, crude) was obtained as a yellow solid. $^1$H NMR (DMSO-d$_6$, 400 MHz): δ 7.37 (d, J=8.4 Hz, 1H), 7.33 (d, J=2.0 Hz, 1H), 7.14 (dd, J=8.4 Hz, 2.0 Hz, 1H), 3.88 (s, 3H) ppm. To a solution of 4-bromo-1-chloro-2-methoxybenzene (20 g, 90.30 mmol, 12.27 mL, 1 eq) in TFA (200 mL) was added 6,7,8,9-tetrazatricyclodecane (HMTA, 18.99 g, 135.45 mmol, 25.32 mL, 1.5 eq). The mixture was stirred at 80° C. for 16 h. Water (200 mL) was added and the mixture was extracted with EtOAc (80 mL×3). The combined organics were concentrated in vacuo. There were some solid formed. The mixture was filtered, and the filtrate was washed with aqueous NaHCO$_3$ to pH=7. The organic layer was separated and washed with brine (50 mL×2), dried over Na$_2$SO$_4$, filtered and concentrated in vacuo. Compound 2-bromo-5-chloro-4-methoxy benzaldehyde (15 g, crude) was obtained as a yellow solid. $^1$H NMR (DMSO-d$_6$, 400 MHz): δ 10.04 (s, 1H), 7.84 (s, 1H), 7.55 (s, 1H), 4.01 (s, 3H) ppm. To a solution of 2-bromo-5-chloro-4-methoxybenzaldehyde (5 g, 20.04 mmol, 1 eq) in DCM (30 mL) was added BBr$_3$ (12.55 g, 50.10 mmol, 4.83 mL, 2.5 eq) at 0° C. The mixture was stirred at 20° C. for 4 h. Water (2 mL) was added and there were some solid formed. The mixture was filtered, and the filter cake was washed with H$_2$O (10 mL). The filter cake was dried in vacuo. Compound 2-bromo-5-chloro-4-hydroxybenzaldehyde (4 g, crude) was obtained as a white solid. $^1$H NMR (DMSO-d$_6$, 400 MHz): δ 11.90 (s, 1H), 9.98 (s, 1H), 7.81 (s, 1H), 7.28 (s, 1H) ppm. To a solution of 2-bromo-5-chloro-4-hydroxybenzaldehyde (1 g, 4.25 mmol, 1 eq) in MeCN (10 mL) and H$_2$O (4 mL) was added a solution of KOH (2.38 g, 42.47 mmol, 10 eq) in H$_2$O (2 mL). The mixture was stirred at 0° C. for 30 minutes. Then to the mixture was added diethyl (bromodifluoromethyl)phosphonate (1.70 g, 6.37 mmol, 1.5 eq). It was stirred at 0° C. for 1 h and extracted with EtOAc (10 mL×4). The combined organics were washed with brine (5 mL×2), dried over Na$_2$SO$_4$, filtered and concentrated in vacuo. Compound 2-bromo-5-chloro-4-(difluoromethoxy)benzaldehyde (0.4 g, crude) was obtained as a yellow gum. $^1$H NMR (DMSO-d$_6$, 400 MHz): δ 10.09 (s, 1H), 7.97 (s, 1H), 7.83 (s, 1H), 7.56 (t, J=73.2 Hz, 1H) ppm. A mixture of 2-bromo-5-chloro-4-(difluoromethoxy) benzaldehyde (0.4 g, 1.40 mmol, 1 eq), 4,4,4',4',5,5,5',5'-octamethyl-2,2'-bi(1,3,2-dioxaborolane) (1.78 g, 7.01 mmol, 5 eq), KOAc (343.79 mg, 3.50 mmol, 2.5 eq) and Pd(dppf)Cl$_2$ (57.21 mg, 70.06 umol, 0.05 eq) in 1,4-dioxane (5 mL) was degassed and purged with N$_2$ for 3 times, and then the mixture was stirred at 120° C. for 5 h under N$_2$ atmosphere. The reaction mixture was filtered through a pad of celite. Then the filtrate was concentrated in vacuo. The residue was purified by prep-HPLC (column: Nano-micro Kromasil C18 100*30 mm 5 um; mobile phase: [water (0.1% TFA)-ACN]; B %: 15%-45%, 10 min). Compound 5-chloro-4-(difluoromethoxy)-2-(4,4,5,5-tetramethyl-1,3,2-dioxaborolan-2-yl)benzaldehyde (0.08 g, 240.58 umol, 17.2% yield) was obtained as a white solid. $^1$H NMR (DMSO-d$_6$, 400 MHz): δ 10.26 (s, 1H), 8.09 (s, 1H), 7.56 (s, 1H), 7.49 (t, J=73.2 Hz, 1H), 1.35 (s, 12H) ppm. To a solution of 5-chloro-4-(difluoromethoxy)-2-(4,4,5,5-tetramethyl-1,3,2-dioxaborolan-2-yl)benzaldehyde (0.08 g, 240.58 umol, 1 eq) in MeOH (10 mL) was added NaBH$_4$ (27.30 mg, 721.73 umol, 3 eq). The mixture was stirred at 20° C. for 10 minutes. HCl (2N, 10 mL) was added dropwise and concentrated in vacuo to remove the organic solvent. The mixture was extracted with EtOAc (10 mL×3). The combined organics were washed with brine (10 mL), dried over Na$_2$SO$_4$, filtered and concentrated in vacuo. The residue was purified by prep-HPLC (column: Nano-micro Kromasil C18 100*30 mm 5 um; mobile phase: [water (0.1% TFA)-ACN]; B %: 35%-50%, 10 min). Compound 5-chloro-6-(difluoromethoxy)-1-hydroxy-3H-2,1-benzoxaborole (7.8 mg, 33.08 umol, 13.8% yield) was obtained as a white solid. $^1$H NMR (DMSO-d$_6$, 400 MHz): δ 9.41 (s, 1H), 7.70 (s, 1H), 7.66 (s, 1H), 7.27 (t, J=73.2 Hz, 2H), 4.98 (s, 2H) ppm. MS (ESI): m/z=233.0 [M−H]$^-$. HPLC: 99.4% (220 nm), 100% (254 nm).

Example 15: 5-Chloro-6-(cyclobutylamino)benzo[c][1,2]oxaborol-1(3H)-ol

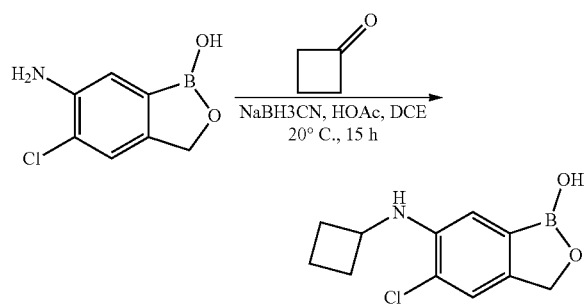

To a mixture of 6-amino-5-chlorobenzo[c][1,2]oxaborol-1(3H)-ol (0.1 g, 545.26 umol, 1 eq) and cyclobutanone (191.08 mg, 2.73 mmol, 203.71 uL, 5 eq) and HOAc (98.23 mg, 1.64 mmol, 93.55 uL, 3 eq) in DCE (3 mL) was added NaBH$_3$CN (85.66 mg, 1.36 mmol, 2.5 eq) in one portion at 20° C. The mixture was stirred at 20° C. for 15 hr. Ice-water (2 mL) was added to the mixture. The mixture was concentrated in reduced pressure. The residue was purified by prep-HPLC (column: Nano-micro Kromasil C18 100*30 mm 5 um; mobile phase: [water (0.1% TFA)-ACN]; B %: 35%-60%, 10 min) and then 0.5 ml 2 N HCl added, the eluent was lyophilized to afford 5-chloro-6-(cyclobutylamino)benzo[c][1,2]oxaborol-1(3H)-ol (54 mg, 223.60 umol, 41.0% yield) as yellow solid. $^1$H NMR (DMSO-d$_6$, 400 MHz): δ 7.33 (s, 1H), 6.98 (s, 1H), 4.83 (s, 2H), 3.88-3.85 (m, 1H), 2.37-2.32 (m, 2H), 1.98-1.93 (m, 2H), 1.76-1.71 (m, 2H) ppm. MS (ESI): m/z=236.0 [M−H]$^-$. HPLC: 98.34% (220 nm), 100% (254 nm).

Example 16: 7-Chloro-6-(ethylamino)benzo[c][1,2]oxaborol-1(3H)-ol

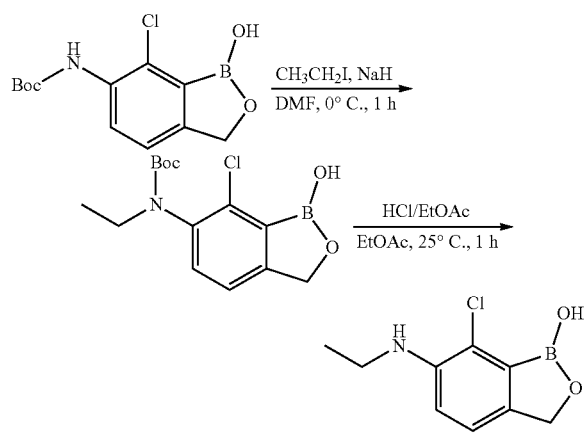

To a mixture of tert-butyl N-(7-chloro-1-hydroxy-3H-2,1-benzoxaborol-6-yl)carbamate (0.4 g, 1.41 mmol, 1 eq) in DMF (4 mL) was added NaH (169.29 mg, 4.23 mmol, 60% purity, 3 eq) in portions at 0° C. The mixture was stirred at 0° C. for 0.5 h and then CH$_3$CH$_2$I (330.07 mg, 2.12 mmol, 169.27 uL, 1.5 eq) was added. The mixture was stirred at 0° C. for 0.5 h and quenched by addition of saturated aqueous NH$_4$Cl (10 mL), and extracted with EtOAc (10 mL×3). The combined organic layers were washed with brine (10 mL×3), dried over anhydrous Na$_2$SO$_4$, filtered and concentrated under reduced pressure. The residue was purified by prep-HPLC (column: x-charge 150*25 mm*5 um; mobile phase: [water (0.1% TFA)-ACN]; B %: 40%-70%, 10 min). Compound tert-butyl N-(7-chloro-1-hydroxy-3H-2,1-benzoxaborol-6-yl)-N-ethyl-carbamate (321 mg, 1.03 mmol, 73.02% yield) was obtained as a yellow solid. $^1$H NMR (DMSO-d$_6$, 400 MHz): δ 9.18 (s, 1H), 7.42 (d, J=8.0 Hz, 1H), 7.37 (d, J=8.0 Hz, 1H), 5.00 (s, 2H), 3.68-3.61 (m, 1H), 3.45-3.40 (m, 1H), 1.46-1.27 (m, 9H), 1.07-0.99 (m, 3H) ppm. MS (ESI): m/z=256.0 [M+H-56]$^+$. HPLC: 97.63% (220 nm), 90.3% (254 nm). To a mixture of tert-butyl N-(7-chloro-1-hydroxy-3H-2,1-benzoxaborol-6-yl)-N-ethyl-carbamate (260 mg, 834.49 umol, 1 eq) in EtOAc (5 mL) was added HCl/EtOAc (4 M, 4.17 mL, 20 eq) in one portion at 25° C. The mixture was stirred at 25° C. for 1 h and concentrated under reduced pressure. Compound 7-chloro-6-(ethylamino)benzo[c][1,2]oxaborol-1(3H)-ol HCl salt (172 mg) was obtained as a yellow solid. $^1$H NMR (DMSO-d$_6$, 400 MHz): δ 7.20 (d, J=8.0 Hz, 1H), 6.95 (d, J=7.2 Hz, 1H), 5.25 (broad s, 3H), 4.87 (s, 2H), 3.19 (q, J=7.2 Hz, 2H), 1.17 (t, J=7.2 Hz, 3H) ppm. MS (ESI): m/z=212.0 [M+H]$^+$. HPLC: 100.00% (220 nm), 100.00% (254 nm).

Section III: Biological Materials and Methods

Example 1. Fungal and Oomycetal Isolates

The isolates of *Aspergillus flavus* NRRL 3518 and *Rhizoctonia solani* NRRL 66082 were obtained from USDA Agricultural Research Service Culture Collection. The collection of *Colletotrichum sublineolum* FSP270 was gifted by Dr. Louis Prom at USDA-ARS Crop Germplasm Research in College Station, TX. The isolates of *Botrytis cinerea* B16, *Botrytis cinerea* B17, *Candida albicans* was obtained from the Plant Pathology and Environmental Microbiology Department at The Pennsylvania State University, University Park, PA. The *Alternaria linariae* isolate was kindly gifted by Inga Meadows at The Department of Entomology and Plant Pathology, Mountain Research Station in North Carolina State University, Waynesville, NC. The collection of *Mycosphaerella fijiensis* 11CR-33 was given by Dr. Jean Ristaino at the Department of Plant Pathology in North Carolina State University, Raleigh, NC. The isolates of *Botrytis cinerea* B05.10, *Fusarium oxysporum* f. sp. *cubense* TR4, and *Phytophthora capsici* were obtained from the Texas A&M Agrilife Research, College Station, TX.

Example 2. Fungal and Oomycetal Inoculum Preparation

Unless specified, most of the organisms were maintained on potato dextrose agar (PDA), and spores can be isolated from the cultures after 1-2 weeks of incubation at room temperature (20-22° C.) with 12 hours fluorescent light (Philips, F40LW) and 12 hours blacklight (Philips, F40T12) photoperiod. The final concentrations of all inocula were 1×10$^5$ CFU/mL.

*Mycosphaerella fijiensis*: Briefly, mycelial cultures of *M. fijiensis* isolates 11CR-33 grown on PDA medium were macerated in water, and 1-5 mL of the resulting suspension was pipetted onto plates of modified V8 medium (0.2 g/L CaCO$_3$, 100 mL/L V8 juice and 20 g/L Difco agar). Cultures were incubated at 20° C. under continuous, cool-white fluorescent and black light. After 5-7 days, sporulation plates were stimulated to produce conidia by adding 2 mL water and brushing the plates with a paint brush or cell spreader and removing the resulting suspension. After another 5-7 days, conidia were harvested in the same way, adding 2 mL 0.05% Tween 20 solution, brushing the plates to dislodge spores, and removing the spore suspension by pipetting. Spores were diluted in half strength broth medium.

*Rhizoctonia solani*: due to insufficient spore obtained from these fungi, inocula were prepared as mycelium visible fragments. In brief, fungal mycelium grown on agar media were cut into 1×1 mm pieces and cultured in autoclaved broth medium (such as PDB and V8). After 3-7 days of incubation at 22-24° C., mycelia were harvested by filtering through one layer of Miracloth. The mycelia were homogenated in half strength of broth medium using household blender for 10 seconds and filtered through one layer Miracloth. The resultant visible fragments were diluted in half strength broth medium.

*Fusarium oxysporum* f. sp. *cubense*: the isolate of *Fusarium oxysporum* f. sp. *cubense* TR4 was maintained on V8 agar (20%—200 mL V8 juice, 2 g $CaCO_3$, 15 g Agar, 800 mL distilled water. Spore suspensions were prepared in half strength PDB broth medium with 0.1% Tween 20.

Example 3. In Vitro Antifungal and Anti-Oomycetal Efficacy of Boron-Based Molecules A number of boron-based compounds were stocked in DMSO with the concentration of 5000 μg/mL (stored at −20° C.). The stock solutions were further diluted into sterile half strength broth media in the in vitro assay, in which DMSO final concentration is not greater than 1% (v/v).

The minimal inhibitory concentrations (MICs) for individual compounds were determined by following a modified broth microdilution protocol. The studies were performed in flat bottom, 96-well microtiter plates (Greiner Bio-One).

The individual MICs were determined in triplicate in a final volume of 0.2 mL/well with antifungal concentrations of 0.2-25 μg/mL (8 serial dilutions down from 25 μg/mL [25, 12.5, 6.25, 3.13, 1.56, 0.78, 0.39 and 0.20 μg/mL]; control studies with 0 μg/mL of compounds were performed in parallel for each plate). Plates sealed with clear polyester film (VWR) were incubated at a temperature of about 22° C. The progress of fungal growth was monitored at 72 hours. The MICs were determined as the lowest antifungal concentrations that inhibited fungal growth by greater than 95% (determined as relative absorbance using the Bio-Tek® Synergy™ H1 microplate reader at 600 nm) relative to the corresponding antifungal-free control.

Figure 3F:
FIG. 3A-3TT is a table showing antifungal and antibacterial inhibition results for a number of exemplary boron-based compounds as described in Example 3 and Example 4 of the Biological Materials and Methods examples. In light of taxonomical updating, reference to *Alternaria solani* in FIG. 3A-3TT should be considered as a reference to *Alternaria linariae*.
Figure 3T:
Figure 3I:
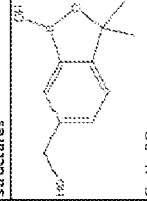

The MIC results and inhibition results of the antifungal screening are shown in FIG. 3A-3TT.

Example 4. In Vitro Antibacterial Efficacy of Boron-Based Molecules

A number of boron-based compounds were stocked in DMSO with the concentration of 5000 μg/mL (stored at −20° C.). The stock solutions were further diluted into sterile half strength broth media in the in vitro assay, in which DMSO final concentration is not greater than 1% (v/v).

*Escherichia coli* (*E coli*) and *Agrobacterium tumefaciens* (*A. tumefaciens*) were used in antibacterial screening. The final concentration of bacterial in each well was 0.001 OD600.

The inhibition rates (%) for individual compounds were determined by following a modified broth microdilution protocol. The studies were performed in flat bottom, 96-well microtiter plates (Greiner Bio-One). The individual inhibition rates were determined in triplicate in a final volume of 0.2 mL/well with antibacterial concentration of 25 μg/mL; control studies with 0 μg/mL of compounds were performed in parallel for each plate). Plates sealed with clear polyester film (VWR) were incubated at a temperature of about 22° C. The progress of bacterial growth was monitored at 48 hours. The inhibition rates were determined using the following formula: inhibition rate %=(OD600 of Control−OD600 of compound)/OD600 of Control*100. (determined as relative absorbance using the Bio-Tek® Synergy™ H1 microplate reader at 600 nm) relative to the corresponding antifungal-free control.

The MIC results and inhibition results of the antibacterial screening are shown in FIG. 3A-3TT.

In one aspect, the present invention relates to benzoxaborole formulations comprising a benzoxaborole, a non-ionic surfactant or a non-ionic and ionic surfactant mixture, and a carrier. At least one of the non-ionic surfactant, the non-ionic and ionic surfactant mixture, or the carrier comprise a Lewis base or a N—H or O—H bond. The carrier is a solid or a liquid.

In accordance with another aspect of the present invention, a method of using benzoxaborole formulations for phytopathogenic compositions comprises administering the formulation to crops, seeds, plants, plant parts, plant propagation material, in need thereof. The composition comprises a benzoxaborole, a non-ionic surfactant or a non-ionic and ionic surfactant mixture, and a carrier. At least one of the non-ionic surfactant, the non-ionic and ionic surfactant mixture, or the carrier comprise a Lewis base or a N—H or O—H bond. The carrier is a solid or a liquid.

In a preferred embodiment, the carrier is a liquid, wherein the liquid carrier is a mixture comprising more than one suitable liquid carrier. In another preferred embodiment, the liquid carrier comprises a protic solvent or at least one alcohol selected from the group consisting of: $C_1$-$C_{15}$ branched alcohols, $C_1$-$C_{15}$ linear alcohols, benzyl alcohol, oleyl alcohol, cetyl alcohol, lauryl alcohol, 2-propanol, methanol, n-decanol, 1-propanol, ethanol, 1-hexanol, isobutyl alcohol, n-octanol, 1-butanol, pentanol, cyclohexanol, and mixtures thereof. In another preferred embodiment, the liquid carrier comprises at least one protic solvent and at least one aprotic solvent.

Preferred non-ionic surfactants include, but are not limited to, high molecular weight polymers, polycondensates of ethylene oxide with fatty alcohols or with fatty acids or with fatty amines, substituted phenols (in particular alkylphenols or arylphenols such as mono- and di-(polyoxyalkylene alkylphenol), polycondensates of ethylene oxide with phosphated tristyrylphenols and polycondensates of ethylene oxide with phosphoric esters of alcohols or phenols, amine ethoxylates, castor oil ethoxylates and polyethylene glycol derivatives of hydrogenated castor oil (for example PEG 40 castor oil hydrogenated), sorbitan fatty acid ester ethoxylates, polyoxyethylene sorbitan monolaurates (for example polysorbate 20), sorbitan fatty acid esters such as sorbitan monolaurate and sorbitan monostearate, polyoxyethylene polyoxypropylene sorbitan monolaurates, non-ionic ethoxylates, branched and unbranched secondary alcohol ethoxylates, nonylphenol ethoxylates, octylphenol ethoxylates, fatty alcohol ethoxylates, alkyl phenol ethoxylates, castor oil based ethoxylates, fatty acid ethoxylates, EO-PO block co-polymers, acrylic co-polymers, styrene acrylic polymers, polyalkylene oxide block copolymers, sorbitan(ol) ester ethoxylates, sarcosinates, alkyl polysaccrharides, alkyl amine ethoxylates, amine oxides, siliconics, ethoxylated Graft & Comb polymers, and propoxylated and non-ethoxylated Graft & Comb polymers.

Preferred ionic surfactants include, but are not limited to, alkyl ether phosphates, alkyl phenol ether phosphates, alkyl phenol ether sulphates, condensed naphthalene sulfonates and salts, sodium alkyl naphthalene sulphonate blends, sodium alkyl naphthalene sulfonate, sodium alkylnapthalene formaldehyde condensates, sodium naphthalene sulphonate condensate, aromatic hydrocarbon sulfonic acids, aromatic hydrocarbon sulfonic salts, aromatic hydrocarbon sulfonic blends, fatty alcohol sulphates, alkyl ether carboxylic acids, alkyl ether carboxylic salts, alkyl ether sulphates, monosulphosuccinates, polysulphosuccinates, alkyl phosphates, alkyl benzene sulphonic acids, alkyl benzene sulphonic salts, lignosulphonates and salts, alkylaryl sulphonates, alkylbenzene sulphonates, calcium alkylaryl sulphonates, and alpha olefin sulphonates.

Formulations of benzoxaboroles comprising different classes of surfactants and carriers have not been previously contemplated. The unpredictable formulations are useful in agriculture.

In some preferred embodiments of the present invention, the applied formulation has a pH of 5-10. In other preferred embodiments of the present invention, the applied formulation has a pH of 5.5-8.

In preferred embodiments of the present invention, the formulation is 0.1-60% w/v (or w/w) benzoxaborole if the carrier is a liquid. In a feature of this embodiment, the formulation is 1-60% w/w (or w/w) benzoxaborole.

In preferred embodiments of the present invention, the formulation is 10-80% w/v (or w/w) benzoxaborole if the carrier is a solid.

In preferred embodiments of the present invention, the formulation includes at least 0.01% w/w non-ionic surfactant or non-ionic and ionic surfactant mixture and can include up to 20% w/w non-ionic surfactant or non-ionic and ionic surfactant mixture.

In preferred embodiments of the present invention, the surfactant comprises at least one of a fatty alcohol ethoxylate, alkyl phenol ethoxylate, castor oil based ethoxylate, fatty acid ethoxylate, a polyoxyethylene sorbitan monolaurate (for example polysorbate 20), a sorbitan fatty acid ester such as sorbitan monolaurate and sorbitan monostearate, a polyoxyethylene polyoxypropylene sorbitan monolaurate, EO-PO block co-polymer, acrylic co-polymer, styrene acrylic polymer, sorbitan(ol) ester ethoxylate, sarcosinate, alkyl polysaccharide, alkyl amine ethoxylate, amine oxide, siliconics, graft and/or comb polymer (ethoxylated or propoxylated and non ethoxylated), alkyl ether phosphate, alkyl phenol ether phosphate, alkyl phenol ether sulphate, a calcium alkylaryl sulphonate, condensed naphthalene sulfonate and/or salt, sodium alkyl naphthalene sulphonate blend, sodium naphthalene sulphonate condensate, aromatic hydrocarbon sulfonic acid/salt and their blends, fatty alcohol sulphate, alkyl ether carboxylic acid and/or salt, alkyl ether sulphate, mono- and/or polysulphosuccinate, alkyl phosphate, alkyl benzene sulphonic acid and/or salt, lignosulphonate and/or salt, and alpha olefin sulphonate. In another preferred embodiment, the surfactant is at least one of a(n): amine ethoxylates, alkylaryl sulphonates, alkylbenzene sulphonates, castor oil ethoxylates and polyethylene glycol derivatives of hydrogenated castor oil, sorbitan fatty acid ester ethoxylates, sorbitan fatty acid esters, non-ionic ethoxylates, branched and unbranched secondary alcohol ethoxylates, nonylphenol ethoxylates, or octylphenol ethoxylates.

In preferred embodiments of the present invention, the formulation additionally includes an antioxidant.

In other preferred embodiments of the present invention, the formulation can include combinations of active ingredients, biologics, extracts, adjuvants, antioxidants, or other additives.

An applied formulation may be obtained by diluting the formulation. The formulation may be diluted into water to obtain the applied formulation. An applied formulation can be produced by diluting the formulation, then spraying, atomizing, dusting, scattering, coating, or pouring. The formulation can also be applied directly (i.e., without dilution) by spraying, atomizing, dusting, scattering, coating, or pouring.

Pathogens including fungi, bacteria, insects, parasites may be controlled using the formulations described herein for the benefit of plants. The formulations or applied formulations may be applied or administered systemically, topically, in the soil, as a seed treatment, or foliarly.

A method of reducing growth of a target fungus/bacteria/insect/pest is contemplated. In accordance with the method, a target fungus/bacteria/pest is contacted with an effective amount of the compounds described herein, and that contact is maintained for a period of time sufficient to control and/or inhibit growth of the target fungus/bacteria/pest. For example, contact is carried out by administering the compounds described herein to the target fungus/bacteria/pest where the administration is topical, soil, seed treatment, foliar, or systemic. In some embodiments, the administration is repeated.

In another aspect of the present disclosure, the compounds described herein are used for reducing overall damage of plants and plant parts as well as losses in harvested fruits or vegetables caused by bacteria, fungi, and/or phytopathogens.

Furthermore, in another aspect, the compounds described herein, increase the overall plant health.

Furthermore, the compounds described herein, have potent microbicidal activity and can be used for control of unwanted pathogens and microorganisms, such as fungi and bacteria, in crop protection and in the protection of plant materials. One of skill in the art will understand that the term "pathogen" broadly includes causative agents of disease, such as, pathogenic bacterium, fungi, virus, or other microorganism that can cause disease.

Wherein the described compound is a fungicide, it can be used in crop protection for control of phytopathogenic fungi. The compound can include an outstanding efficacy against a broad spectrum of phytopathogenic fungi, including soil borne pathogens, which are in particular members of the classes Plasmodiophoromycetes, Peronosporomycetes (Syn. Oomycetes), Chytridiomycetes, Zygomycetes, Ascomycetes, Basidiomycetes, and Deuteromycetes (Syn. Fungi imperfecti). Some fungicides are systemically active and can be used in plant protection as foliar, seed dressing or soil fungicide. Furthermore, the compounds are suitable for combating fungi, which inter alia infest wood or roots of plant.

Improved plant health refers to improved plant characteristics including: crop yield, more developed root system (improved root growth), improved root size maintenance, improved root effectiveness, tillering increase, increase in plant height, bigger leaf blade, less dead basal leaves, stronger tillers, greener leaf color, photosynthetic activity, more productive tillers, enhanced plant vigor, and increased plant stand.

In one aspect, the invention includes a compound of formula (I):

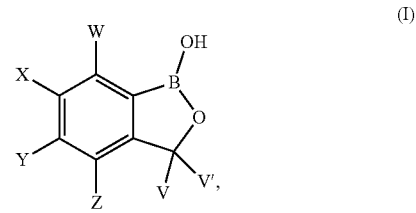

wherein:
W is selected from the group consisting of: hydrogen, halogen, $CH_3$, $CF_3$, Et, $OCH_3$, $OCF_3$, $OCF_2H$, $CFH_2$, OEt, O-n-propyl, O-n-butyl, O-iso-propyl, O-sec-butyl, O-iso-butyl, O-cyclopropyl, O-cyclbutyl, C(O)H, CN, $CH_2OH$, $SR^1$, and $S(O)R^1$, wherein $R^1$ is selected from C1-C3 hydrocarbyl;

X is selected from the group consisting of: hydrogen, $R^2$, $OR^2$, $OCF_2H$, $NR^2_2$, $NHR^2$, $NH_2$, halogen, $CO_2R^2$, CN, OH, $CH_2OH$, $NO_2$, C(O)H, $SR^2$, and $S(O)R^2$, wherein each $R^2$ is independently selected from C1-C7 hydrocarbyl and C3-C6 cyclohydrocarbyl or each $R^2$ can be taken together to form a ring;

Y is selected from the group consisting of: hydrogen, halogen, $CH_3$, $NO_2$, C(O)H, and $CO_2R^3$, wherein $R^3$ is selected from C1-C4 hydrocarbyl and C3-C4 cyclohydrocarbyl;

Z is selected from the group consisting of: hydrogen, halogen, $R^4$, $NR^4_2$, $NHR^4$, $NH_2$, $NO_2$, $CO_2R^4$, $OR^4$, OH, $OCF_2H$, $SR^4$, and $S(O)R^4$, wherein $R^4$ is selected from C1-C3 hydrocarbyl and C3 cyclohydrocarbyl; and V and V' are independently selected from the group consisting of hydrogen and $CH_3$, or a salt, stereoisomer, enantiomer, or tautomer thereof.

In another aspect, the invention includes a method for reducing or preventing an infestation by a pathogen by applying an effective amount of a compound according to any one of the above formulae, wherein the pathogen is selected from the group consisting of bacteria, microbes, fungi, and any combinations thereof.

In another aspect, the invention includes a method for reducing or preventing an infestation by a pathogen by applying a compound according to any one of the above formulae, wherein the pathogen is selected from the group consisting of bacteria, microbes, fungi, and any combinations thereof.

In yet another aspect, the invention includes a method for controlling or preventing an infestation of the pathogen by treating an, plant, plant part, or plant propagation material with an effective amount of a compound according to a compound of the disclosure.

In yet another aspect, the invention includes a method for controlling or preventing an infestation of the pathogen by treating a plant, plant part, or plant propagation material with a compound according to the disclosure.

The preceding is a simplified summary to provide an understanding of some embodiments of the present disclosure. This summary is neither an extensive nor exhaustive over-view of the present disclosure and its various embodiments. The summary presents selected concepts of the embodiments of the present disclosure in a simplified form as an introduction to the more detailed description presented below. As will be appreciated, other embodiments of the present disclosure are possible utilizing, alone or in combination, one or more of the features set forth above or described in detail below.

ENUMERATED EMBODIMENTS

1. A benzoxaborole formulation composition comprising:
    a benzoxaborole,
    a non-ionic surfactant, or a non-ionic and ionic surfactant mixture, and
    a carrier,
    wherein at least one of the non-ionic surfactant, the non-ionic and ionic surfactant mixture, and the carrier comprise a Lewis base or a N—H or O—H bond, and
    wherein the carrier is a solid or a liquid.

2. The composition of enumerated embodiment 1, wherein the benzoxaborole has a structure, (Ib):

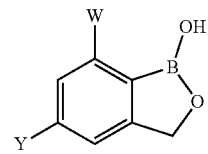

(Ib)

wherein:
    Y is selected from the group consisting of: fluorine, chlorine, bromine, and iodine, and
    W is selected from the group consisting of: hydrogen, methyl, fluorine, chlorine, bromine, and iodine.

3. The composition of enumerated embodiments 1 or 2, wherein the non-ionic and ionic surfactants are independently selected from the group consisting of: high molecular weight polymers, polycondensates of ethylene oxide with fatty alcohols or with fatty acids or with fatty amines, substituted phenols (in particular alkylphenols or arylphenols such as mono- and di-(polyoxyalkylene alkylphenol), polycondensates of ethylene oxide with phosphated tristyrylphenols and polycondensates of ethylene oxide with phosphoric esters of alcohols or phenols, amine ethoxylates, castor oil ethoxylates and polyethylene glycol derivatives of hydrogenated castor oil, sorbitan fatty acid ester ethoxylates, sorbitan fatty acid esters, non-ionic ethoxylates, branched and unbranched secondary alcohol ethoxylates, nonylphenol ethoxylates, octylphenol ethoxylates, fatty alcohol ethoxylates, alkyl phenol ethoxylates, castor oil based ethoxylates, fatty acid ethoxylates, EO-PO block co-polymers, acrylic co-polymers, styrene acrylic polymers, sorbitan(ol) ester ethoxylates, sarcosinates, alkyl polysaccrharides, alkyl amine ethoxylates, amine oxides, siliconics, ethoxylated Graft & Comb polymers, and propoxylated and non-ethoxylated Graft & Comb polymers, alkyl ether phosphates, alkyl phenol ether phosphates, alkyl phenol ether sulphates, condensed naphthalene sulfonates and salts, sodium alkyl naphthalene sulphonate blends, sodium naphthalene sulphonate condensate, aromatic hydrocarbon sulfonic acids, aromatic hydrocarbon sulfonic salts, aromatic hydrocarbon sulfonic blends, fatty alcohol sulphates, alkyl ether carboxylic acids, alkyl ether carboxylic salts, alkyl ether sulphates, monosulphosuccinates, polysulphosuccinates, alkyl phosphates, alkyl benzene sulphonic acids, alkyl benzene sulphonic salts, lignosulphonates and salts, alkylaryl sulphonates, alkylbenzene sulphonates, and alpha olefin sulphonates 4. The composition of any ones of enumerated embodiments 1 to 3, wherein the pKa of the benzoxaborole is between 6 and 10.

5. The composition of any one of enumerated embodiments 1 to 4, wherein the pKa of the benzoxaborole is between 7 and 10.

6. The composition of any one of enumerated embodiments 1 to 5, wherein the weight/volume % of benzoxaborole in the benzoxaborole formulation is 10% to 60% w/v if the carrier is a liquid, and the weight/volume % of benzoxaborole in the benzoxaborole formulation is 10% to 80% w/v if the carrier is a solid.

7. The composition of any one of enumerated embodiments 1 to 6, wherein the concentration of surfactant in the benzoxaborole formulation is between 0.1% and 20% w/v.

8. The composition of any one of enumerated embodiments 1 to 7, further comprising an antioxidant.

9. The composition of any one of enumerated embodiments 1 to 8, wherein the carrier is a liquid and is selected from the group consisting of: alcohols and glycols as well as their ethers and esters, ethylene glycol monomethyl ether, benzyl alcohol, a ketone, cyclohexanone, and isophorone.

10. The composition of enumerated embodiments 9, wherein the carrier further comprises a second liquid selected from the group consisting of: aliphatic hydrocarbons, aromatic hydrocarbons, substituted aromatic hydrocarbons, xylene mixtures, substituted naphthalenes, substituted aliphatic hydrocarbons and limonene.

11. The composition of enumerated embodiment 1, wherein the benzoxaborole has a structure II:

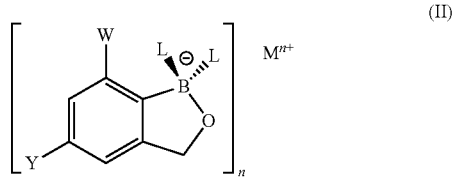

wherein:
Y is selected from the group consisting of: fluorine, chlorine, bromine, and iodine,
W is selected from the group consisting of: hydrogen, methyl, fluorine, chlorine, bromine, and iodine,
L is selected from the group consisting of hydroxyl, halogen, and straight chain or branched alkyl glycol, or L may be taken together to form a ring, and
M is a metal.

12. The composition of enumerated embodiments 11, wherein L is hydroxide and M is a group 1 or group 2 metal.

13. The composition of enumerated embodiments 11 wherein L is hydroxide and M is selected from the group consisting of K, Mg, Mn, Ca, Na, Zn, Al, Cu, and Fe.

14. The composition of enumerated embodiments 13, wherein L is hydroxide, n=1, and M is selected from the group consisting of K, Na, and Cu.

15. The composition of enumerated embodiments 11, wherein L is hydroxide, n=2, and M is selected from the group consisting of Cu, Mg, Mn, Ca, and Zn.

16. The composition of enumerated embodiments 11, wherein L is hydroxide, n=3, and M is selected from the group consisting of Cu, Mn, and Al.

17. The composition of enumerated embodiments 11, wherein L is fluoride and M is a group 1 or group 2 metal.

18. The composition of enumerated embodiments 11, wherein L is fluoride and M is selected from the group consisting of K, Na, and $NH_4$.

19. The composition of any one of enumerated embodiments 1 to 18, further comprising an aqueous diluent.

20. The composition of enumerated embodiments 19, wherein the aqueous diluent has a pH between about 5.5 and 9.5.

21. The composition of any one of enumerated embodiments 20, wherein the aqueous diluent has a pH between about 6 and 8.

22. A method of controlling phytopathogenic diseases on plants or plant propagation material thereof according to enumerated embodiments 1, which comprises applying to said composition in an effective amount.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combinations.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

We claim:

1. A method of controlling a phytopathogenic disease on crops, seeds, plants, plant parts, or plant propagation material comprising applying an effective amount of a benzoxaborole formulation composition comprising a benzoxaborole compound, decyl alcohol, isophorone, polyoxyethylene (20) sorbitan monolaurate, and calcium alkylaryl sulphonate,
wherein the benzoxaborole compound has a structure (Ib):

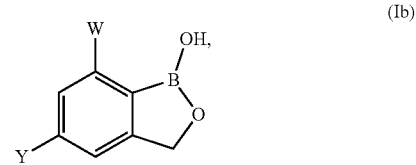

wherein:
Y is selected from the group consisting of: hydrogen, fluorine, chlorine, bromine, and iodine; and
W is selected from the group consisting of: hydrogen, methyl, fluorine, chlorine, bromine, and iodine,
or a salt, stereoisomer, enantiomer, or tautomer thereof; and
wherein the benzoxaborole formulation composition is applied to a crop, a seed, a plant, a plant part, soil, or a plant propagation material.

2. The method of claim 1, wherein said application is topical, to the soil, foliar, a foliar spray, systemic, a seed coating, a soil drench, directly in-furrow dipping, drenching, soil drenching, spraying, atomizing, irrigating, evaporating, dusting, fogging, broadcasting, foaming, painting, spreading-on, watering (drenching), and/or drip irrigating.

3. The method of claim 2, wherein the benzoxaborole formulation composition comprises 57.3% decyl alcohol, 19.1% isophorone, 4.5% calcium alkylaryl sulphonate, 8.0% polyoxyethylene (20) sorbitan monolaurate, 1.6% of a high molecular weight star polymer emulsifier, and 9.6% of the benzoxaborole compound.

4. A method for reducing, preventing, ameliorating, or inhibiting an infestation by a pathogen comprising applying an effective amount of a benzoxaborole formulation composition comprising a benzoxaborole compound, decyl alcohol, isophorone, polyoxyethylene (20) sorbitan monolaurate, and calcium alkylaryl sulphonate, wherein the benzoxaborole compound has a structure (Ib):

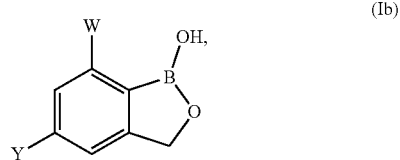

wherein:
Y is selected from the group consisting of: hydrogen, fluorine, chlorine, bromine, and iodine; and
W is selected from the group consisting of: hydrogen, methyl, fluorine, chlorine, bromine, and iodine,
or a salt, stereoisomer, enantiomer, or tautomer thereof; and
wherein the benzoxaborole formulation composition is applied to an animal, a plant, a plant part, seeds, soil, or plant propagation material.

5. The method of claim 4, wherein the benzoxaborole formulation composition comprises 57.3% decyl alcohol, 19.1% isophorone, 4.5% calcium alkylaryl sulphonate, 8.0% polyoxyethylene (20) sorbitan monolaurate, 1.6% of a high molecular weight star polymer emulsifier, and 9.6% of the benzoxaborole compound.

6. A method of controlling a phytopathogenic disease on crops, seeds, plants, plant parts, or plant propagation material comprising applying an effective amount of a benzoxaborole formulation composition comprising a benzoxaborole compound, decyl alcohol, isophorone, polyoxyethylene (20) sorbitan monolaurate, and calcium alkylaryl sulphonate, wherein the benzoxaborole compound has a structure (Ic):

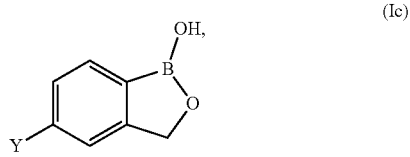

wherein Y is selected from the group consisting of: hydrogen, fluorine, chlorine, bromine, and iodine,
or a salt, stereoisomer, enantiomer, or tautomer thereof; and
wherein the benzoxaborole formulation composition is applied to a crop, a seed, a plant, a plant part, soil, or plant propagation material.

7. The method of claim 6, wherein said application is topical, to soil, foliar, a foliar spray, systemic, a seed coating, a soil drench, directly in-furrow dipping, drenching, soil drenching, spraying, atomizing, irrigating, evaporating, dusting, fogging, broadcasting, foaming, painting, spreading-on, watering (drenching), and/or drip irrigating.

8. The method of claim 7, wherein the benzoxaborole formulation composition comprises 57.3% decyl alcohol, 19.1% isophorone, 4.5% calcium alkylaryl sulphonate, 8.0% polyoxyethylene (20) sorbitan monolaurate, 1.6% of a high molecular weight star polymer emulsifier, and 9.6% of the benzoxaborole compound.

9. A method for reducing, preventing, ameliorating, or inhibiting an infestation by a pathogen comprising applying an effective amount of a benzoxaborole formulation composition comprising a benzoxaborole compound, decyl alcohol, isophorone, polyoxyethylene (20) sorbitan monolaurate, and calcium alkylaryl sulphonate, wherein the benzoxaborole compound has a structure (Ic):

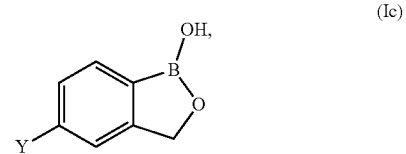

wherein Y is selected from the group consisting of: hydrogen, fluorine, chlorine, bromine, and iodine,
or a salt, stereoisomer, enantiomer, or tautomer thereof; and
wherein the benzoxaborole formulation composition is applied to an animal, a plant, a plant part, seeds, soil, or plant propagation material.

10. The method of claim 9, wherein the benzoxaborole formulation composition comprises 57.3% decyl alcohol, 19.1% isophorone, 4.5% calcium alkylaryl sulphonate, 8.0% polyoxyethylene (20) sorbitan monolaurate, 1.6% of a high molecular weight star polymer emulsifier, and 9.6% of the benzoxaborole compound.

* * * * *